United States Patent
Alberts et al.

(10) Patent No.: US 11,857,349 B2
(45) Date of Patent: *Jan. 2, 2024

(54) APPARATUS AND RELATED METHOD TO FACILITATE TEST VIA A COMPUTING DEVICE

(71) Applicants: THE CLEVELAND CLINIC FOUNDATION, Cleveland, OH (US); BIOGEN MA INC., Cambridge, MA (US)

(72) Inventors: Jay L. Alberts, Chagrin Falls, OH (US); David D. Schindler, Russell, OH (US); Jane Rhodes, Belmont, MA (US); Wendy Gabel, Boston, MA (US); Jim Best, Cambridge, MA (US)

(73) Assignees: THE CLEVELAND CLINIC FOUNDATION, Cleveland, OH (US); BIOGEN MA, INC., Cambridge, MA (US)

( * ) Notice: Subject to any disclaimer, the term of this patent is extended or adjusted under 35 U.S.C. 154(b) by 950 days.

This patent is subject to a terminal disclaimer.

(21) Appl. No.: 16/578,892

(22) Filed: Sep. 23, 2019

(65) Prior Publication Data
US 2020/0060626 A1 Feb. 27, 2020

Related U.S. Application Data

(63) Continuation of application No. 15/131,699, filed on Apr. 18, 2016, now Pat. No. 10,420,497.
(Continued)

(51) Int. Cl.
*A61B 5/00* (2006.01)
*A61B 3/032* (2006.01)
(Continued)

(52) U.S. Cl.
CPC ............ *A61B 5/7271* (2013.01); *A61B 3/032* (2013.01); *A61B 5/11* (2013.01); *A61B 5/112* (2013.01);
(Continued)

(58) Field of Classification Search
CPC ......... A61B 5/7271; A61B 3/032; A61B 5/11; A61B 5/112; A61B 5/1124; A61B 5/1125;
(Continued)

(56) References Cited

U.S. PATENT DOCUMENTS

| 3,606,331 A | 9/1971 | Morris |
| 5,093,985 A | 3/1992 | Houldsworth et al. |

(Continued)

OTHER PUBLICATIONS

Rudick, Richard A., et al. "The Multiple Sclerosis Performance Test (MSPT): an iPad-based disability assessment tool." JoVE (Journal of Visualized Experiments) 88 (2014): e51318.
(Continued)

*Primary Examiner* — Sean P Dougherty
(74) *Attorney, Agent, or Firm* — TAROLLI, SUNDHEIM, COVELL & TUMMINO L.L.P.

(57) ABSTRACT

This disclosure relates to a device to mechanically and electrically connect with a touch screen computing device, such as a tablet computer. The device can include a platform that can be moved into and out of physical contact with a surface of a touch screen. During engagement with the surface, the moveable platform electrically interacts with the touch screen (e.g., via capacitive coupling) to enable detection by the touch screen of contact members (e.g., pegs) even in the absence of user contact with the pegs.

12 Claims, 39 Drawing Sheets

Related U.S. Application Data

(60) Provisional application No. 62/149,344, filed on Apr. 17, 2015.

(51) Int. Cl.
*A61B 5/11* (2006.01)
*A61B 5/16* (2006.01)
*A61B 5/22* (2006.01)

(52) U.S. Cl.
CPC .......... *A61B 5/1124* (2013.01); *A61B 5/1125* (2013.01); *A61B 5/16* (2013.01); *A61B 5/165* (2013.01); *A61B 5/225* (2013.01); *A61B 5/4023* (2013.01); *A61B 5/4076* (2013.01); *A61B 5/4082* (2013.01); *A61B 5/4088* (2013.01); *A61B 5/162* (2013.01); *A61B 2560/04* (2013.01); *A61B 2562/0219* (2013.01); *G06F 2203/04809* (2013.01)

(58) Field of Classification Search
CPC .......... A61B 5/16; A61B 5/165; A61B 5/225; A61B 5/4023; A61B 5/4076; A61B 5/4082; A61B 5/4088; A61B 5/162; A61B 2560/04; A61B 2562/0219; G06F 2203/04809
See application file for complete search history.

(56) References Cited

U.S. PATENT DOCUMENTS

| | | | |
|---|---|---|---|
| 5,251,644 A | 10/1993 | Fitzgerald | |
| 5,289,389 A | 2/1994 | Keller | |
| 5,490,517 A | 2/1996 | Whitman et al. | |
| 6,066,105 A | 5/2000 | Guillen | |
| 8,310,351 B2 * | 11/2012 | Krahenbuhl | G06F 3/0416 340/815.45 |
| 8,325,150 B1 * | 12/2012 | Reeves | G06F 3/0202 400/486 |
| D715,759 S * | 10/2014 | Choi | D14/138 AB |
| 9,320,330 B2 | 4/2016 | Cooke et al. | |
| 9,952,629 B2 * | 4/2018 | Chae | H04M 1/23 |
| 2006/0181515 A1 | 8/2006 | Fletcher et al. | |
| 2006/0195018 A1 | 8/2006 | Guillen | |
| 2010/0238119 A1 * | 9/2010 | Dubrovsky | G06F 1/1626 345/169 |
| 2010/0302168 A1 | 12/2010 | Giancarlo et al. | |
| 2010/0328203 A1 * | 12/2010 | Hsu | G06F 1/1607 345/157 |
| 2011/0157056 A1 * | 6/2011 | Karpfinger | G06F 3/041 345/173 |
| 2012/0075236 A1 * | 3/2012 | Kim | G06F 3/041 345/173 |
| 2013/0335327 A1 * | 12/2013 | Solomon | G06F 3/0202 345/168 |
| 2013/0335364 A1 * | 12/2013 | Tseng | G06F 3/0393 345/174 |
| 2013/0344771 A1 | 12/2013 | Moll | |
| 2014/0022174 A1 * | 1/2014 | Chen | G06F 1/1669 345/168 |
| 2014/0120501 A1 * | 5/2014 | Cooke | B44C 3/123 434/81 |
| 2014/0163426 A1 | 6/2014 | Alberts et al. | |
| 2014/0333542 A1 * | 11/2014 | Barreca | G06F 3/04886 345/169 |
| 2015/0094621 A1 | 4/2015 | Alberts et al. | |
| 2015/0103019 A1 | 4/2015 | Young | |
| 2015/0297950 A1 | 10/2015 | Ono et al. | |
| 2016/0173664 A1 * | 6/2016 | Lewis | G06F 3/0227 455/575.8 |
| 2016/0302710 A1 | 10/2016 | Alberts et al. | |
| 2017/0012658 A1 * | 1/2017 | Otsubo | H04B 1/3888 |

OTHER PUBLICATIONS

PCT International Search Report and Written Opinion for corresponding International Application Serial No. PCT/US2016/028100, dated Jun. 28, 2016, pp. 1-11.

* cited by examiner

APPARATUS AND RELATED METHOD TO FACILITATE TEST VIA A COMPUTING DEVICE

CROSS-REFERENCE TO RELATED APPLICATION

This application is a continuation which claims priority to U.S. patent application no. 15/131,699, filed Apr. 18, 2016, which claims the benefit of priority from U.S. Provisional patent application no. 62/149344, filed Apr. 17, 2015, and entitled EXTERNAL MULTI-POINT TOUCHSCREEN APPARATUS, SYSTEMS AND RELATED METHODS OF USING, each of which are incorporated herein by reference in its entirety.

TECHNICAL FIELD

This disclosure relates generally to a performance test for evaluation of neurological function, and more specifically to a system and method that can implement the performance test to evaluate a patient's neurological and/or cognitive function.

BACKGROUND

Various diseases and disorders can adversely affect an individual's neurological and/or cognitive function. For example, multiple sclerosis (MS) is a chronic, progressive disease of the central nervous system (CNS), in which the myelin sheaths of axons of the brain, spinal cord and optic nerve become damaged, resulting in an inflammatory response. MS can lead to demyelination and scarring, as well as a broad spectrum of signs and symptoms, which often progresses to physical and cognitive disability.

MS-related disability ranges from minimal to severe, and evolution of disease manifestations over time is variable—both in the specific nature of the symptoms and disability and in the rate of deterioration. The historical approach to measuring MS-related disability has been use of a neurologist rating scale, called the Kurtzke Expanded Disability Scale (EDSS). The EDSS rates disease severity using a 20 point scale, ranging from 0 to 10 in 0.5 point increments, with increasing numbers reflecting increased disability. However, the EDSS has been criticized because it is neither precise nor quantitative. A newer approach has been to evaluate MS disease severity using a 3-part composite, called the Multiple Sclerosis Functional Composite (MSFC). The MSFC is a three-part, standardized, quantitative, assessment instrument for use in clinical studies, particularly clinical trials of MS. The MSFC can produce scores for each of the three individual measures—walking, hand/arm control, and cognitive function—as well as a composite score. However, since the MSFC measures are administered in person by a trained examiner, its usefulness outside of clinical settings tends to be impaired. Furthermore, current methods of executing examinations, including the MSFC, are manual, subjective and infrequent (only taking place during a scheduled appointment). A need exists to provide a tool and procedure to more easily, more frequently and more objectively allow a user to undergo examinations and functional testing and in a manner that can collect and store data for future use, such as longitudinal comparisons and population comparisons.

SUMMARY

This disclosure relates generally to an apparatus and related method to facilitate testing via a computing device, such as can be utilized to administer a test for the evaluation of cognitive and/or neuromotor function.

In one example, an apparatus includes a first housing portion comprising a test fixture having a base dimensioned and configured to overlay at least a display screen portion of a computing device. An arrangement of receptacles are formed in the test fixture and configured to receive contact members within the receptacles. The test fixture is attached to the computing device as to render each of the contact members independently detectable by the computing device while each respective contact member is received in the receptacles.

In another example, a mobile computing apparatus includes a computing device comprising a touch screen interface. The computing device includes memory that stores instructions to perform at least one of a neurological or cognitive function test and to store results data for each test in the memory. A test fixture is movably connected to the computing device. The test fixture includes a plurality of receptacles configured for receiving at least one contact member that, when placed in the receptacles, interact with the touch screen interface as to be detectable by the touch screen interface in the absence of direct contact by the user.

As yet another example, a method of using a mobile computing apparatus includes providing a computing device having a touch screen interface. The computing device includes memory to store instructions corresponding to at least a manual function test module. The method also includes placing a test fixture in a test position in which the test fixture is in an overlying position with the touch screen. The test fixture is pivotably connected to a base, which is attached to the computing device, and provides for rotational movement of the test fixture with respect to the touch screen interface of the computing device between the test position and a support position in which the base is operative to support the base and the computing device. The test fixture including a plurality of receptacles for receiving a plurality of contact members that, when placed in the receptacles while the test fixture is in the test position, enable interaction that is detectable by the touch screen in the absence of direct contact by the user. The method also includes executing the manual function test module and storing test data corresponding to user inputs in response to placing the contact members into the receptacles while the test fixture is in the test position during the execution thereof. The manual function test module can also calculate time values associated with the placing of the contact members and store the time values as part of the test data.

DETAILED DESCRIPTION

Figure 1:
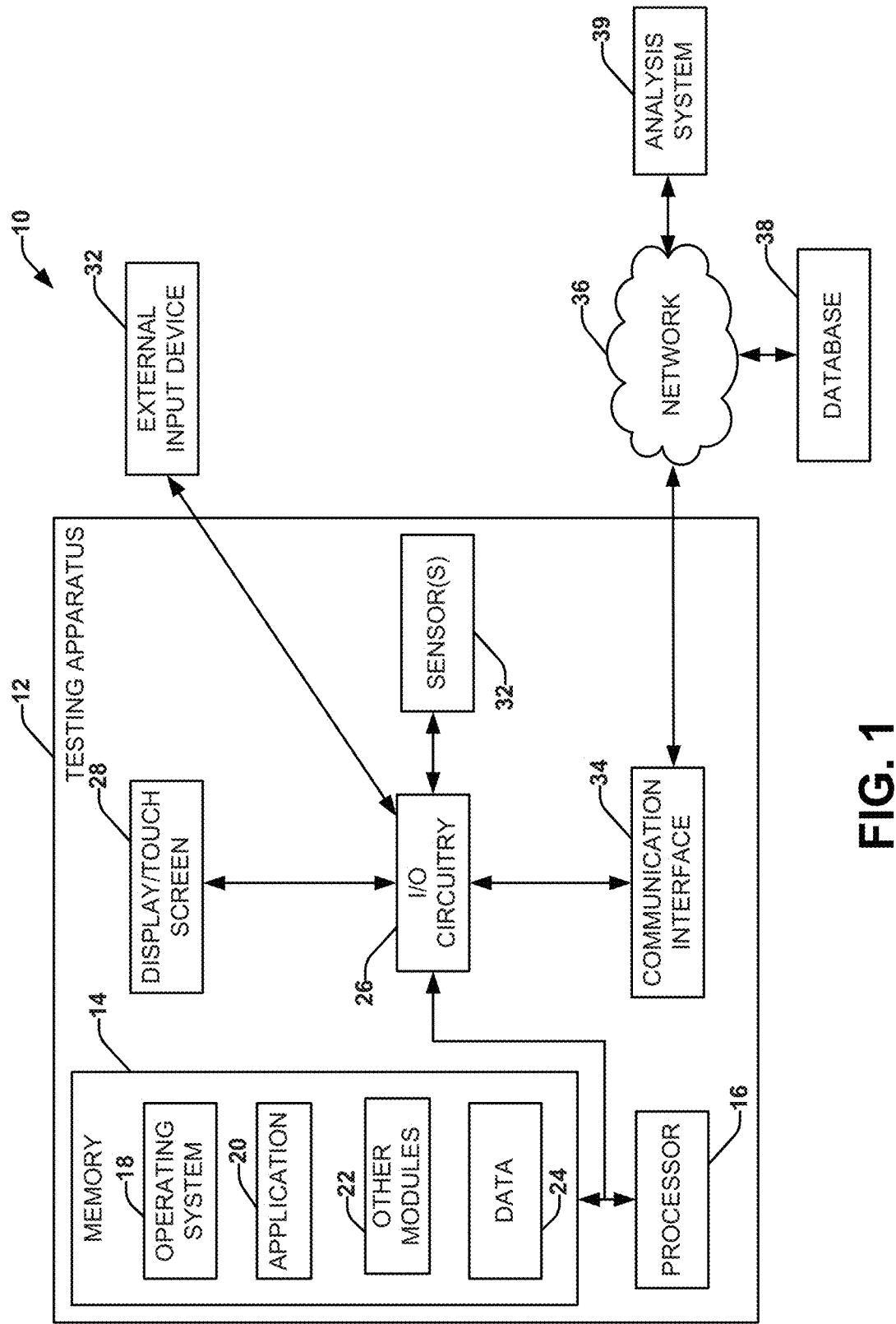
FIG. 1 depicts an example of a system that can implement a performance test to produce results that can be used to evaluate a patient's neurological and cognitive function.

This disclosure relates generally to an apparatus and related method to facilitate testing via a computing device, such as can be utilized to administer a test for the evaluation of cognitive and/or neuromotor function.

By way of example, the apparatus is configured to attach to a tablet computing device for performing diagnostic tests on patients, such as manual dexterity (e.g., peg test), cognitive and/or neuromotor tests. The device can include a moveable platform that provides a test fixture configured to move into and out of physical contact with a surface of the touch screen of the computing device. In some examples, the platform is pivotably connected to the computing device, such as by a test fixture base that attaches the apparatus to the housing of the computing device. An arrangement of receptacles can be formed in the platform to receive and retain contact members (e.g., pegs) within the receptacles as to render the contact members detectable by the computing device while received in the receptacles. For example, the receptacles can be a two-dimensional array (e.g., a grid) of apertures extending through the platform, which has a contact surface to mechanically and electrically connect the device with the computing device.

As a further example, the base can include a housing to surround or otherwise attach to a perimeter portion of the computing device to enable the platform to move into an overlaying contact test position with a predetermined portion of the screen. The platform further may be moved away from the touch screen via the pivot (e.g., greater than about 180 degrees of rotation about the pivot) to a support position in which the platform operates as kickstand to support the housing and the computing device when positioned on a surface (e.g., a table or desk). In some embodiments, the platform may be rotated around the tablet, flush with the other side so as to permit the user to lay the tablet flat on a surface. Thus, the platform, receptacles and touch screen can be employed by a user to perform a manual dexterity test when in the contact position, such as disclosed herein, and enable full access to the touch screen when in the support position.

In some examples, the apparatus includes a hinge that pivotally connects the platform with respect to the test fixture housing, and the hinge can be employed as part of an electrical circuit to provide an electrical path between the receptacles of the platform with an electrical ground of the computing device. When the platform engages the touch screen (e.g., in the test position), the electrical connection that is maintained between the receptacles and the chassis of the computing device enables the computing device (e.g., having a capacitive touch screen) to detect the presence and absence of individual contact members at each respective receptacle—with as well as without human contact with the contact members. As a result, the computing device can be programmed to measure individual peg insertion and removal time (e.g., a part of a manual function and/or neuromotor test).

This disclosure also provides systems and methods that can be utilized to implement a performance test to assess various aspects a patient's neurological and cognitive function. The patient can have a neurological condition that affects cognitive and motor performance, such as multiple sclerosis (MS) or other neurological disorders (e.g., Parkinson's, essential tremor, stroke, concussion, etc.). For example, the performance test can be used to determine the severity of the neurological condition in the patient. Although the systems and methods are described herein with respect to MS and the MS performance test (MSPT), it will be understood that patients with a neurological disorder other than MS can also benefit from the cognitive-motor performance assessment described herein. Such testing can include preprogrammed tests that include use of the apparatus in conjunction with the computing device.

The approach assessing cognitive-motor performance according to the systems and methods described herein can be easily implemented outside of clinical settings by patients themselves or family members. For example, the systems and methods can be executed using a portable computing device, such as a tablet computer or smart phone, which is configured with one or more sensors, including, but not limited to timers, accelerometers and gyroscopes. The portable computing device can be programmed to execute a set of test modules configured to assess cognitive-motor performance, such as a manual function test module, a cognitive processing speed test module, and a movement assessment test module (and other test modules that can be used to assess the cognitive-motor performance). The set of modules can also include a collection module to aggregate test data from the manual function test module, the cognitive processing speed test module, and the movement assessment test module (as well as other test modules that can be used to assess the cognitive-motor performance. The tests can be implemented to measure neurological function and/or neuropsychological function of a subject. For example, the tests can be employed as a test for MS severity as part of a clinical trial or other research protocol, or for patient monitoring for clinical assessment and care.

FIG. 1 depicts an example of a system 10 that can be employed for testing and analysis of one or more patients. The system 10 can include one or more computing apparatuses (also referred to as testing apparatuses) 12 programmed to execute a plurality of tasks based on instructions stored in memory 14. The computing apparatus 12 can be implemented in some embodiments as a portable computer, such as a tablet computer or smart phone. As such, the device may include a display/touch screen 28 that provides a human-machine interface (HMI) that a user, such as a patient, can employ to interact with the computing apparatus 12. As used herein a patient can refer to a living subject (e.g., adult, child or animal) in need of treatment by a physician, physician assistant, advanced practice registered nurse, veterinarian, or other health care provider or the subject may be a healthy subject that is to be tested for other reasons.

In some examples, a user can perform a series of tasks that involve physical interaction between the patient (e.g., using one or more fingers) and the touch screen 28 directly to manipulate one or more graphical objects displayed on the screen. In other examples, user can perform certain tasks through interaction with an external input device 32 that can be communicatively coupled with the system 10 (e.g., via physical or wireless connection with a corresponding port of the apparatus 12). The interaction may involve contact between the external input device 32 and the display 28 or otherwise be responsive to the instructions and/or graphical elements presented on the display. In still other examples, the apparatus 12 can include one or more sensors 30 (e.g., one or more timers, accelerometers, gyrometers or gyroscopes) that can collect data in two or three dimensions responsive to patient movement and interactions during selected tasks. By configuring the testing apparatus (e.g., a tablet computing device) to perform a plurality of different test modules (e.g., stored in memory 14), the over testing process is facilitated for patients as well enables recording a rich set of test data for evaluation of cognitive and neuromotor function for such patients.

As an example, the sensor 30 can include one or more three-axis accelerometers. The one or more accelerometers can be configured to measure acceleration of the apparatus along one or more axis, such as to provide an indication of acceleration (e.g., an acceleration vector) of the apparatus in three dimensions. The one or more accelerometers can measure the static acceleration of gravity in tilt-sensing applications, as well as dynamic acceleration resulting from motion or shock. Additionally, the one or more accelerometers can possess a high resolution (4 mg/LSB) that can enables measurement of inclination changes less than 1.0°, for example. The one or more accelerometers may provide various sensing functions, such as activity and inactivity sensing to detect the presence or lack of motion, direction of motion, the smoothness of motion, and if the acceleration on any axis exceeds a user-defined level. The one or more accelerometers can also sense tapping (e.g., single and double taps) on a surface such as a touch screen as well as sense free-fall if the device is falling. These and other sensing functions can provide output data. An example accelerometer is the ADXL345 digital accelerometer available from Analog devices. Of course other accelerometers could be utilized.

As another example, the sensor 30 can include a three-axis gyroscope (e.g., gyrometer) that can be configured to sense orientation of the device along three orthogonal axes. The gyroscope can provide output data corresponding to orientation of the apparatus 12 along three orthogonal axes. The gyroscope can be implemented as 3-axis MEMS gyro IC, such as including three 16-bit analog-to-digital converters (ADCs) for digitizing the gyro outputs, a user-selectable internal low-pass filter bandwidth, and a Fast-Mode $I^2C$ (400 kHz) interface. The gyroscope 30 can also include an embedded temperature sensor and a 2% accurate internal oscillator. An example gyroscope that can be utilized is the ITG-3200 3 IC available from InvenSense, Inc. Other gyroscopes could be utilized in other examples.

In the example of FIG. 1, the system 10 can include input/output (I/O) circuitry 26 configured to communicate data with various input and output devices coupled to the system 10. In the example of FIG. 1, the I/O circuitry 26 is connected to communicate with the display/touch screen 28, the sensor 30, the external input device 32 and a communication interface 34. For example, the communication interface 34 can include a network interface that is configured to provide for communication with corresponding network 36, such as can include a local area network or a wide access network (WAN) (e.g., the internet or a private WAN) or a combination thereof.

As a further example, the communication interface 34 can send task data and/or analysis data derived from task data to a database 38. The database 38 stores test results data, such as obtained for a plurality of patients (e.g., from one or more health institutions) based on testing using any of the modules disclosed herein. For instance, the system 10 can be programmed to upload and transfer such data to the remote database 38, such as an electronic health record (EHR) for the patient. Such transfer of data can be HIPAA compliant and provided over a secure tunnel (e.g., HTTPS or the like). The transfer of task data and/or analysis data can be automated to occur upon completion of one or more tests. Since the testing is performed via computing device (e.g., tablet), the test results data can also include metadata associated with the testing environment (e.g., time, geographic location, temperature or the like) and the patient (e.g., demographic information, medical history or the like) to facilitate analysis of patient data. For instance, the data provided by the apparatus 12 can further be analyzed by an external analysis system 39. The analysis system 39 can access the database 38 directly (e.g., within a firewall where the database 38 resides or it may access the database via the network 36 via a secure link. Results data acquired for one or modules for different patient cohorts can be aggregated together based on the testing metadata and assessed (e.g., by statistical processing) for a variety of purposes (e.g., clinical research and diagnosis).

A provider may also employ an EHR system or other interface to access the test results stored in the database 38. In this way, statistical analysis of a large patient population can be performed based on data collected from a plurality of different apparatuses, which can be distributed across a state, region, country or even the world. Moreover, since the set of tasks can be performed by patients using a portable computing apparatus (e.g., tablet computer, smartphone) 12 in the absence of a trained healthcare professional, a single provider or team of providers can monitor and service needs of a much larger patient population than would otherwise be possible for traditional MS testing, which typically requires that each patient visit and travel to a testing site for evaluation. Additionally, the approach disclosed herein can provide a patient-centric neurological and neuropsychological performance self-assessment system. By implementing such testing in the system as part of a self-administered testing platform, related scoring and analysis can be generated by the computer automatically because data is collected by such computer, obviating the need for human involvement, and allowing error-free score generation. Further the data collected is objective and as accurate as the sensors and collection system thus providing for more reliable data and statistics. As mentioned above, the analysis and scoring can relate to evaluation of a patient's neurological function, neuromotor function and/or neuropsychological function for the patient.

The computing apparatus 12 can also include a processing unit (also referred to as processor) 16 and memory 14. The memory 14 can include one or more non-transitory memory device configured to store machine readable instructions and/or data. The memory 14 could be implemented, for example as volatile memory (e.g., RAM), nonvolatile memory (e.g., a hard disk, flash memory, a solid state drive or the like) or combination of both. The processing unit 16 (e.g., a processor core) can be configured in the system for accessing the memory 14 and executing the machine-readable instructions. A user may enter commands and information into the computing apparatus 12 through one or more external input devices, such as the touch screen 28 or other user input devices (e.g., a force transducer and stylus apparatus, pegs, microphone, a joystick, a game pad, a scanner, or the like) 32. Such external devices could be coupled to the computing system via the I/O circuitry 26.

By way of example, the memory 14 can store a variety of machine readable instructions and data, including an operating system 18, one or more application programs 20, other program modules 22, and program data 24. The operating system 18 can be any suitable operating system or combinations of operating systems, which can depend on manufacturer and system to system. In some examples, the application programs and program modules for implementing the functions of the test apparatus disclosed herein can be downloaded and/or updated and stored in the memory 14 for execution by the processor 16. The application programs 20, other program modules 22, and program data 24 can cooperate to provide motor and cognitive testing via the computing apparatus 12, such as disclosed herein. Additionally, application programs 20, other program modules 22, and program data 24 can be used for computing an indication of motor, cognitive or a combination of motor and cognitive functions of a patient based on the task data acquired during testing, such as disclosed herein.

As a further example, the application programs 20 can be programmed to implement a battery of tests designed to gather task data for evaluation of a patient's MS condition. For example, the system 10 can include the following test modules programmed to collect data 24, including a manual function test module, a cognitive processing speed test module, a 9 hole peg test, and a movement assessment test module (and other test modules that can be used to assess the cognitive-motor performance). The movement assessment test module can include one or both of a balance test module and a gait assessment module. The data 24 can be analyzed to characterize the patient's cognitive and motor performance, individually or both simultaneously, to provide a quantitative assessment of the patient's MS condition. The data 24 can be analyzed separately for each of a plurality of individual tests to compute a score for each test. Additionally or alternatively, the data 24 for the set of tests can be aggregated to compute an overall score for the patient, which can also be stored in the memory 14 as part of the data 24. The analysis of the data 24 can be performed at the apparatus 12, which is programmed to execute such testing. In other examples, the analysis of the data 24 can be performed remotely, such as by the remote system in response to the data being uploaded from the apparatus 12 to the remote database 38.

Regardless of whether the analysis is performed by the apparatus 12, by the remote analysis system 39 or a combination thereof, since the analysis of the data can be performed by a computer according to test results data, the analysis can provide a more robust characterization of the neurological, neuropsychological and cognitive functioning. As a result, the approach disclosed herein can in turn ascertain more useful information in distinguishing MS or other conditions from excepted norms, and further distinguish severity within a condition and over time for each patient, such as based on a historical analysis of test data over period of time (e.g., one or more years). Additionally, such data can be automatically entered into clinical or research databases, thereby eliminating the need for manual entry of data by a human, and allowing error-free data entry. Further, the data may be saved in a format that makes longitudinal and/or population comparisons more efficient.

Figure 2:
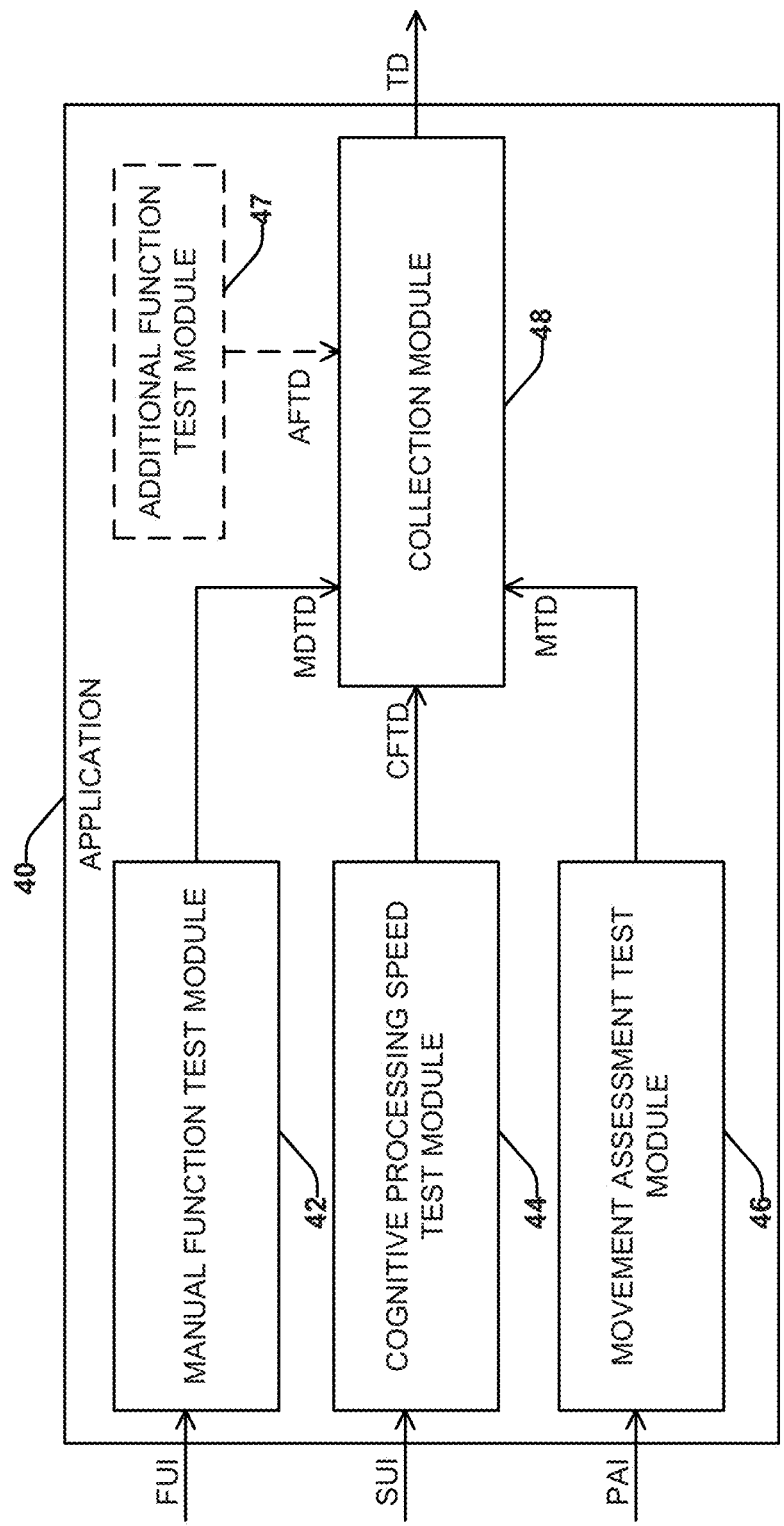
FIGS. 2 and 3 depict examples of applications that can be used to produce the results that can be used to evaluate a patient's neurological and cognitive function.
Figure 3:
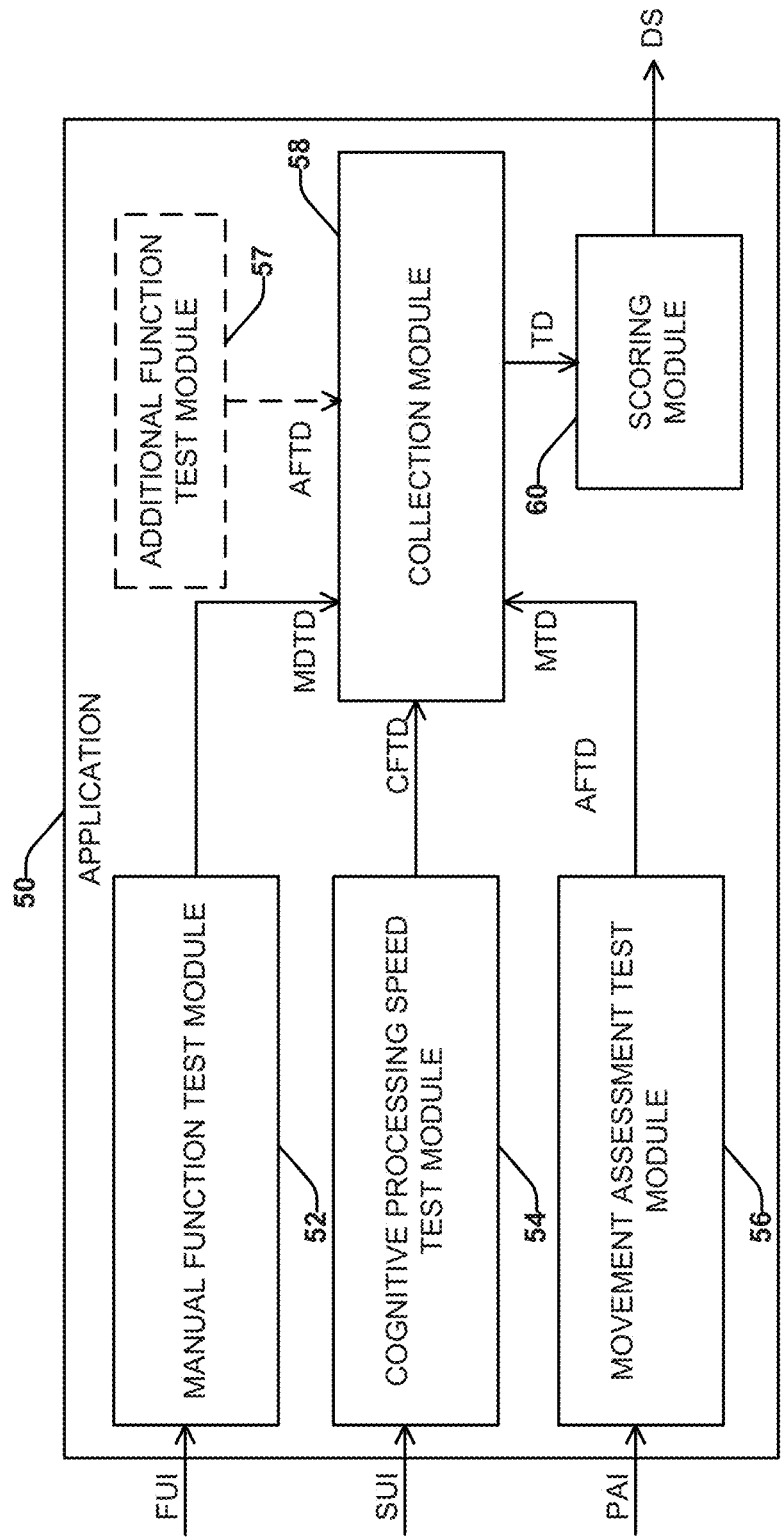

FIGS. 2 and 3 depict examples of respective applications (e.g., stored in memory as machine readable instructions) 40, 50 that can be used to produce the results test data that can be used to evaluate a patient's neurological and cognitive function. Each of the applications 40, 50 can be stored in the memory 14 of FIG. 1 and be executed by the processor 16 of FIG. 1, for example. The applications 40, 50 each include machine readable instructions for an MS performance test (MSPT) and corresponding data that can be programmed to test and evaluate MS status and/or condition of a patient. The applications 40, 50 each include modules that can employ a plurality of discrete tasks that capture corresponding data.

In the examples of FIGS. 2 and 3, the modules include a manual function test module 42, 52; a cognitive processing speed test module 44, 54; a movement assessment test module 46, 56; and a collection module 48, 58. The applications 40, 50 can also include one or more additional function test modules 47, 57. Application 50 also includes a scoring module 60. The manual function test module 42, 52 can evaluate a manual dexterity of a given patient in response to a first set of user inputs (FUI) based on a manual dexterity test executed by the manual function test module 42, 52. The manual function test module 42, 52 can store corresponding manual dexterity test data (MDTD) in the memory based on the first set of user inputs (FUI) indicative of a measure of the given patient's manual dexterity. The cognitive processing speed test module 44, 54 can evaluate a cognitive function of the given patient in response to a second set of user inputs (SUI) based on a cognitive processing speed test. The cognitive processing speed test module can store corresponding cognitive function test data (CFTD) in the memory based on the second set of user inputs (SUI) indicative of the given patient's cognitive function. The movement assessment test module 46, 56 can evaluate center-of-gravity movement of the given patient in response to motion test data (MTD) acquired during a physical activity (PAI) of the given patient. The movement assessment test module 46, 56 can store the motion test data (MTD) in the memory indicative of the center-of-gravity movement of the given patient. The collection module 48, 58 can aggregate test data (TD) based on the manual dexterity test data (MDTD), the cognitive function test data (CFTD) and the motion test data (MTD). The collection module 48, 58 can also aggregate data (AFTD) from any additional function test module 47, 57 into the test data (TD).

The modules of applications 40, 50 can execute tests (also referred to as tasks or trials) that provide outputs that can be utilized to characterize the cognitive and motor state of the patient. The tasks can be programmed to provide and/or coordinate with a graphical user interface (GUI) that displays graphics corresponding to the test. The modules and/or tests can be programmed to collect data in response to user inputs and user interactions during the test. The data acquired during testing can vary based on the test being performed, the test module being executed, and the input devices activated to provide input data. The arrangement of this data and specificity can depend on application requirements and user preferences. Each of the applications 40, 50 can sample active input devices for each test module and test combination, along which related data (e.g., identifying timing, test ID, module ID) to facilitate analysis thereof. The sample rate for a given input source further can vary depending on the input device operating parameters and the information being collected.

Examples of input data that can be collected can include clock data, accelerometer data, gyroscope data, GUI data, UI device data and analysis data. The accelerometer data that can be acquired by sampling an output of one or more accelerometers (e.g., sensors 30 of FIG. 1) to provide an indication of acceleration along one or more orthogonal axes. The gyroscope data can be acquired by sampling an output of a gyroscope (also referred to as a gyrometer). The GUI data can represent user interactions received in response to user input (e.g., as can be made via display/touch screen 28 of FIG. 1) during a respective test. Text and graphical objects can be visualized on a touch screen to instruct the user for performing the various tests for each respective test module. The GUI data can also include graphical and other information that is provided as part of the test and results of the test responsive to user interactions. For example, the results and other information in the GUI data can include timing information obtained during the test, based on a system clock (e.g., of the computing apparatus 12 of FIG. 1) to provide timing information for when user inputs are received. Analysis and meaning attributed to the GUI data depending on the context of the test and test module being executed can also be stored, such as forming part of the GUI data or the analysis data.

The data can also include user input (Up/device data that includes data collected from one or more user input device (e.g., from external device 32 of FIG. 1) during a respective test. For example, the user input device can include a single axis or multi-axis force (torque) transducer that can be utilized to measure a gripping force and associated coordination of a given patient under test. The device can be in the form of a cone-shaped or cylindrical structure to be gripped by the user and includes force transducer to measure the user's gripping force. Other force sensors may include, but are not limited to, the use of springs, strain gauges, piezoelectric materials, and electromagnetic transducers. In some examples, the gripping structure can be utilized to engage graphical objects presented on a display (e.g., a touch screen) via user interactions. The interactions can be detected via the touch screen to provide corresponding GUI data. Thus, it is understood, that the input data recorded for a given test can involve more than one type of data from one or more different input sources. In some example, the input device can also include other sensors (e.g., accelerometers and a gyroscope) such as to provide additional information associated with movement of the gripping structure by the user during the test. Depending on the capabilities of the UI/device data and test requirements, the UI/device data can also include other information relevant to tests or the test environment, such as timing information (e.g., timestamp applied to other data), temperature, altitude, user inputs received via user inputs at the device and the like. Thus, the input data can include a combination of data from disparate and separate devices (e.g., from a gripping device, clock, and from the touch screen) that can be utilized to perform each respective test. The type of movement and interactions requested can vary from test to test.

In the example of FIG. 2, the analysis of the test data (TD) can be performed by a remote analysis system, while in the example of FIG. 3, the analysis of the test data (TD) can be performed by a scoring module 60 and a disability score (DS) can be provided to the remote database. The scoring module 60 can, for example, characterize the cognitive and motor abilities of the given patient based on percentiles of neurological normal function for the manual dexterity test data, the cognitive function test data and the motion test data. It will be appreciated that the scoring function and/or scoring module 60 can use another means to determine the cognitive and motor abilities of the patient with respect to neurological normative values that gives an understanding of the patient's disease state and/or progression.

The scoring module 60 can compute one or more score that can be used to evaluate the cognitive and motor abilities of the patient. The score can be a score for a given test, such as implemented by each of the test modules 52-58. In other examples, the score can be a combined score based on result data collected based on tasks executed for two or more of the test modules. In yet other examples, individual tasks of a given test can also be analyzed to compute a respective score. Each of the scores, regardless of the manner computed, can be stored in memory as part of the analysis data. As mentioned, the scoring function can be programmed to compute each score automatically based on the test data acquired by each respective test module. Scoring may also take into account patient longitudinal date, i.e. data taken during similar tests on the same patient during different sessions over a period of time.

Additionally, since each of the tests can be implemented according to respective test modules, each respective module can be updated independently as new data and testing paradigms might become available. Thus the MSPT application is scalable and extensible.

Figure 4:
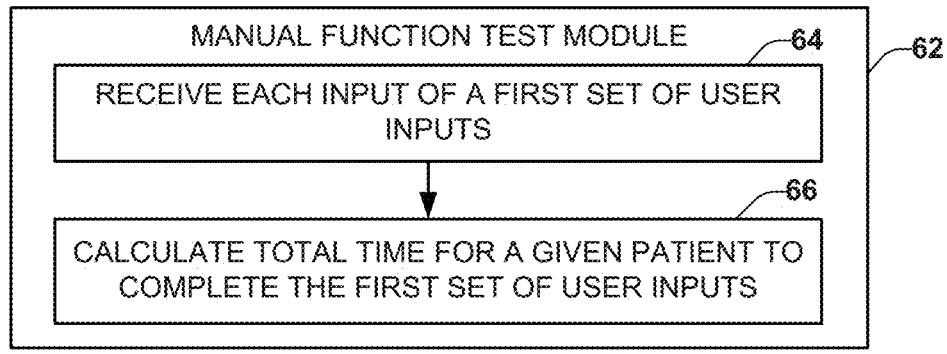
FIG. 4 depicts an example of a manual performance test module that can be used to evaluate a patient's manual dexterity.
Figure 5:
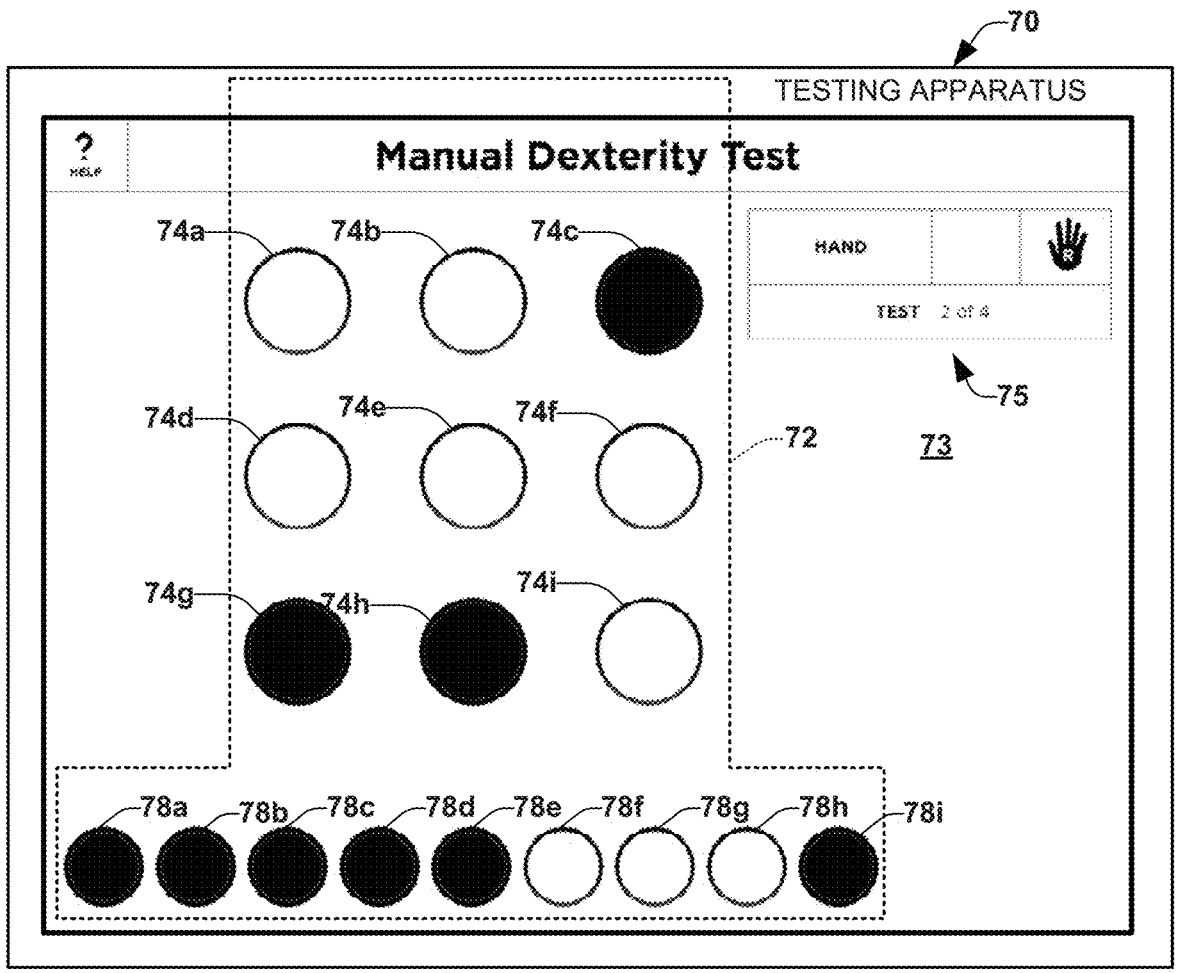
FIG. 5 depicts a schematic example of an upper extremity test that can be used to evaluate a patient's manual dexterity.
Figure 6:
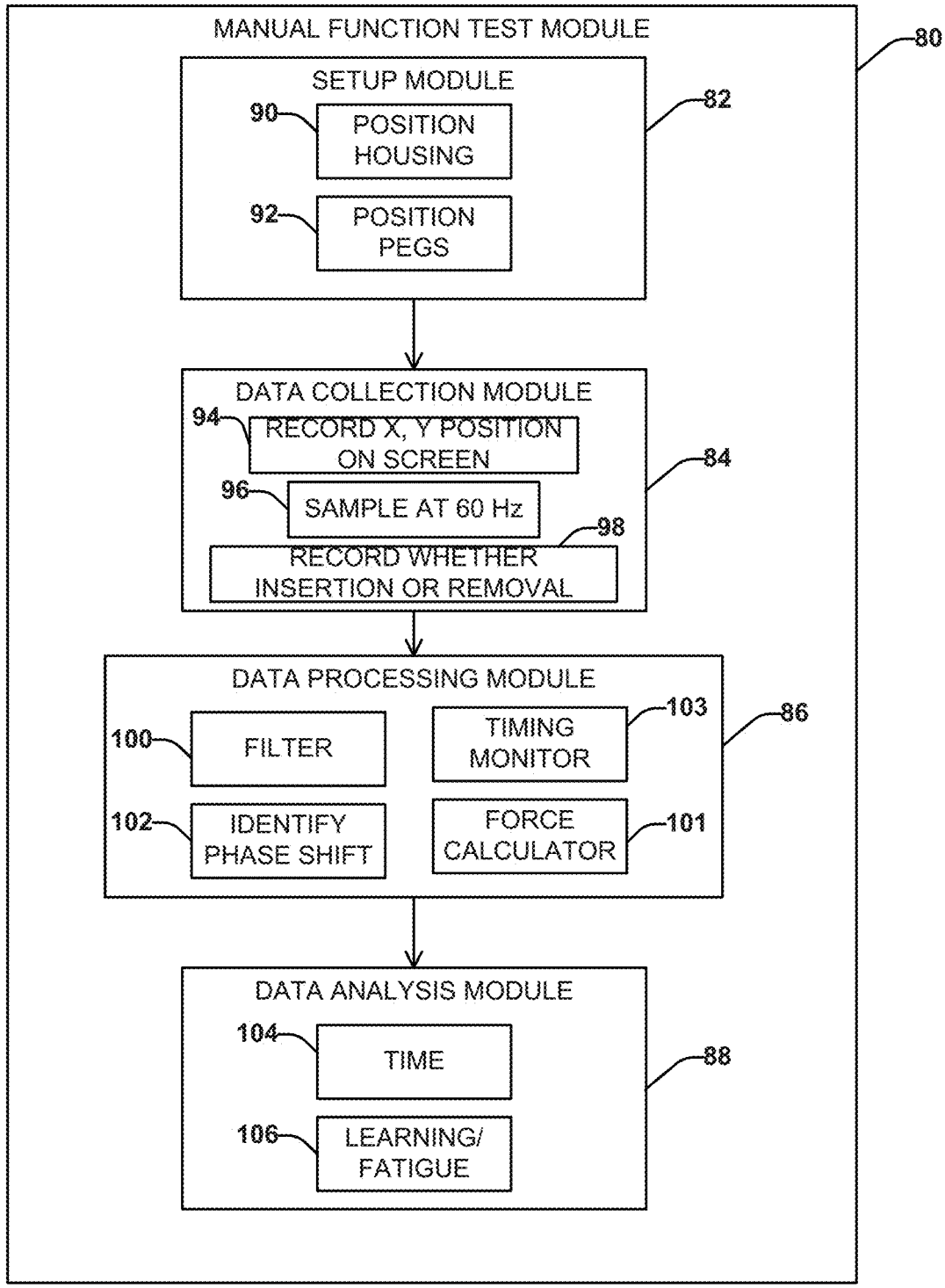
FIG. 6 depicts an example flow diagram demonstrating execution of a manual function test module.

Examples of the manual performance test module that can be used to evaluate a patient's manual dexterity are shown in FIGS. 4-6. FIG. 4 depicts an example of a manual performance test module 62 that can be used to evaluate a patient's manual dexterity. FIG. 5 depicts a schematic example 70 of a standard nine-hole peg test that can be used in conjunction with a touch screen computing device to evaluate the patient's manual dexterity. FIG. 6 depicts an example flow of the execution of a manual function test module 80.

FIG. 4 depicts an example of a manual performance test module 62 that can be used to evaluate the patient's manual dexterity. The user actions can be prompted by graphical and/or audible indicators to initiate the test. At element 64, the first set of user inputs can be received, each in sequence, by the computing device (e.g., a tablet computer or a smart phone). The user inputs can be, for example, a touch by a user's finger or a peg device to a touch screen or the mobile computing device. At element 66, the total time for the given patient to complete the first set of user inputs can be calculated. Other parameters can also be calculated (e.g., force, time for individual tasks, and the like). The total time (and other parameters) can be an output and/or a result of the manual function test module that is part of the test data and scored by a scoring function.

FIG. 5 depicts a schematic illustration of an example implementation of a testing apparatus 70 corresponding to a computer-implemented (e.g., electronic) analog of a nine-hole peg test that can be used to evaluate the patient's manual dexterity. A platform constituting a test fixture 72 can be placed in a test position on a touch-sensitive screen human-machine interface of the testing apparatus (e.g., a tablet computer) 70. As disclosed herein, the test fixture 72 can be pivotably connected to a base of the apparatus 70, which is attached to the computing device, to provide for rotational movement of the test fixture with respect to the touch screen of the computing device between the test position and a support position in which the base is operative to support the base and the computing device. The test fixture 72 includes a plurality of receptacles (or holes) 74a-i for receiving contact members that, when placed in the receptacles while the test fixture is in the test position, enable interaction that is detectable by the computing device even in the absence of direct contact by the user.

The test module (e.g., module 62 or 80) is also programmed to expose a GUI (based on executing preprogrammed MSPT instructions stored in memory of the tablet computer there) on the touch screen 73 for instructing the user during the test. The instructions, including graphical indicators at locations to place the contact members, can be viewable through the receptacles and, in some examples, the test fixture. During testing, the manual function test module (module 62) stores the test data corresponding to user inputs in response to placing the contact members into the receptacles while the test fixture is in the test position during the execution thereof. As mentioned, the test module calculates time values associated with moving respective contact members from the start position to the identified locations on the screen (predetermined locations that align with the receptacles), and stores the computed time values as part of the test data. The contact members can be electrically conductive pegs (e.g., metal pegs) can be removed from starting receptacles 78a-i and inserted into the receptacles 74a-i, and the touch screen interface can detect when the pegs are in contact with the screen.

Examples of testing apparatuses are disclosed herein with respect to FIGS. 24-33. Other examples of a testing apparatus 70 that includes a test fixture 72 and contact members 78 that can be utilized in conjunction with a computing device having a capacitive touch screen are disclosed in the above-incorporated U.S. patent application Ser. No. 14/503, 928 filed Oct. 1, 2014 and entitled OBJECT RECOGNITION BY TOUCH SCREEN, which published as US Pat. Pub. 20150094621 and is incorporated herein by reference.

As disclosed herein, when a contact member (e.g., one of the conductive pegs) engages or otherwise is capacitively coupled with the surface of the touch screen (e.g., a capacitive touch screen) with or without human contact, an electrically conductive circuit is established with the touch-sensitive surface, which includes an electrical path from the contact member to an electrical ground of the computing device. The path can establish a sufficient flow of electrons to enable the electrical characteristics (e.g., capacitance) of the touch-screen to change so that the engagement can be detected even in the absence of human contact. Since the contact member can be detected by the touch-sensitive surface in the absence of contact by the subject, based on the electrically conductive path that is established when a given peg is inserted into a receptacle of the test fixture overlying the touch screen surface, each peg can be detected by the touch screen interface during the test even after it is released by the user.

The manual function test module (e.g., module 62 or 80) can track data related to the nine-hole peg test, including, but not limited to: a position of at least one peg, as well as various times, including the time to complete the nine-hole peg test, a time for peg insertion, a time for peg removal, and/or a force used to insert or remove the peg. Pegs can have any shape such as elongated cylindrical members (e.g., having circular or other cross-sectional shapes). In one example of the test, the test is initiated with the pegs inserted in a row at the bottom of the screen, as demonstrated in FIG. 5. Thus, each peg is detected by the touch screen in the row, resulting in a graphical indicator being displayed on the screen at the location corresponding to each peg. The test ends when the user returns all of the pegs to their starting positions in the row. The timing for moving each peg from the row to one of the nine holes can be computed automatically by the computing device and utilized for assessing the manual dexterity of the user.

In a second example of the test, designed to more closely simulate a traditional 9-hole peg test, the pegs are placed in the center bowl (such may reside between the test receptacles 74 and the starting receptacles 78. The test ends after the pegs have been inserted into and removed from all the wholes and all pegs are returned to the discard area or starting position. Various instructions 75 can be visible through the housing and/or adjacent to the housing (in an uncovered portion of the screen 73) to help guide the user through one or more tests. Instructions can also be rendered as audio that can be provided via speakers (e.g., external speakers of the device or headphones connected to an audio jack).

FIG. 6 shows example flow of the execution of the manual function test module 80 that can quantify manual dexterity during the performance of an upper extremity task. The manual function test module 80 can include a plurality of sub-modules, each of which can include respective functions. As shown in FIG. 6, the sub-modules can include a setup module 82, a data collection module 84, a data processing module 86 and a data analysis module 88. FIG. 6 is described with respect to a tablet computer and the electronic analog of the nine-hole peg test of FIG. 5, but it will be appreciated that other mobile computing devices and/or other types of test can be implemented by the manual function test module 80.

The setup module 82 can facilitate setting up the manual function test, such as can include data 90 specifying that the housing of the nine-hole peg test has been positioned on the touch screen, which can be automatically detected by the touch screen or in response to a user input. Additional data setup data 92 can be provided to specify that the pegs of the nine-hole peg test have also been positioned to their respective starting position, which can be detected automatically or in response to a user input responding to query. In an example, the mobile computing device executing the test module 80 can be a tablet computer (e.g., an iPad tablet computer available from Apple, Inc. or another computer having a touch screen interface). The housing of the test apparatus (housing 72 of FIG. 5; see also FIGS. 24-33) can be positioned on the touch screen such that the holes in the housing can correspond to GUI input points on the touch screen. The pegs can be positioned in a row or in the discard tray or adjacent storage container depending on the test process and configuration of the housing of the testing apparatus. The pegs can be of a diameter smaller than the diameter of the holes, for example, to allow ease of fit, and a length greater than the distance between the touch screen and the holes in the housing, for example, to allow a user to place or remove a peg from the housing.

The data collection module 84 can collect data related to the nine-hole peg test. The data collection module 84 can record a position of each peg (e.g., in the X and Y direction) on the screen 94. The data collection module can sample the touch screen (e.g., via a touch screen API) for the detecting position data 96 representing a location each of the pegs at a predefined sample rate (e.g., about 60 Hz or a higher or lower rate). At each sampling interval, the time associated with any insertion and/or removal event of a peg can be recorded and stored in memory as insertion or removal data 98.

The data processing module 86 can be configured to process input data for subsequent analysis. For example, the data processing module can include a filter 100 to remove noise and artifacts from the collected data. For example, the filter can operate to remove artifacts due to "peg bounce" from data collected from the touch screen. The data processing module 86 can also be configured to identify a phase shift 102 from insertion of the peg to removal of the peg with respect to the test fixture that is overlying the screen.

The data processing module can also include a timing monitor (e.g., clock) 103 to track timing associated with data collected during execution of the test module 80. For instance, the timing monitor 103 can determine factors, such as the total time to complete one cycle of insertion and removal of all 9 pegs. The timing monitor 103 for example can associate a time stamp to all input data, including position data 96 from the touch screen and force information from a force transducer. Additionally, the timing monitor 103 can operate in conjunction with the touch screen interface to indicate a time of insertion and removal of each peg relative to location and removal from the storage tray or home row, and the difference in time to complete the tasks.

In another example, the data collection module 84 can include a force calculator 101 programmed to compute force during a series of tasks for measuring the patient's manual dexterity. The manual function test module 80 can execute instructions, for example, to display a series of GUI objects on a display with which the user is to interact by employing one or more gripping apparatus (e.g., the external user input device 32 mentioned with respect to FIG. 1). As one example, the user can be instructed to select an appropriate gripping device and move an end of the device into engagement with a GUI object displayed on the touch screen. Different shapes and sizes of device can be used or a single generic gripping device can be used. In addition to measuring gripping force during the test, the force calculator 101 can compute other movement and force related information (e.g., force variability) based on the output of a force transducer with which the user interacts and/or interaction with the touch screen. For example, detected data from the force transducer can be communicated to the computer (e.g., via a wired or wireless link) and the force calculator can convert the data in a force measurement. The manual function test module 80 can also record other test information, such as timing based on the timing monitor 103 and other information attributes based on how the user moves the gripping device and how the user interacts with the touch screen during each task.

The data analysis module 88 can analyze the data and create the output data (e.g., MDTD) that is aggregated as part of the test data (e.g., TD) for future scoring. The data analysis module 88 can analyze one or more time parameters 104. The time parameters 104 can include a total time to complete the test, an insertion time for a peg, and/or a removal time for a peg. The time can also be computed as a time difference between any two sequential events. Statistical data (e.g., mean and standard deviation) related to the time values can also be computed and stored in memory. The data analysis module 88 can also measure a learning or fatigue effect 106 with the peg insertion or removal time, such as based on an analysis of how timing changes between subsequent per insertions and/or removals during execution of a given session of the manual function test module 80, such as when the same set of tasks is repeated as part of the manual function test or if different tests are performed.

Figure 7:
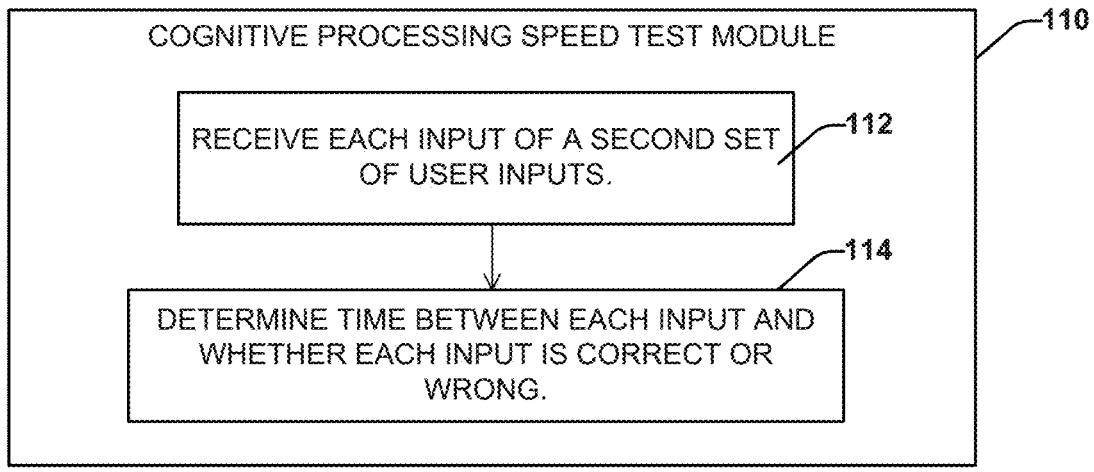
FIG. 7 depicts an example of a cognitive processing speed test module that can be used to evaluate a patient's cognitive processing speed.
Figure 8:
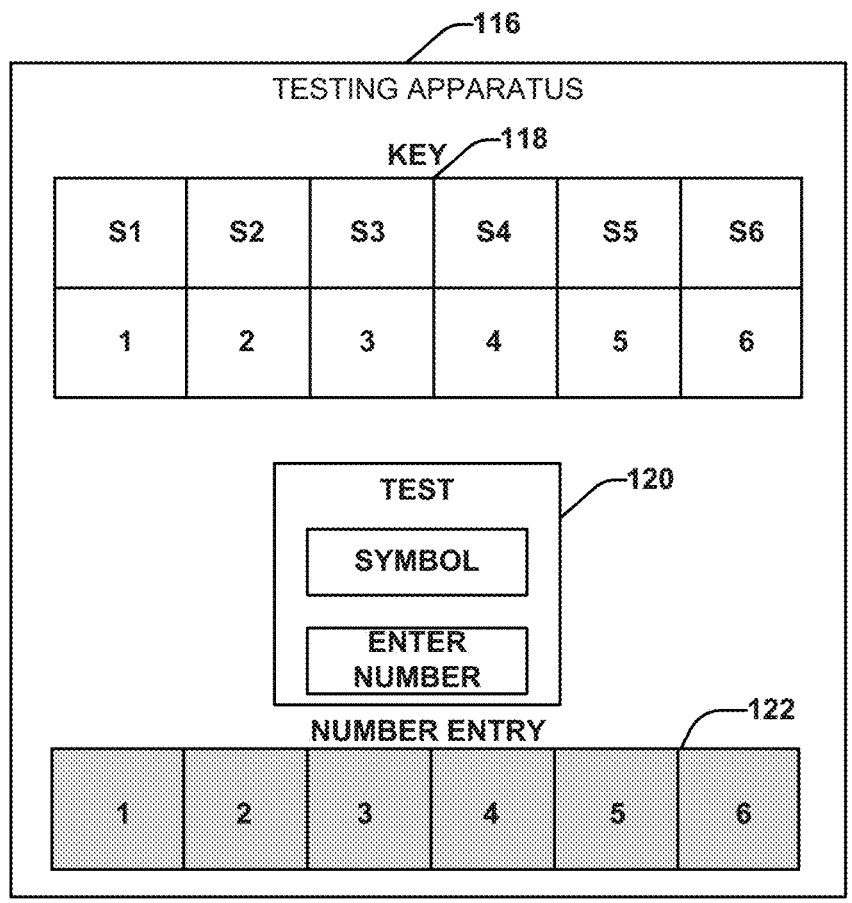
FIG. 8 depicts a schematic example of a cognitive processing speed test that can be used to evaluate a patient's cognitive processing speed.
Figure 9:
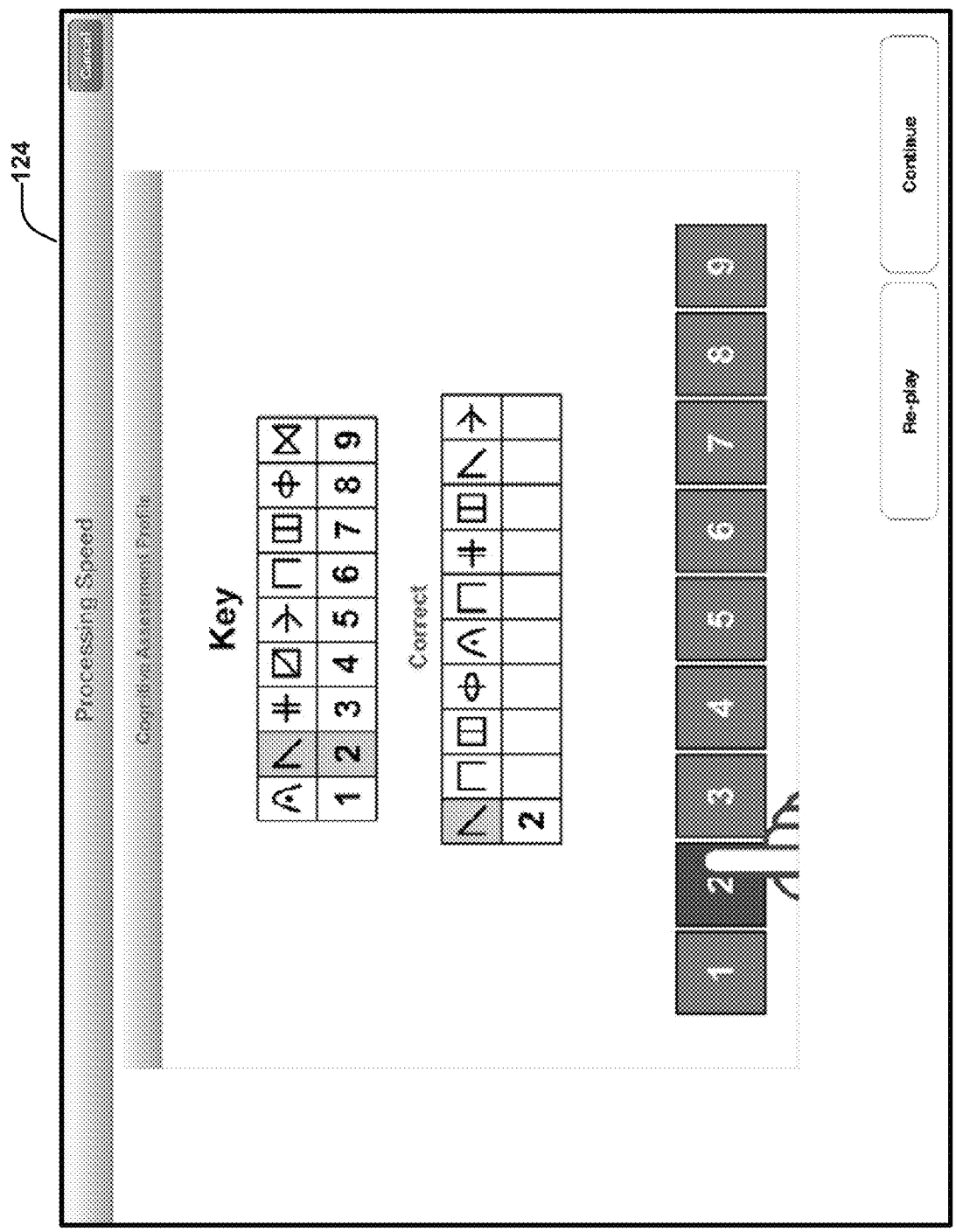
FIG. 9 depicts a screen shot of an example of cognitive processing speed tests that can be used to evaluate a patient's cognitive processing speed.
Figure 10:
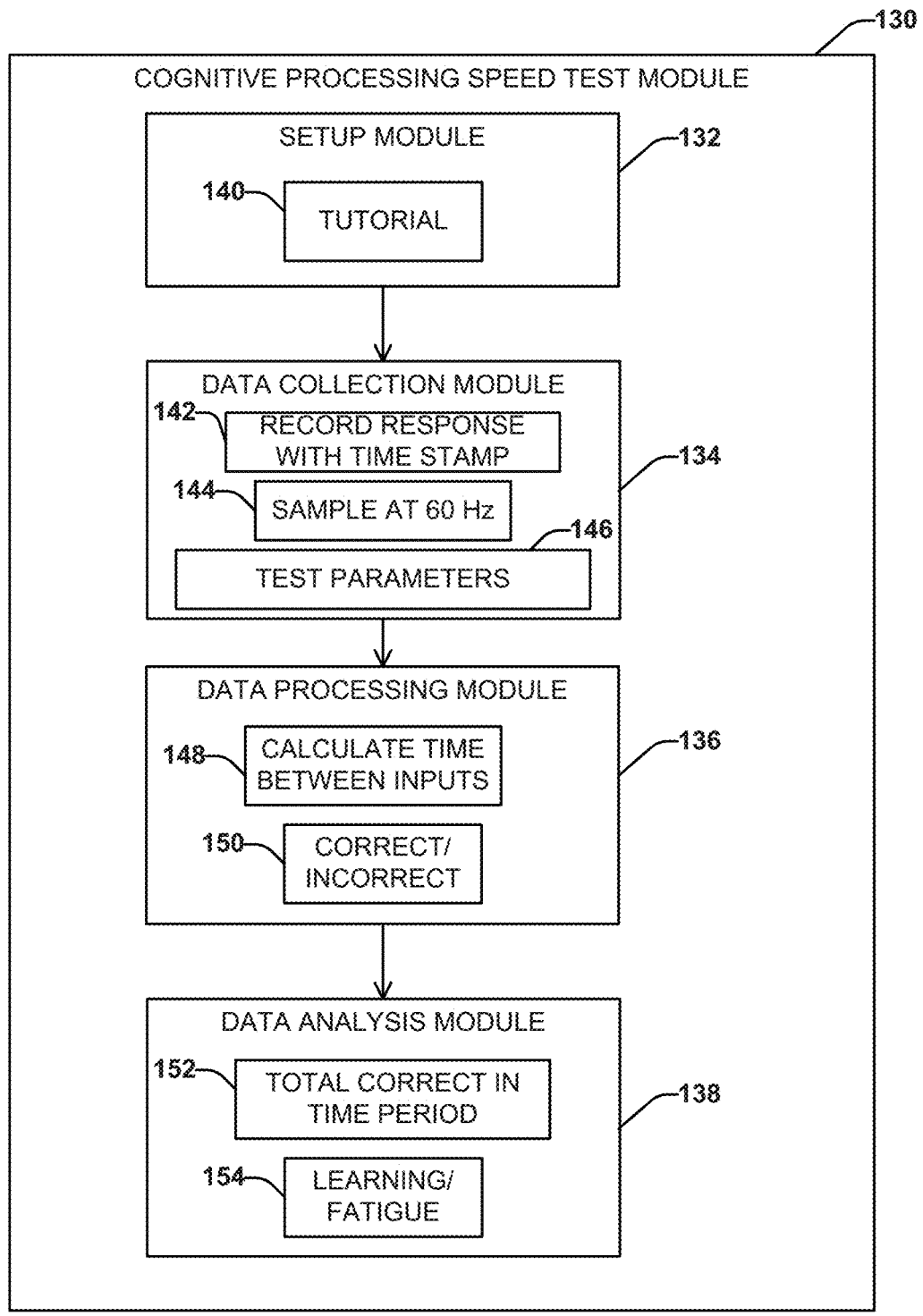
FIG. 10 depicts an example flow diagram demonstrating execution of a cognitive processing speed test module.

Examples of a standard cognitive processing speed test module that can be used to evaluate a patient's cognitive processing speed are shown in FIGS. 7-10. FIG. 7 depicts an example of a cognitive processing speed test module 110 that can be used to evaluate a patient's cognitive processing speed. FIGS. 8 and 9 depict a schematic examples screen shots of interactive GUIs for cognitive processing speed tests 116 and 124, respectively, which can be generated on a touch screen by the cognitive test module to evaluate a patient's cognitive processing speed. FIG. 10 depicts an example flow diagram demonstrating the execution of the cognitive processing speed test module 130.

FIG. 7 depicts an example of a cognitive processing speed test module 110 that can be used to evaluate a patient's cognitive processing speed. The cognitive processing speed test module 110 can include a symbol generator, a key generator, a timing monitor and an analysis function. At element 112, each input of a set of user inputs can be received. The set of user inputs can be received from a user via a user interface, such as a touch screen of a mobile computing device (e.g., a tablet computer or a smart phone). At element 114, the time between each input can be determined. Also at element 114, whether the input is a correct or incorrect response to a prompt can be determined based on the user selection. The time and accuracy can be stored in memory. A score can be determined based on a number of correct responses in a time period for a speed test trail. The number of correct responses during the time period can be aggregated as part of the test data (TD). Additionally or alternatively, the score can be evaluated relative to pre-test data (from a control group, longitudinal patient data, and/or acquired during an un-timed pre-test).

As an example, overall test control can employ the cognitive speed processing test module 54 to implement a test (e.g., using the computing apparatus 12 of FIG. 1) to require that a user repeatedly associate a symbol (e.g., a digit 1-6 of FIG. 8) provided by the symbol generator with a random or pseudorandom key (e.g., S1-S6 of FIG. 9) generated by the key generator. Examples of the different symbols that can be associated with different numbers for the cognitive speed processing test module are shown in FIG. 9, depicts an example screen shot showing a GUI 124 for implementing a processing speed test.

As shown in FIG. 8, the GUI can provide a key (e.g., randomly generated) and a sequence of characters that a user is to match during the testing 118. The randomly generated key can provide random number/signal pairings for each administration. The participant records responses by using the keyboard at the bottom of the screen 122. The middle section of the screen 120 is replaced with a new set a symbols when a response is recorded to the last symbol. The testing can record data indicative of both accuracy and speed for each phase of such testing. The processing speed test demonstrates comparable psychometric properties as the more traditionally used symbol digit modalities test.

The cognitive processing speed test module 110 can also be programmed to provide additional measures beyond simple measure of accuracy. The timing monitor can record the time to complete each task, the test a whole. The timing monitor can also be employed to supply a time base for interactions during the test. For example, if the user is dragging a graphical object (e.g., with a finger or stylus), timing can be utilized to compute acceleration and deceleration effects for such user interactive dragging events. Other cognitive functions tested by the cognitive speed processing test module 110 can include memory recall, attention and mental fatigue.

FIG. 10 depicts an example flow of the execution of the cognitive processing speed test module 130 that can be stored in memory and executed to evaluate a cognitive function of the given patient. The cognitive processing speed test module 130 can include a plurality of sub-modules, each of which can include one or more respective functions. As shown in FIG. 10, the sub-modules can include a setup module 132, a data collection module 134, a data processing module 136 and a data analysis module 138. FIG. 10 is described with respect to a tablet computer and in the context of the corresponding symbol digit modalities test shown in FIGS. 8 and 9, but it will be appreciated that other mobile computing devices and/or other types of tests can be implemented by the cognitive processing speed test module 130. Additionally or alternatively, a score can be determined which can be evaluated relative to pre-test data (from a control group, longitudinal patient data and/or acquired during an un-timed pre-test).

The setup module 132 can present an instructional tutorial 140 on the mobile computing device to establish test competency. The data collection module 134 can collect data related to the cognitive processing speed test. The data collection module 134 can record each response with a time stamp 142, sampling for responsive inputs at a suitable sample rate (e.g., about 60 Hz or a higher or lower rate) 144. The responsive inputs can also be recorded with respect to test parameters 146 (e.g., key and symbol layout). The data processing module 136 can include a time calculator 148 to calculate the time between the individual input responses. The data processing module 136 can also include a function 150 to determine whether each individual input response is correct or incorrect. The data analysis module 138 thus can analyze the data and store corresponding output data (e.g., CPSTD) that is aggregated as part of the test data (e.g., TD) for subsequent overall test scoring. The data analysis module 138 can determine the total score correct in the time period 152. The data analysis module 138 can also be programmed to identify any inter-trial learning or fatigue effect (and correct for these effects). Additionally or alternatively, a score can be evaluated relative to pre-test data (from a control group, longitudinal patient data and/or acquired during an un-timed pre-test).

Figure 11:
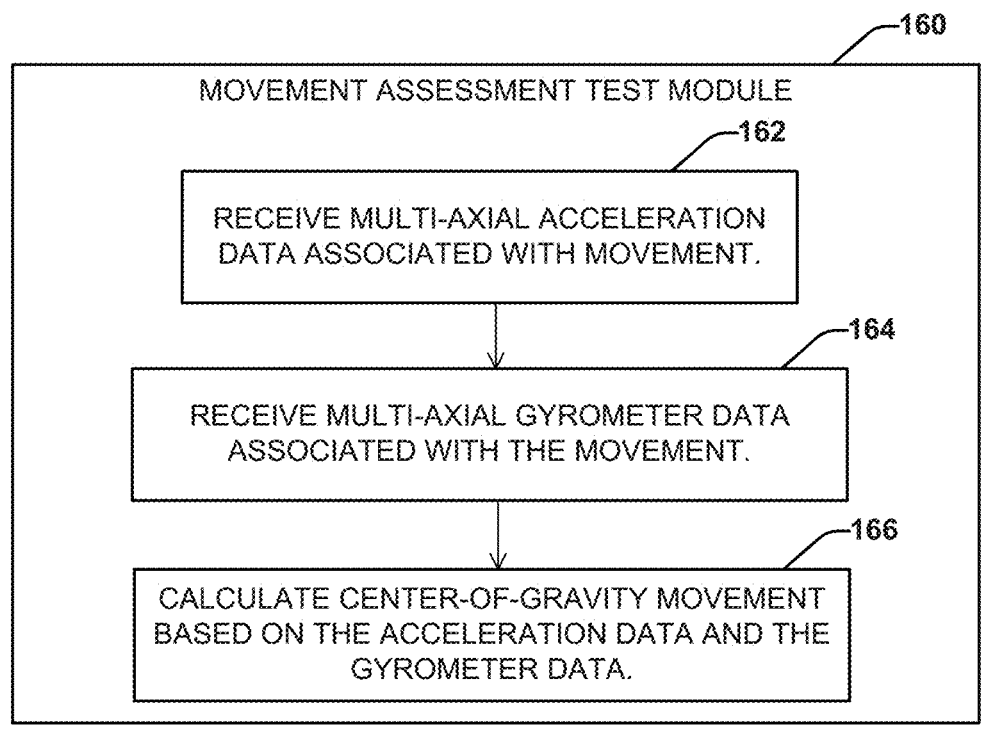
FIG. 11 depicts an example of a movement assessment test module that can be used to evaluate a patient's center-of-gravity movement.
Figure 12:
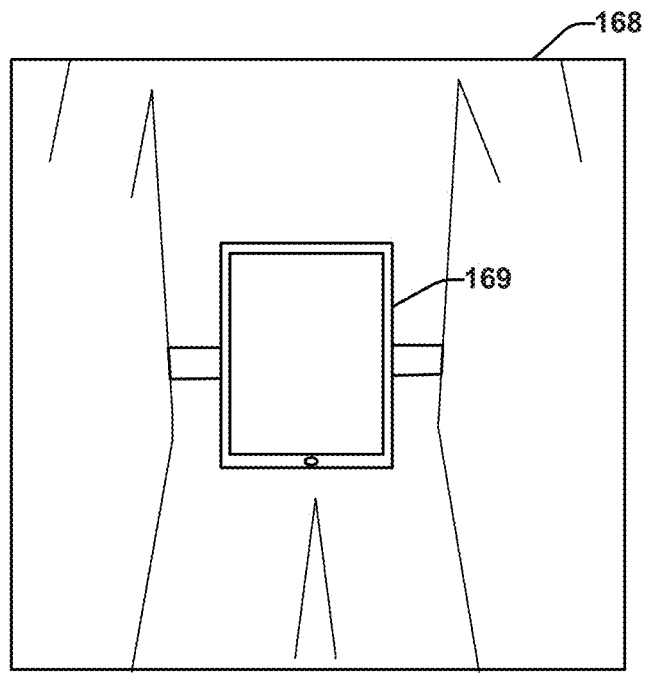
FIG. 12 depicts a schematic example of a mobile computing apparatus that can be attached to a patient for conducting one or more movement assessment tests to evaluate a patient's center-of-gravity movement.
Figure 13:
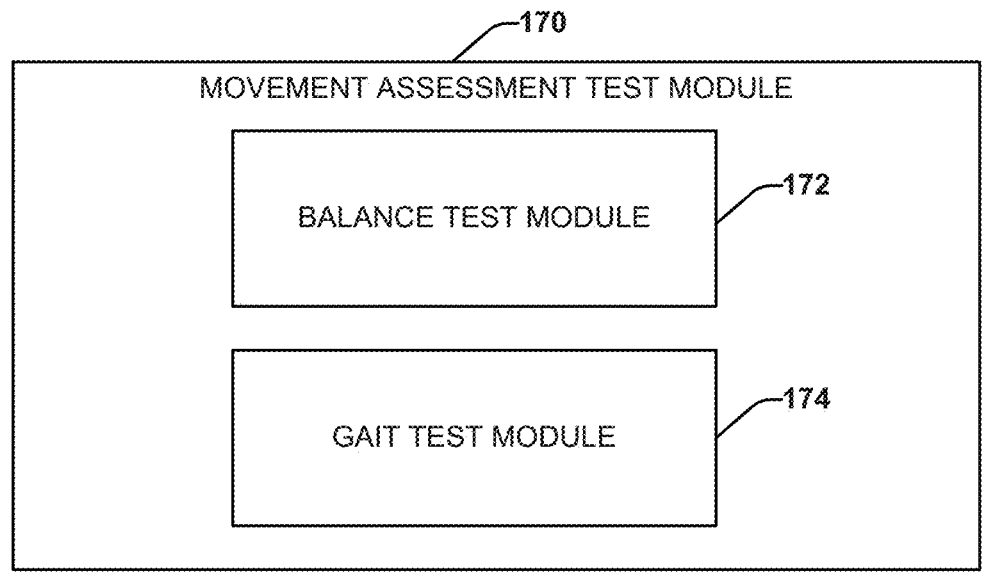
FIG. 13 depicts another example of a movement assessment test module that includes a balance test module and a gait test module.
Figure 14:
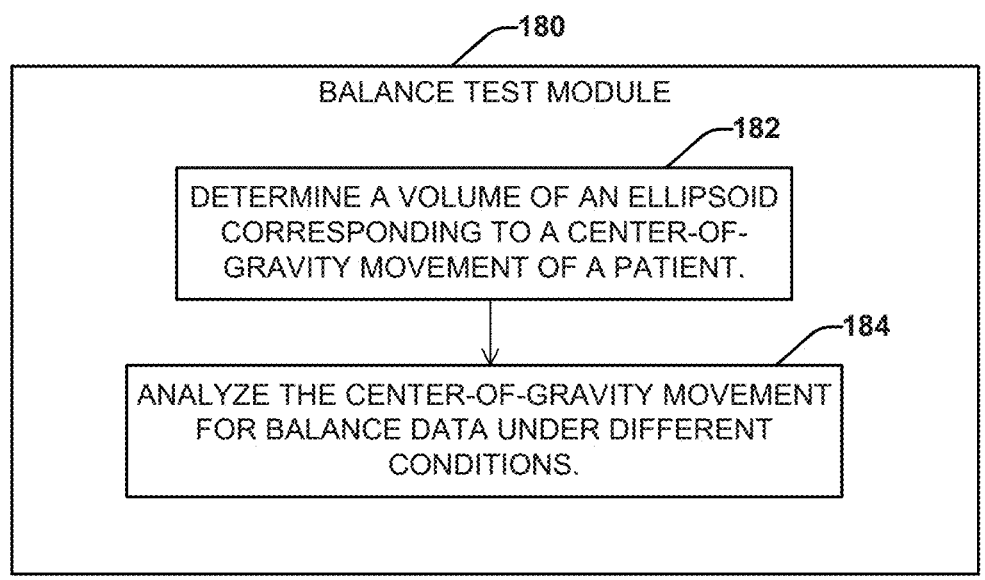
FIG. 14 depicts an example of a balance test module that can be utilized to evaluate a patient's balance based on a center-of-gravity movement.
Figure 15:
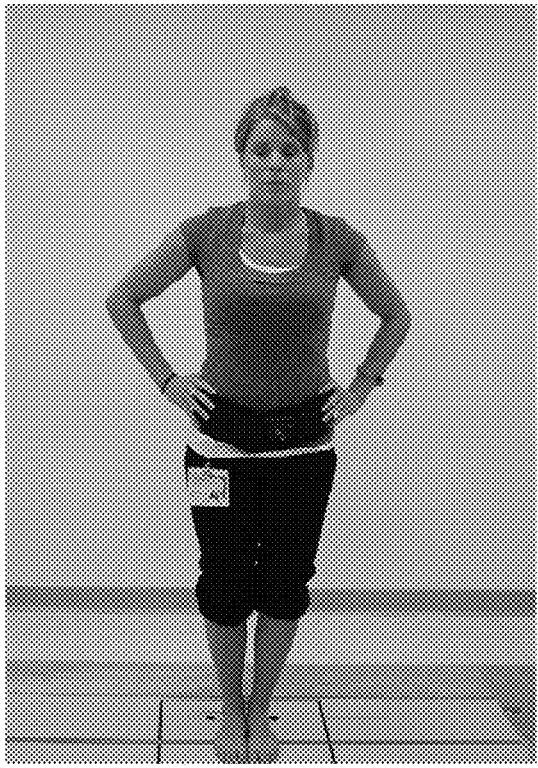
FIG. 15 depicts a screen shot of an example of part of a balance test that can be implemented on a mobile computer to evaluate a patient's balance.
Figure 16:
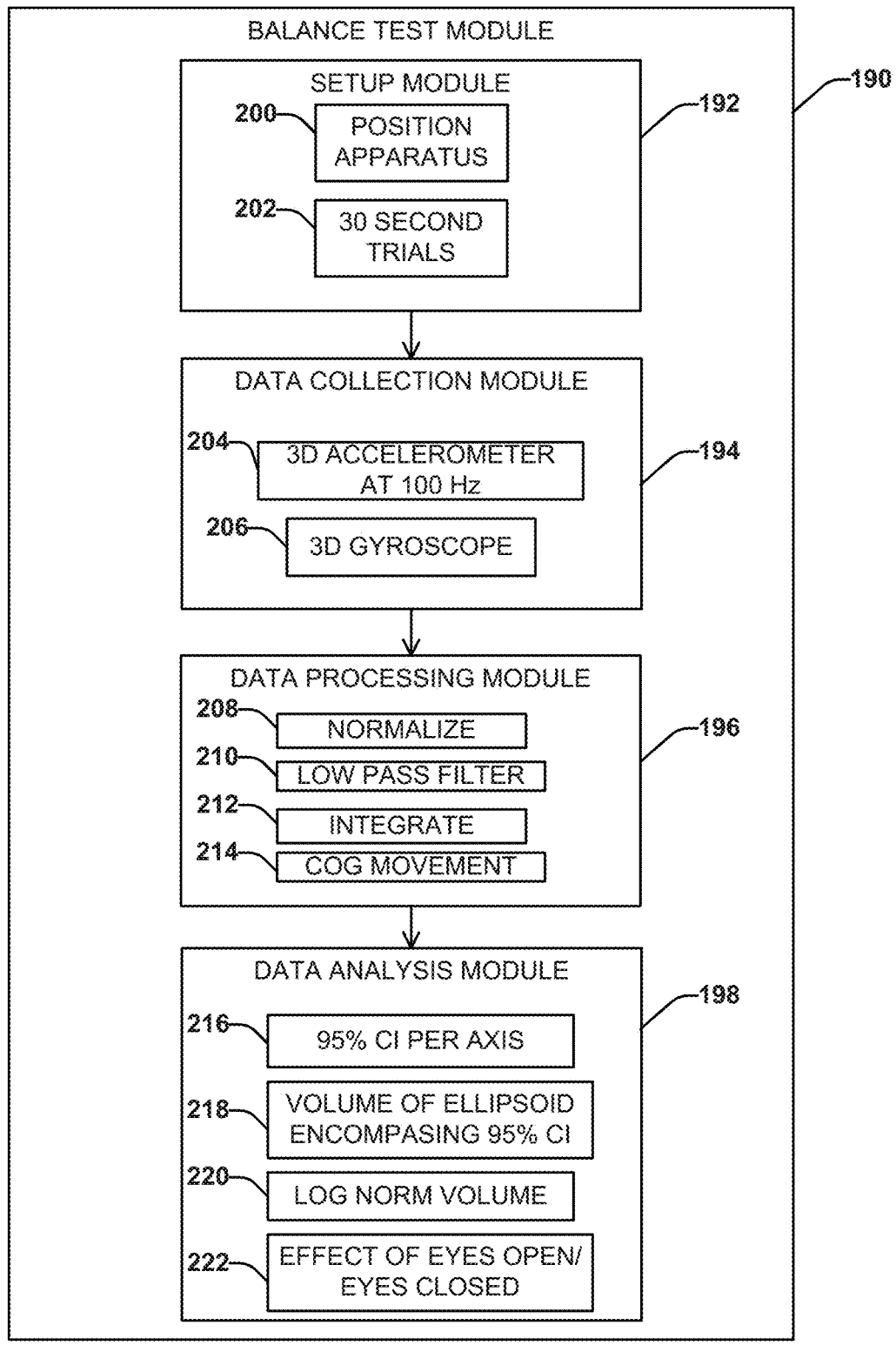
FIG. 16 depicts an example flow diagram demonstrating execution of a balance test module.
Figure 17:
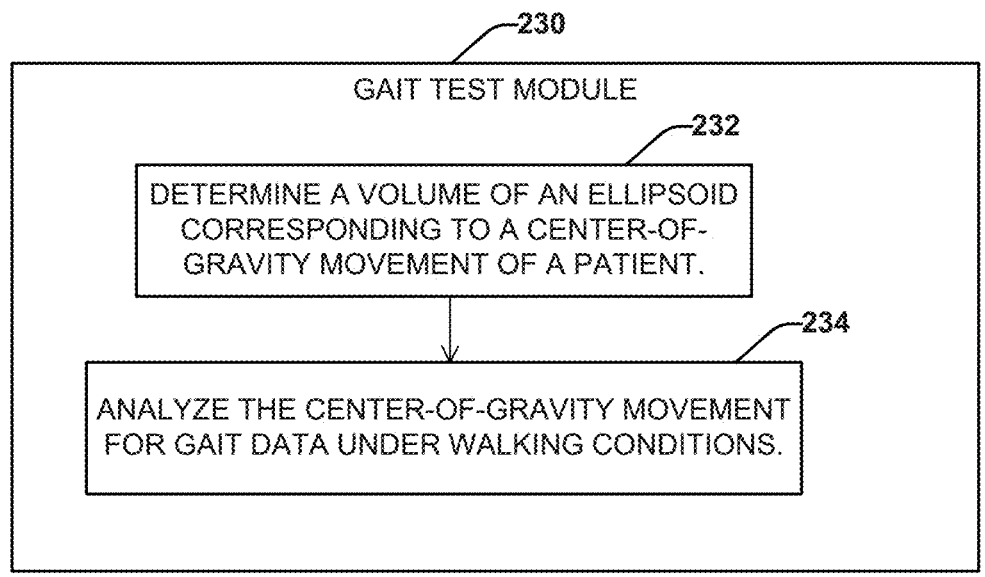
FIG. 17 depicts an example of a gait test module that can evaluate a patient's gait based on a center-of-gravity movement.
Figure 18:
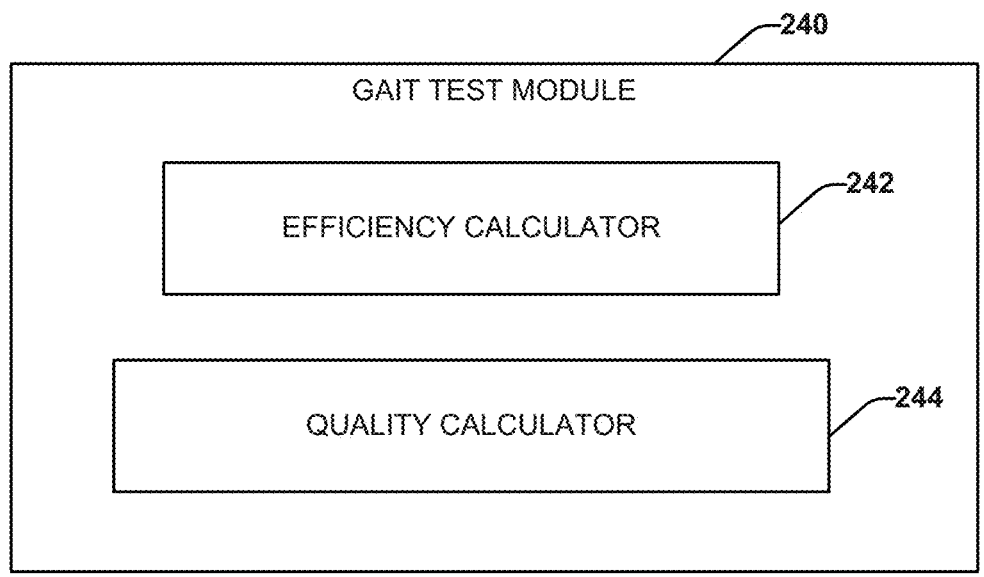
FIG. 18 depicts a schematic example of calculators that can be used by the gait test module to evaluate a patient walking a predetermined distance based on the patient's center-of-gravity movement.
Figure 19:
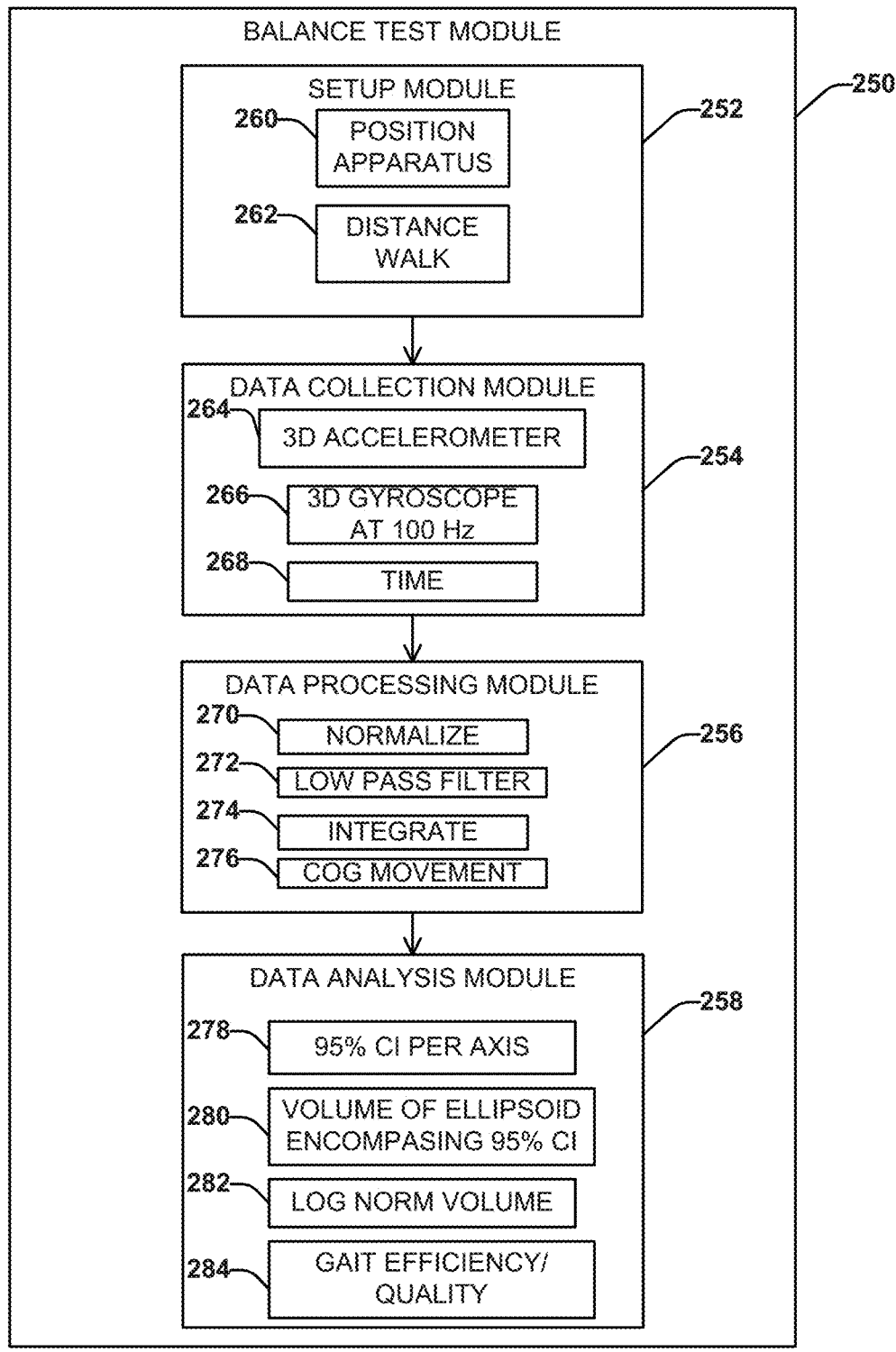
FIG. 19 depicts an example flow diagram demonstrating execution of the gait test module.

Examples of the movement assessment test module that can be used to evaluate a patient's center-of-gravity movement are shown in FIGS. 11-19. FIG. 11 depicts an example of a movement assessment test module 160 that can be used to evaluate a patient's center-of-gravity movement. FIG. 12 depicts a schematic example 168 of a computing device (e.g., mobile computer apparatus) 169 attached to a patient's body for conducting a movement assessment test. FIG. 13 depicts another example of a movement assessment test module 170 that includes a balance test module 172 and a gait test module 174. FIG. 14 depicts an example of a balance test module 180 that can evaluate a patient's balance based on measuring a patient's center-of-gravity movement. FIG. 15 depicts an example 186 of a balance test that can be used to evaluate a patient's balance. FIG. 16 depicts an example flow of the execution of the balance test module 190. FIG. 17 depicts an example of a gait test module 230 that can evaluate a patient's gait based on a center-of-gravity movement. FIG. 18 depicts a schematic example of calculators used by the gait test module 240 to evaluate a patient walking a predetermined distance based on the patient's center-of-gravity movement. FIG. 19 depicts an example flow of the execution of the gait test module 250.

In FIG. 11, the movement assessment test module 160 includes instructions executed to can evaluate a center-of-gravity movement of the given patient in response to motion test data acquired during a physical activity (static or dynamic). The movement assessment test module 160 can receive accelerometer data (e.g., multi-axial accelerometer data associated with a movement 162) and gyrometer data (e.g., multi-axial gyrometer data associated with the movement 164). The accelerometer data and gyrometer data can be sampled from an accelerometer and gyroscope of the computing device and stored in memory during a respective task. The tasks can include a balance task (e.g., provided by the balance test module 172 of the movement assessment test module 170 of FIG. 13) and/or a gait test (e.g., provided by the gait test module 174 of FIG. 13).

To complete the tasks, the patient can wear or hold the portable computing device during a static test (e.g., balance test) or a dynamic test (e.g., gait test). For example, the movement assessment test module 160 of FIG. 11 can be executed by a computing device 169 while attached to the patient, such as demonstrated in FIG. 12. FIG. 12 demonstrates a mobile computing device (e.g., tablet computer or smart phone) 169 fixed on the patient's lower back at or approximating the sacral level. For instance, one or more straps or a belt 171 can be secured to the device and used to hold the computing device 169, for example, on the patient's lower back during execution of the movement assessment test module 160 of FIG. 11. In some further embodiments, the computer device may be attached, for example, with Velcro, snaps, buttons, pockets, elastic material or ties. In some embodiments, the patient may hold the computing device. In some embodiments, the computing device may be attached to the head, back, chest, abdomen, arms and/or legs. This testing configuration can be used for both static testing (e.g., balance test) and/or dynamic testing (e.g., gait test).

In FIG. 11, at element 166, the center-of-gravity movement can be calculated based on the acceleration data and the gyrometer data for the patient. The acceleration data and the gyrometer data can be acquired by one or more accelerometers and gyrometers in the computing device 169. An angular displacement can also be computed based on the gyrometer data, which can be part of the center-of-gravity movement computed by the test module 160 at 166. Movement assessment test module 160 can be programmed to translate the acceleration data and gyrometer data to the patient's center of gravity based on placement of the computing apparatus at a predetermined position during execution of the test module 160.

FIG. 14 depicts an example of a balance test module 180 that can be configured to evaluate a patient's balance based on a static center-of-gravity movement. The balance test module 180 can determine a volume of an ellipsoid in three-dimensional space corresponding to the center-of-gravity movement of the patient, demonstrated as function 182. A center-of-gravity movement during a static balance test corresponds to a lack of balance. The center-of-gravity movement is analyzed for balance data under different conditions, demonstrated as function 184. An example of the different conditions is shown in FIG. 15, which depicts an example screen shot 186 showing a GUI for one type of balance test. In this example, instructions are provided to the user on how to implement the test, such as can include plurality of tests for a predetermined duration. Data from sensors (e.g., one or more accelerometers, magnetometers and a gyroscope) can be collected during each test and a corresponding score can be computed based on such results.

FIG. 16 depicts an example flow of the execution of the balance test module 190 that can evaluate a balance function of the given patient. The balance test module 190 can include a plurality of sub-modules, each of which can include respective functions. As shown in FIG. 16, the sub-modules can include a setup module 192, a data collection module 194, a data processing module 196 and a data analysis module 198. FIG. 16 is described with respect to a tablet computer and the electronic analog of the balance test shown in FIG. 15, but it will be appreciated that other mobile computing devices and/or other types of tests can be implemented by the balance test module 190.

The setup module 192 can position 200 the testing apparatus on the patient's back and configure the time interval for the balance test (e.g., 30 second trials 202). The data collection module 194 can collect data from the accelerometer 204 and the gyroscope 206, each sampled at, for example, 100 Hz. The data processing module 196 can normalize 208 the data for initial apparatus orientation and placement, perform a low pass filter 210 operation on the data, integrate 212 the gyroscope data to resolve angular displacement and calculate time-series center-of-gravity (COG) movement 214 from accelerometer, gyroscope, and angular displacement data. The data analysis module 198 can analyze the data and create the output data that is aggregated as part of the test data (e.g., TD) for future scoring. The data analysis module 198 can determine a 95% confidence interval (CI) of time-series center-of-gravity movement per axis 216; a volume of an ellipsoid that encompasses the 95% CI; a log normalized volume 220; and a per-axis analysis for the effect of eyes open and eyes closed 222 conditions.

FIGS. 17 and 18 each depict examples of a gait test module 230, 240 that can be programmed to evaluate a dynamic condition (e.g., walking speed in a 25-foot walk test) for the patient. The evaluation can be based on the accelerometer data and gyroscope data, which can be used in the computation of a walking speed, a cadence, a stride length, direction, and a variability in one or more of the other computed measures or other variations that might be determined from the acceleration and gyroscope data.

FIG. 17 depicts a gait test module 230 that can determine a volume of an ellipsoid corresponding to a center-of-gravity movement of the patient 232 and analyze the center-of-gravity movement for gait data under walking conditions 234. The analysis can be completed using the components of FIG. 18, an efficiency calculator 242 and a quality calculator 244. The efficiency calculator 242 can compute a measure of gait efficiency for each axis based on the center-of-gravity movement determined along each axis during a gait trial where the patient is walking a predetermined distance. For example, efficiency can be based on a comparison of a measure of movement in the direction of locomotion relative to movement that is not in the direction of locomotion (e.g., anterior-posterior versus medial-lateral motion), such as can be derived from accelerometers and gyrometers attached to the patient during testing. The quality calculator 244 can compute a measurement of gait quality for each axis based on the center-of-gravity movement determined along each axis during the gait trial and based on the time for the patient to walk the predetermined distance. Gait quality, for example can be include efficiency as well as gait symmetry (e.g., a different between left and right side motions) and jerk/accelerations that might occur during testing—also based on measurements from accelerometers and gyrometers attached to the patient during testing. Gait data can be compared against controls, patient populations and longitudinal patient data.

FIG. 19 depicts an example flow of the execution of the gait test module 250 that can include instructions executed to evaluate a dynamic motion task of the patient. The gait test module 250 can include a plurality of sub-modules. As shown in FIG. 19, the sub-modules can include a setup module 252, a data collection module 254, a data processing module 256 and a data analysis module 258. FIG. 19 is described with respect to a tablet computer, but it will be appreciated that other mobile computing devices and/or other types of tests can be implemented by the gait test module 250.

The setup module 252 can ensure that the apparatus is positioned on the patient's lower back 260, establish parameters for a 25-foot walking trial 262, and set a duration dependent on time to complete the 25-foot walk. The data collection module 254 can collect accelerometer data 264 (e.g., three dimensional accelerometer data from the apparatus) and gyroscope data 266 (e.g., three dimensional gyroscope data from the apparatus) both sampled at, for example, 100 Hz. The data collection module 254 can also determine a time for the patient to complete the 25-foot walk 268. The data processing module 256 can normalize 270 the data for initial position (orientation and placement) of the apparatus, low pass filter the data 272, integrate 274 the gyroscope data to resolve angular displacement, and calculate the time-series center-of-gravity movement 276 from accelerometer, gyroscope, and angular displacement data. As an example, the data analysis module 258 can determine a 95% confidence interval (CI) of the time-series center-of-gravity movement per axis 278, determine a volume of ellipsoid that encompasses the 95% CI 280, log normalize the volume 282, and perform a per axis analysis for measure of gait efficiency and quality 284.

Figure 20:
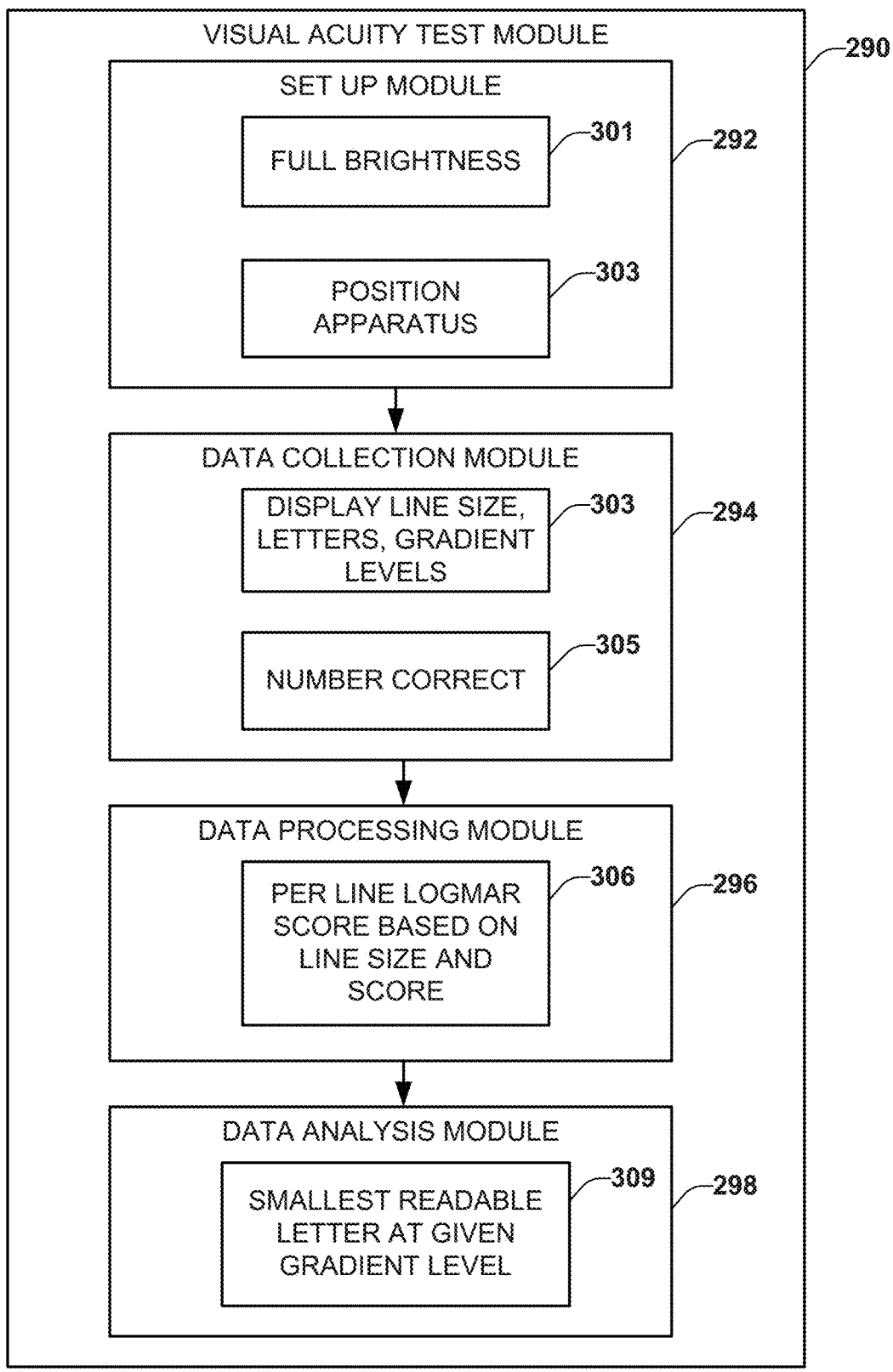
FIG. 20 depicts an example flow diagram demonstrating execution of a visual acuity test module.
Figure 21:
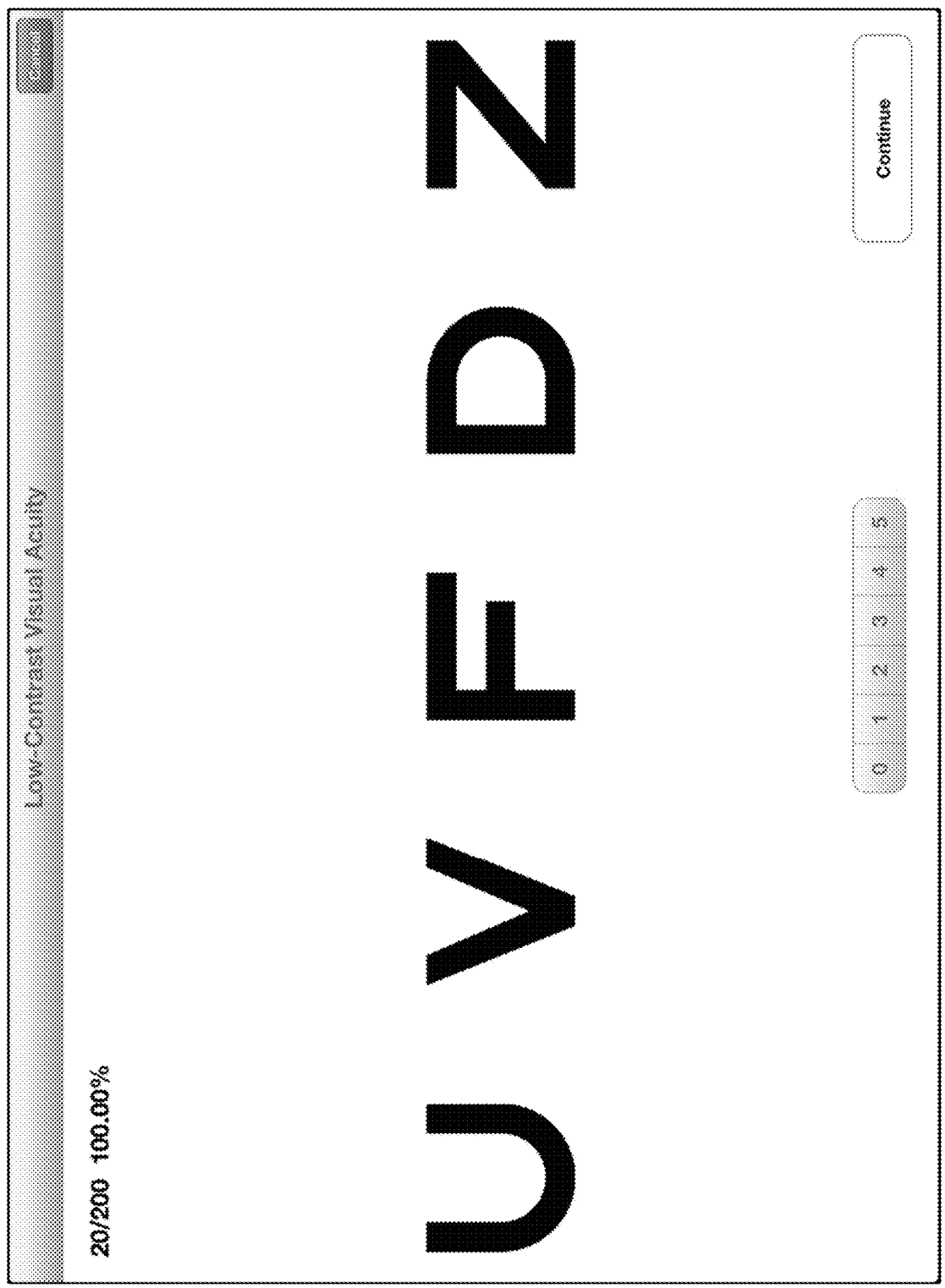
FIGS. 21-23 depict screen shots of examples of part of a visual acuity test that can be used to evaluate a patient's visual acuity and/or sensitivity.
Figure 22:
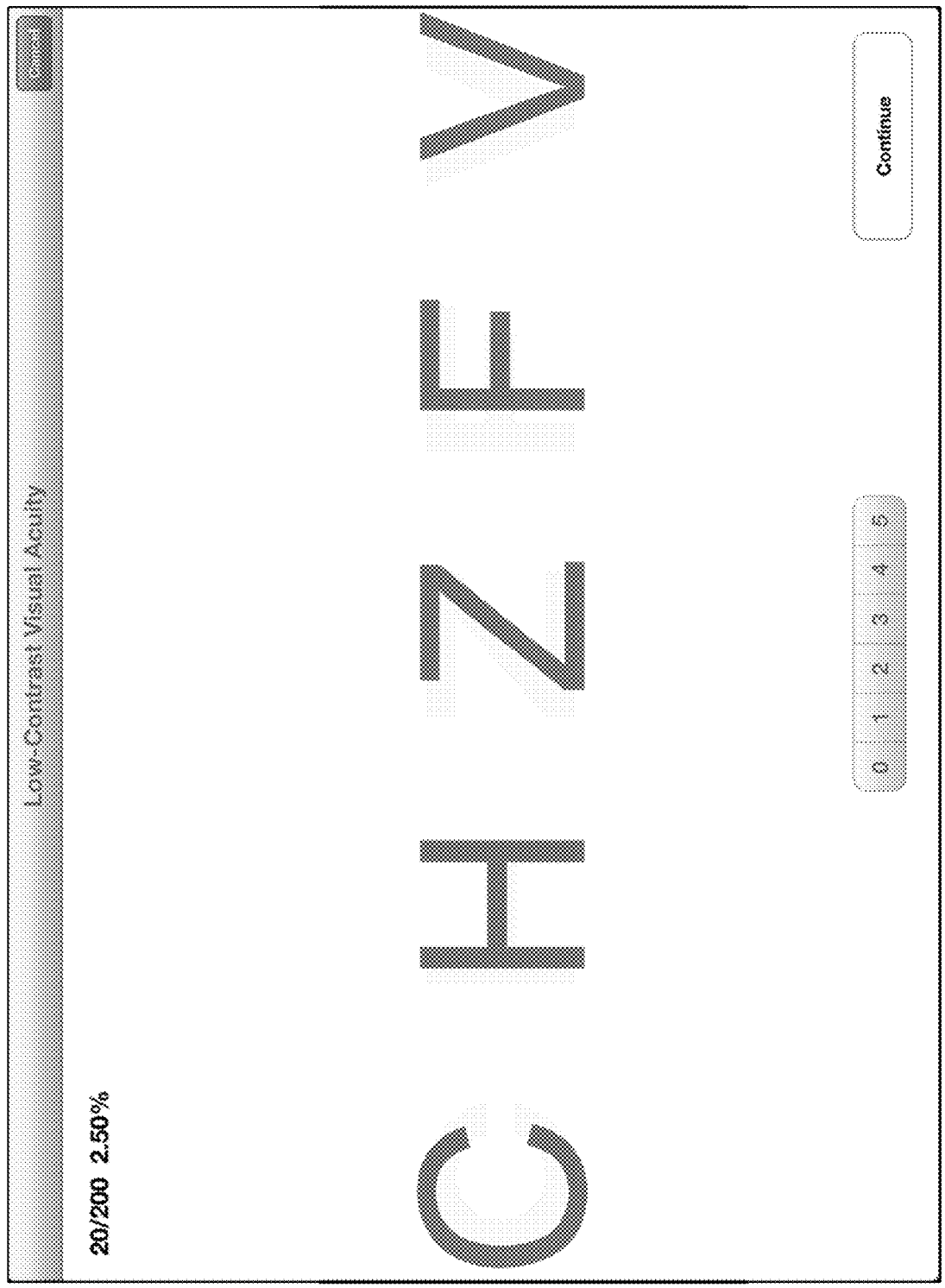
Figure 23:
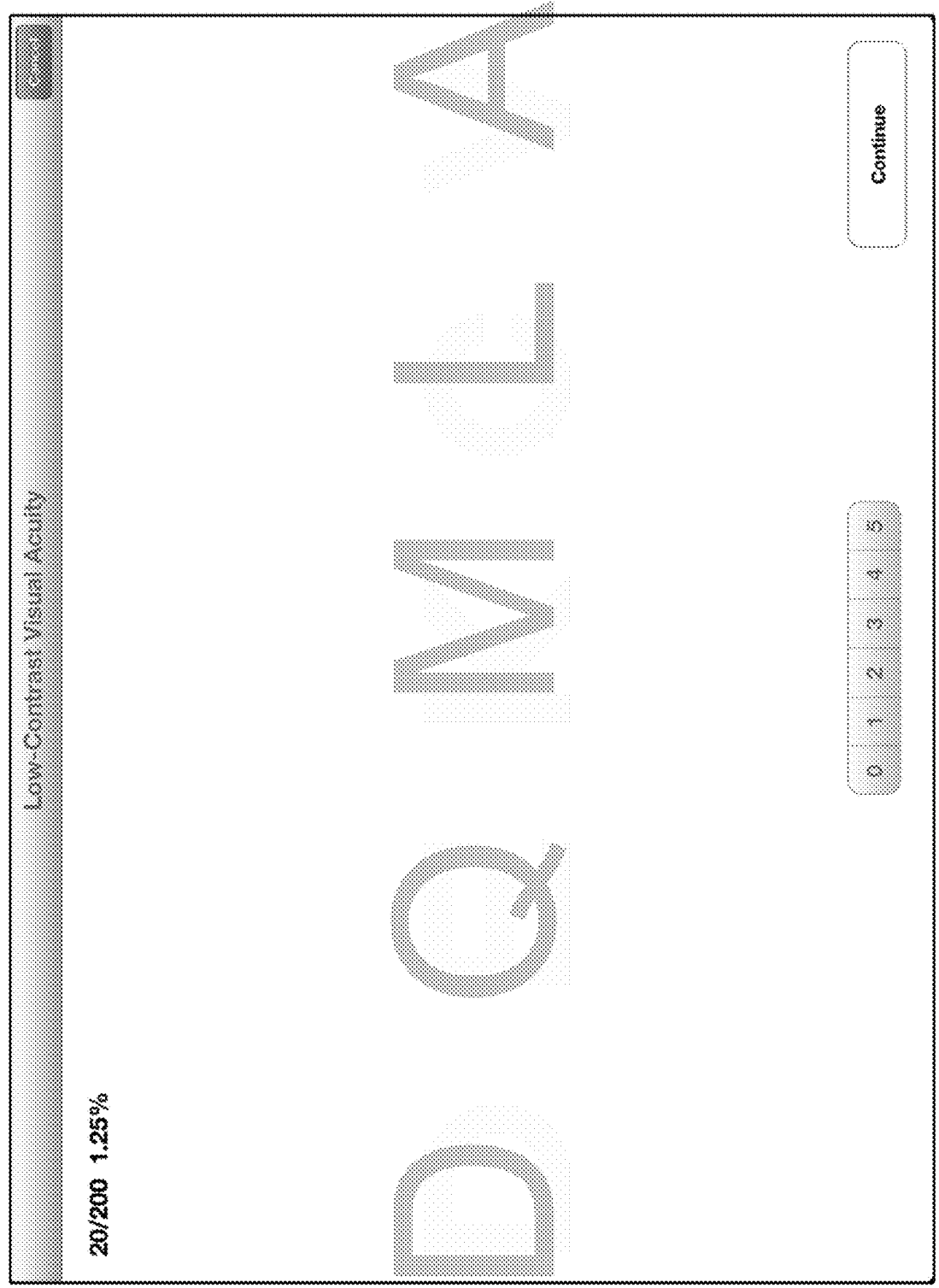

An example of an additional function test module (e.g., module 47 in FIG. 2 or module 57 in FIG. 3) is a visual acuity test module. The visual acuity test module can include instructions programmed to evaluate visual function of the patient in response to user inputs, which can be stored in memory as the UI device data. The visual acuity test module can include a contrast control such as to provide tests for both static and dynamic visual acuity. For example a first part of test can establish baseline static acuity data for the patient. Following the static visual acuity test, the contrast control can vary the contrast in a dynamic manner for a plurality of tests. The data between static and dynamic visual acuity can be analyzed to ascertain an indication of patient visual acuity. The data can include an accuracy level for the test as well as a time to complete each phase of the test. Examples of the visual acuity test module that can be used to evaluate a patient's center-of-gravity movement are shown in FIGS. 20-23. FIG. 20 depicts an example flow of the execution of the visual acuity test module 290. FIGS. 21-23 depict schematic examples of a visual acuity test that can be used to evaluate a patient's visual acuity.

FIG. 20 depicts an example flow that can include instructions executed by the visual acuity test module 290. The visual acuity test module 290 can include a plurality of sub-modules, each of which can include one or more respective functions. As shown in FIG. 20, the sub-modules can include a setup module 292, a data collection module 294, a data processing module 296 and a data analysis module 298. FIG. 20 is described with respect to a tablet computer, but it will be appreciated that other mobile computing devices and/or other types of tests can be implemented by the visual acuity test module 290.

The setup module 292 can set the screen to full brightness 301 and position the apparatus 302 (e.g., 5 feet from the patient at eye level). The data collection module 294 can collect data regarding the line size, letters displayed, and gradient levels 303, as well as the number of correct responses 305 recorded per line (e.g., of a possible 5). The data processing module 296 can determine a per line log MAR score 306 that is calculated based on the line size and the score. The data analysis module 298 can determine the smallest readable letter at a given gradient level 309. The smallest readable letter can be aggregated as part of the total data (TD).

FIGS. 21-23 demonstrate examples of GUIs corresponding to different visual acuity tests that can be implemented for assessing a patient's visual function. In the examples of FIGS. 21-23 different levels of visual contrast are provided, such as can correspond to 100% contrast, 2.5% contrast and 1.25% contrast. Other levels of contrast can be provided for testing a range of visual acuity. The testing can record data indicative of accuracy for the test as well as speed for such testing in response to user inputs indicating each respective letter via a corresponding user input (e.g., keypad or keyboard).

FIGS. 24-29 illustrate an example testing apparatus 300 similar to the testing apparatus 70 of FIG. 5. The apparatus 300 includes a housing portion (e.g., constituting an enclosure) 370 for holding, storing, and transporting a computing device 310 in a compact, reliable manner while being lightweight and cost-efficient to produce. The computing device 310 is programmed with instructions executable (e.g., by one or more hardware processor) to perform one or more test modules to evaluate a patient's condition that affects cognitive and/or motor performance, such as disclosed herein.

The housing 370 can be made by a number of different manufacturing techniques including, but not limited to, CNC, machining, die casting, extrusion, laser-sintering (rapid manufacturing), 3D printing, silicone compression molding, thermoforming or laser-cutting and/or EVA foam molding. The housing 370 can be configured to be ergonomic and user-friendly by, for example, including one or more handles extending from the side(s) of the housing. The housing 370 should be easy and safe to carry while storing and protecting the computing device 310 and test fixture 370. For instance, the housing 370 can be formed from a lightweight, durable material, such as a polymer or plastic. The housing 370 can be translucent and may be clear or colored.

The housing 370 includes a base 332 and a platform constituting a test fixture 330. In the example of FIGS. 24-29, the housing 370 has a rectangular shape and extends from a first end 372 to a second end 374, which ends extend between and space apart opposing edges 375 and 376. The base 332 of housing 370 further can include lower and upper housing portions 381 and 382. The perimeter of the base 332 may be covered in a rubberized material to facilitate gripping and increase the surface roughness along its perimeter. The housing 370 includes an interior space 378 for receiving the computing device 310 therein (see, e.g., FIGS. 28A and 28B). One side of the base 332 includes a notch 380 extending into the interior space 378. The platform 330 is pivotally attached to the base 332 via a hinge 337 positioned within the notch 380 to provide for rotation of the platform 330 with respect to the base 332 and a computing device 310 attached within the base.

The platform 330 is sized and shaped to fit within and be readily accessed through the interior space 378 of the housing 370. This construction enables the platform 330 to pivot away from the computing device 310 and out of the interior space 378 by rotation of the platform in the direction R about the axis 338. As a result, the test fixture 330 is movable relative to the computing device 310 between a testing position overlaying the touch screen within the interior space (see, e.g., FIG. 29) and a support position extending out of the housing to support the apparatus when placed on a surface (see, e.g., FIG. 24). In one example, the platform 330 can pivot through an arc of about 270° relative to the computing device 310 in the direction R. In other embodiments, platform 330 can rotate up to 360° around the hinge to lie flat on the side opposite the screen or interface. The hinge 337 can be a friction hinge, such as biased by one or more springs 347 (see FIG. 27E).

In some examples, such as shown in the example of FIGS. 24, 25, 26A and 26B, the platform 330 may be T-shaped and include a perimeter 334. A contact surface 339 of the platform 330 can be planar and have a shape and size designed to fit within the interior space and onto the screen 312 of the computing device 310 in an overlaying relationship, such as corresponding to a testing position shown in FIGS. 25 and 29 (e.g., for implementing a manual function test).

A plurality of receptacles 340 (demonstrated as 340a and 340b) are formed in the platform 330, such as such as to receive contact members (e.g., pegs) as disclosed herein. The receptacles 340 can be formed as a plurality of apertures extending through the platform 330 to provide access to the screen 312 of the computing device when the platform is in the testing position to provide a corresponding test fixture. The apertures 340 extend as apertures completely through the platform 332 but, in other examples, alternatively can be blind, i.e., not extend entirely through the platform.

The receptacles 340 can be arranged in one or more predetermined patterns according to testing requirements. As shown in the examples of FIGS. 24-29, one set of receptacles 340a are arranged in a 3×3 array of evenly spaced rows and columns. This configuration is similar or identical to the apertures 74a-i in FIG. 5. The receptacles 340a may extend completely through the base 332 or partially therethrough to form receptacles for receiving contact members therein. In some examples, another set of apertures 340b extends into the base 332 and is arranged in a predetermined pattern in an area spaced from the array of apertures 340a. As shown in FIG. 29, 9 apertures 340b are arranged in a linear array along an edge of the platform 330, with recesses extending between adjacent pairs of apertures. The receptacles 340b can be similar or identical to the shaded apertures shown in FIG. 5 and described herein.

By way of further example, the apertures 340a, 340b are configured to releasably receive contact members (e.g., electrically conductive pegs) 400 such as corresponding to the pegs discussed with respect to FIG. 5. The pegs 400 can have any shape but are circular cylindrical in this example. Consequently, the receptacles 340a, 340b are likewise cylindrical. Different cross-sectional shapes of pegs and receptacles can be utilized in other examples, such as for conducting different tests. The apertures 340a, 340b can be countersunk or chamfered to facilitate insertion of the pegs 400.

An interior sidewall of the apertures 340a and 340b can be electrically connected to the housing of the computing device 310 via a corresponding electrically conductive material 342a and 342b that extends from a location within the recesses between receptacles to the hinge 337, which is electrically coupled to electrical ground of the computing device 310. For example, the inner sidewall surface of the receptacles includes electrically conductive material 342 to contact pegs that are insertable therein, which connects the pegs via a corresponding electrically conductive path in the recesses between receptacles, which can include the hinge 337.

Figure 26A:
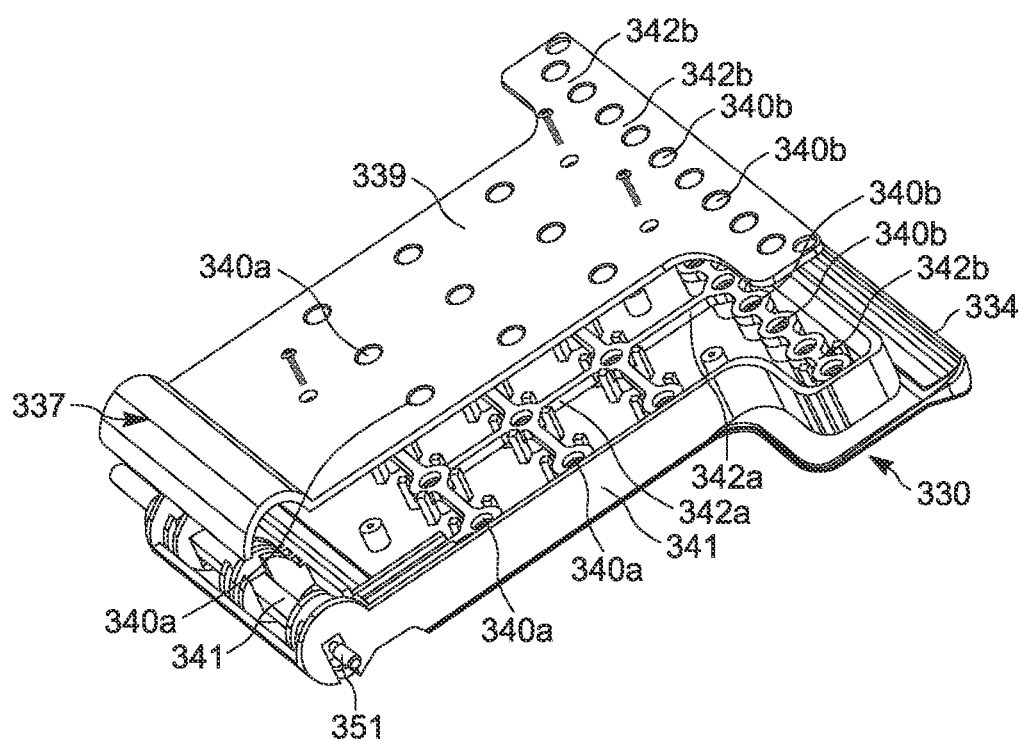
FIGS. 26A and 26B depict a portion of the housing of FIG. 25.
Figure 26B:
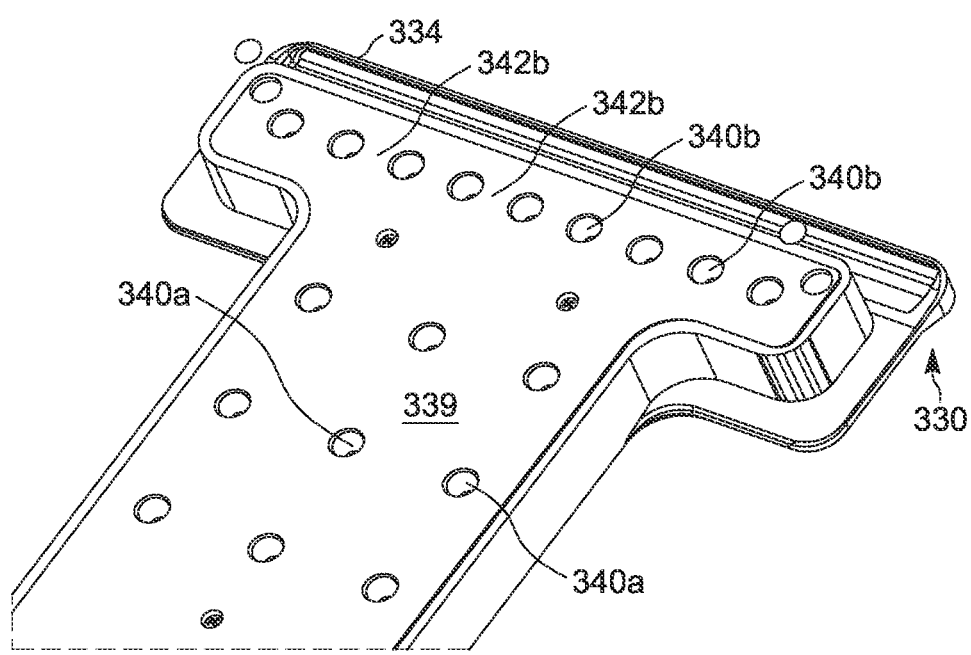

The hinge 337 further can complete an electric circuit between electrically conductive sidewall portions of respective receptacles of the platform 330 and the housing of the tablet computing device 310. As shown in FIG. 26A, for example, electrically conductive material 342 can be provided as a sheet between the contact surface 339 and the opposing surface 341 within the platform 330. The conductive material 342 can include apertures that align with each of the receptacles 340. For instance the conductive material 342 can extend along an interior sidewall of the receptacles 340a and 340b, such as may be in the form of a bushing or other electrically conductive traces can be disposed along an interior sidewall of the receptacles 340. The conductive material 342 can be electrically coupled to the hinge 337 via an arrangement of electrically conductive traces or wires 342a disposed in the body or along a surface of the test fixture platform 330. Since the conductive material at or near the sidewall of the apertures 340A is electrically connected to the housing computing device 310, an electrically conductive path can be established from the touch-sensitive surface, through the sidewall, through the hinge to the housing of the computing device 310.

The hinge 337 also electrically connects the test fixture 330 to the computing device 310, such as by forming part of an electrically conductive path. The path can establish a sufficient flow of electrons to enable the electrical characteristics (e.g., capacitance) of the touch-screen to change so that the engagement between the contact member and the touch screen can be detected even in the absence of human contact. Since the contact member can be detected by the touch-sensitive surface in the absence of contact by the subject, based on an electrically conductive path that is established when a given contact member is inserted into a respective aperture to contact the touch-sensitive surface, each individual contact member can be detected at a corresponding location during the test even after it is released by the user.

FIGS. 27A, 27B, 27C, 27D and 27E illustrate an example of the hinge 337 and other parts constituting the electrical path for connecting the platform 330 to the chassis (electrical ground) of the computing device 310. The hinge 337 includes a portion that is integrally formed with the platform 330 and includes an electrical contact 341 electrically connected to the electrical conductive material 342 within the apertures. A terminal block 343 is positioned within the base 332 of the housing adjacent the notch 380. The terminal block 343 is electrically connected to the computing device 310 via a terminal lead 351 and includes an electrical contact 345. A spring 347 extends between the contacts 341, 345 and electrically connects the same as well as provides mechanical bias for friction during rotation of the platform relative to the base 332. The contacts 341, 345 and spring 347 are aligned along the axis 338 of the hinge 337. Consequently, the spring 347 forms part of the path to establish electrical contact between the electrical ground of the computing device 310 and the test fixture 330. The housing shields the connection therein.

Figure 27A:
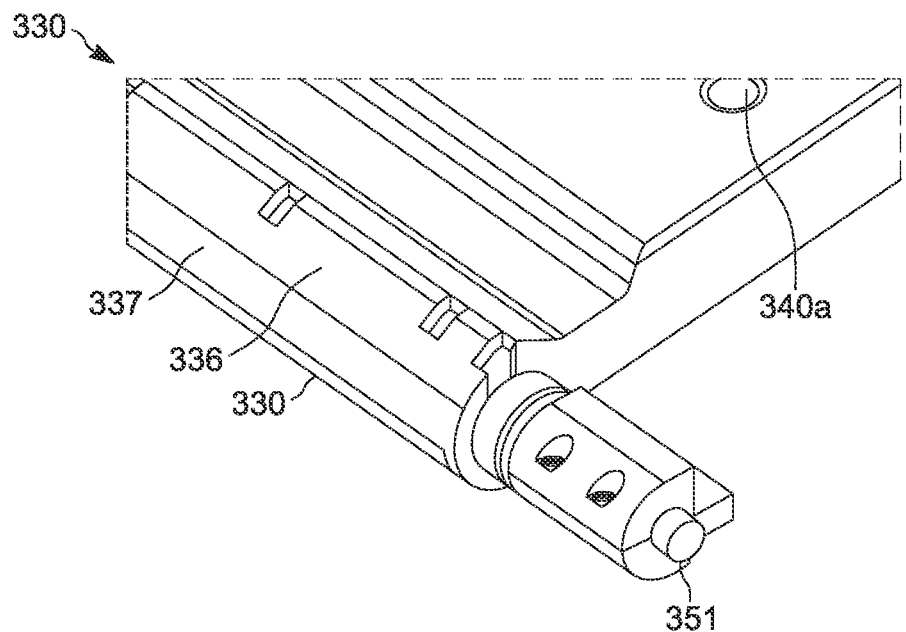
FIGS. 27A-27E depict a hinge mechanism and associated connections for providing the housing.
Figure 27B:
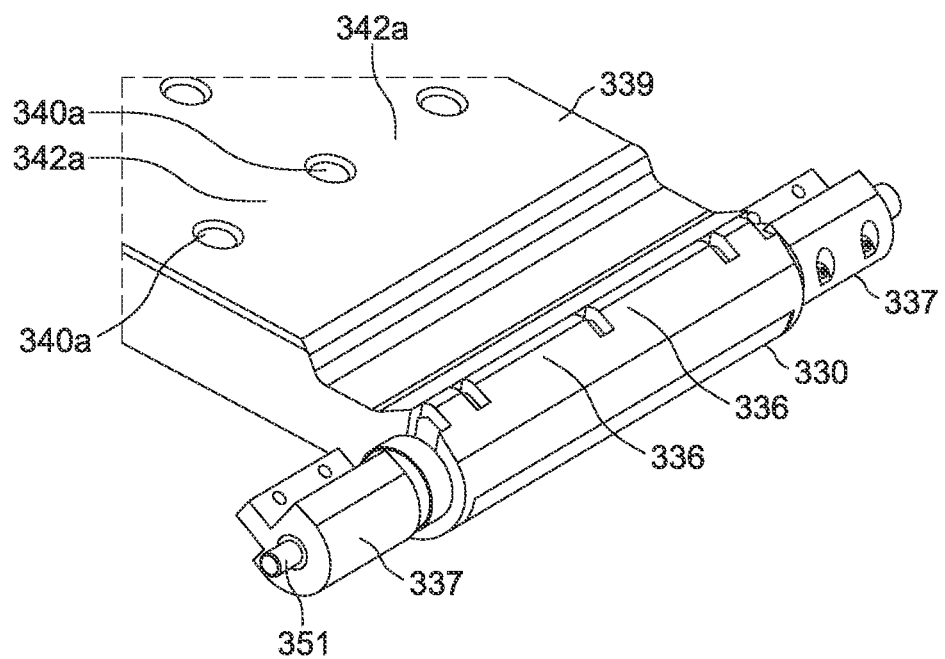
Figure 27C:
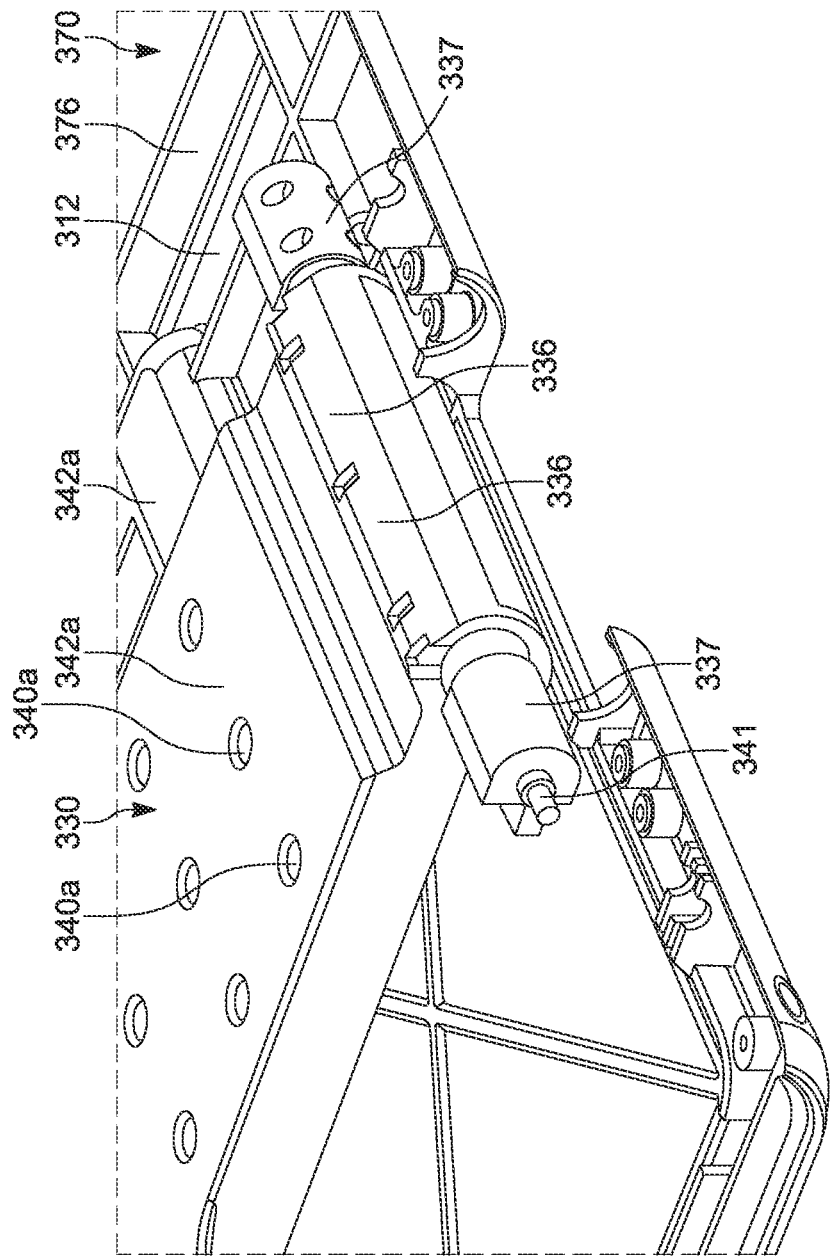
Figure 27D:
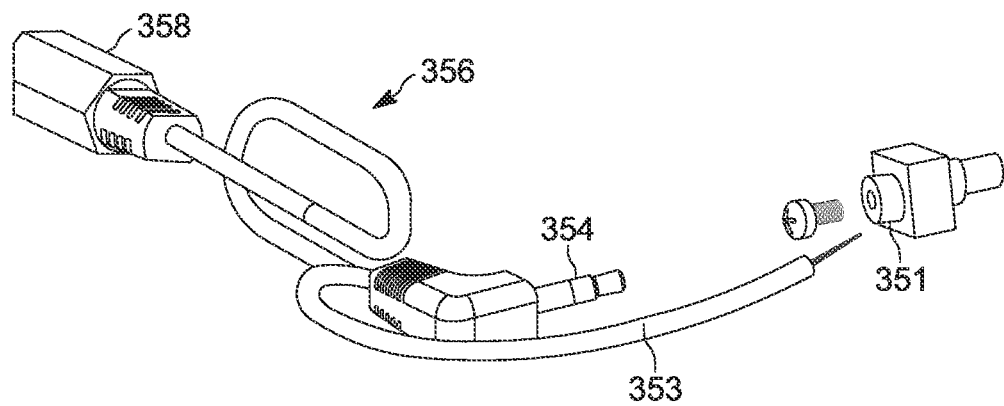
Figure 27E:
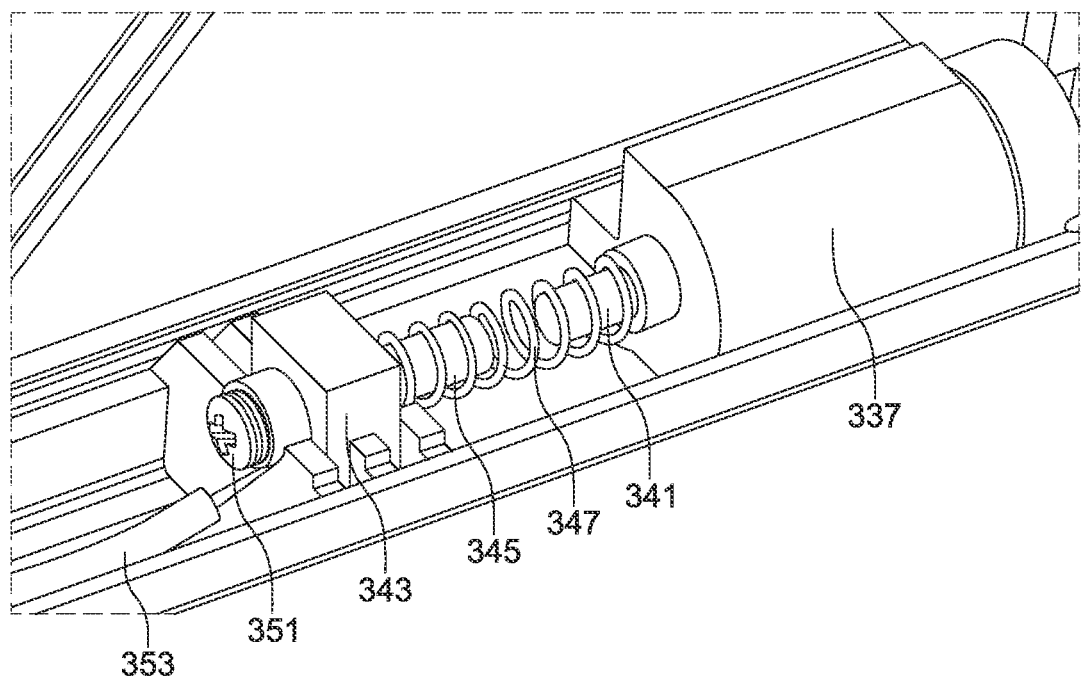

As shown in FIGS. 27D and 27E, an electrically conductive element (e.g., a wire) 353 can be connected to the terminal lead 351 via a screw or other fastener (bolt, conductive adhesive, solder or the like). The conductive element 353 can terminate in a plug 354 that is insertable into an audio or other jack of the computing device 310 for completing the path to electrical ground of the device (e.g., the jack includes a device ground connection). In some examples, the conductive element 353 can include a splitter 356 can be used to provide an additional auxiliary jack 358 to enable use of the audio jack while the testing apparatus is in use. The jack 358 thus can be exposed and accessible from external to the housing during operation.

Figure 28A:
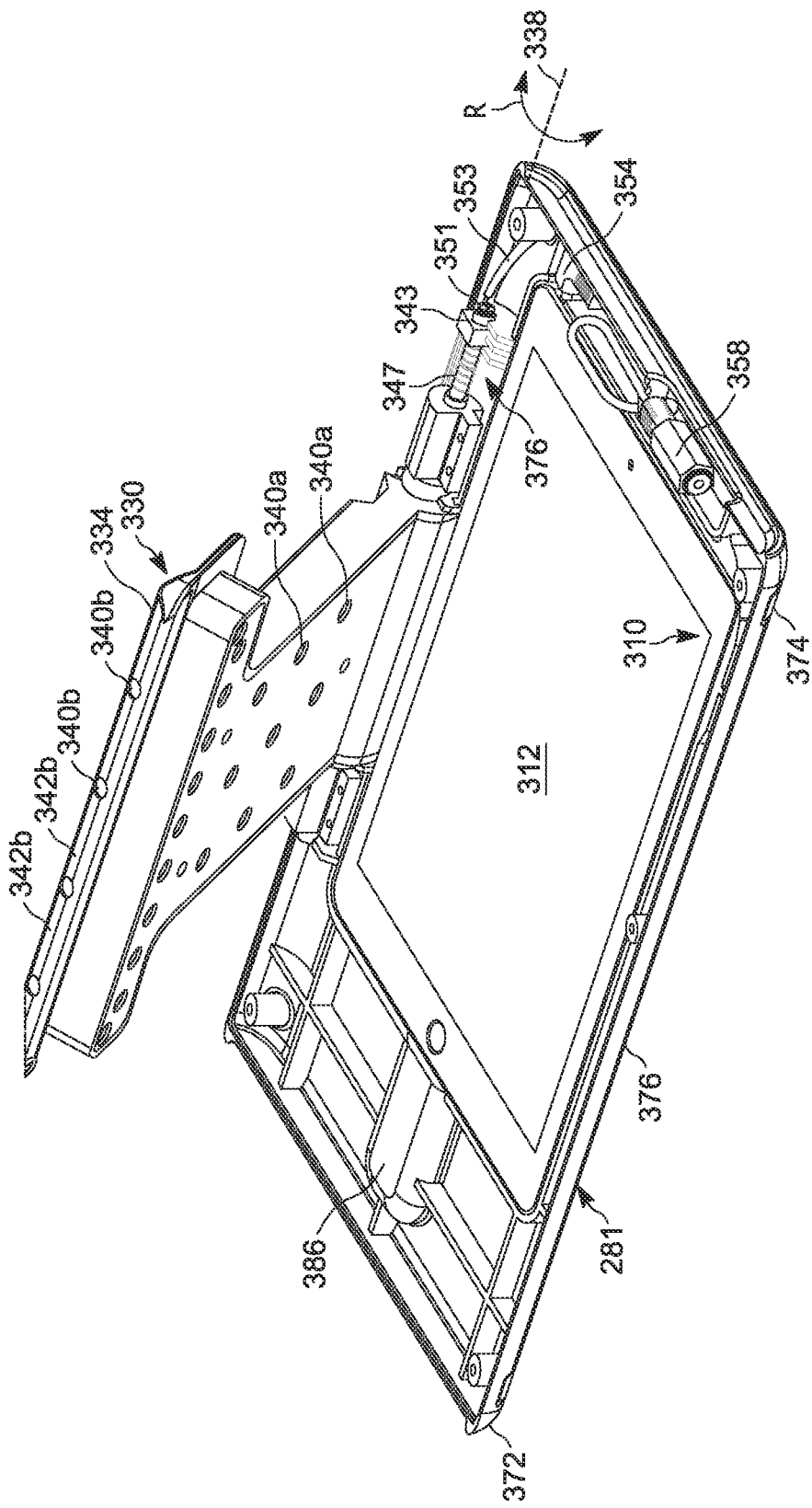
FIGS. 28A and 28B depict additional portions of the housing being attached.
Figure 28B:
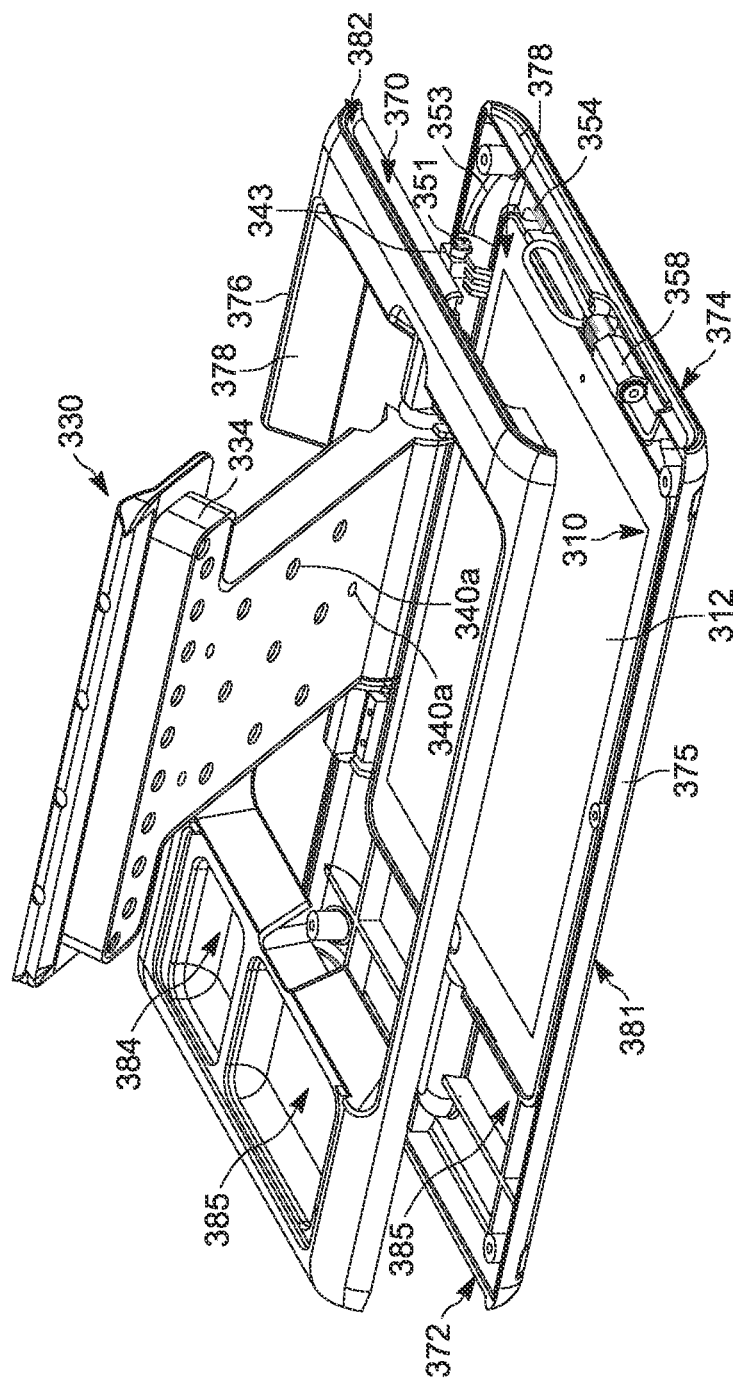
Figure 29:
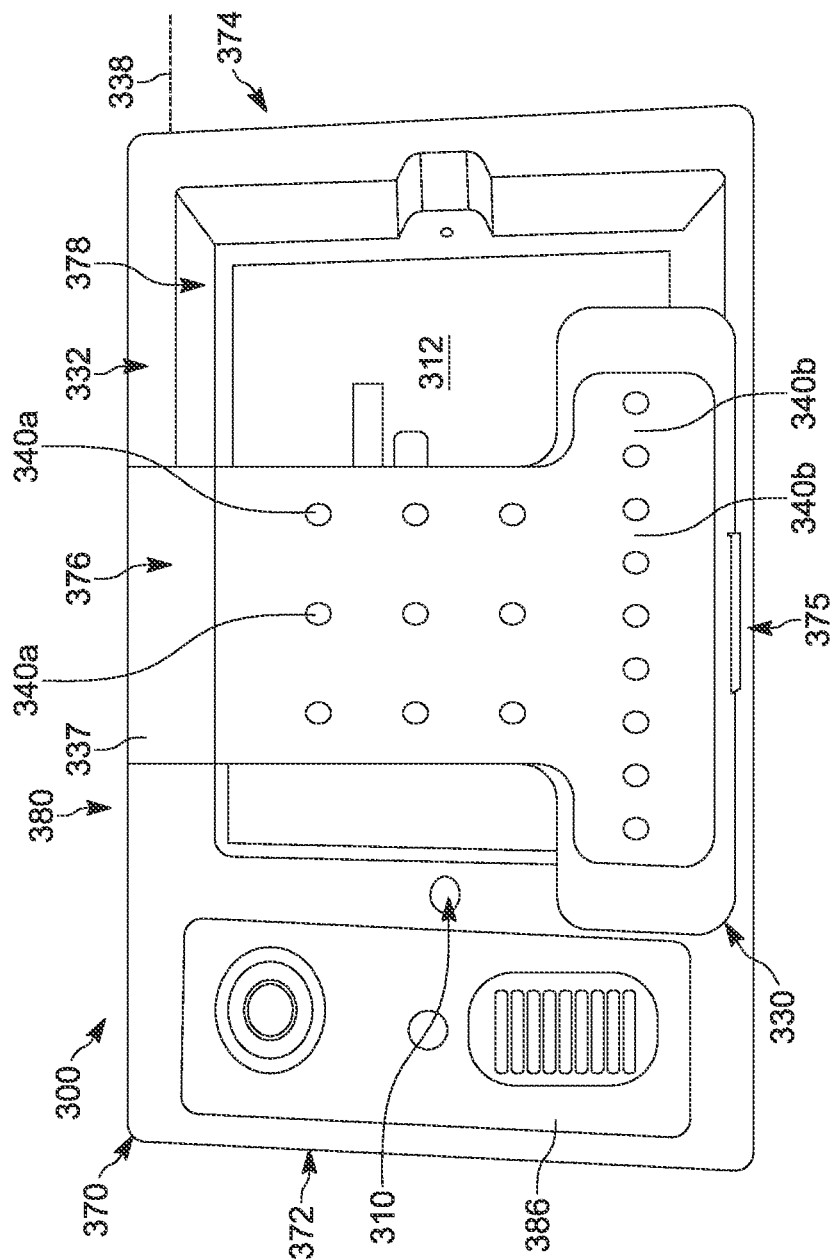
FIG. 29 depicts an example of a completed housing and associated tablet computer to provide a testing apparatus.
Figure 30A:
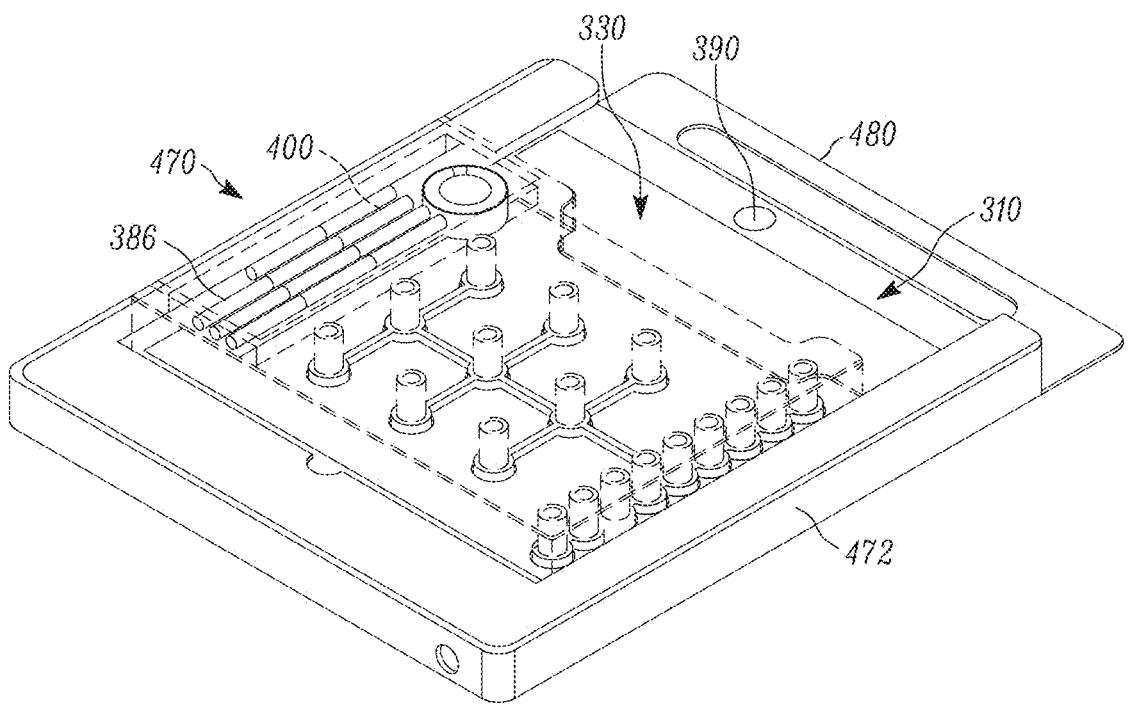
FIGS. 30A-33E depict alternative configurations for housings for the testing devices described herein.
Figure 30B:
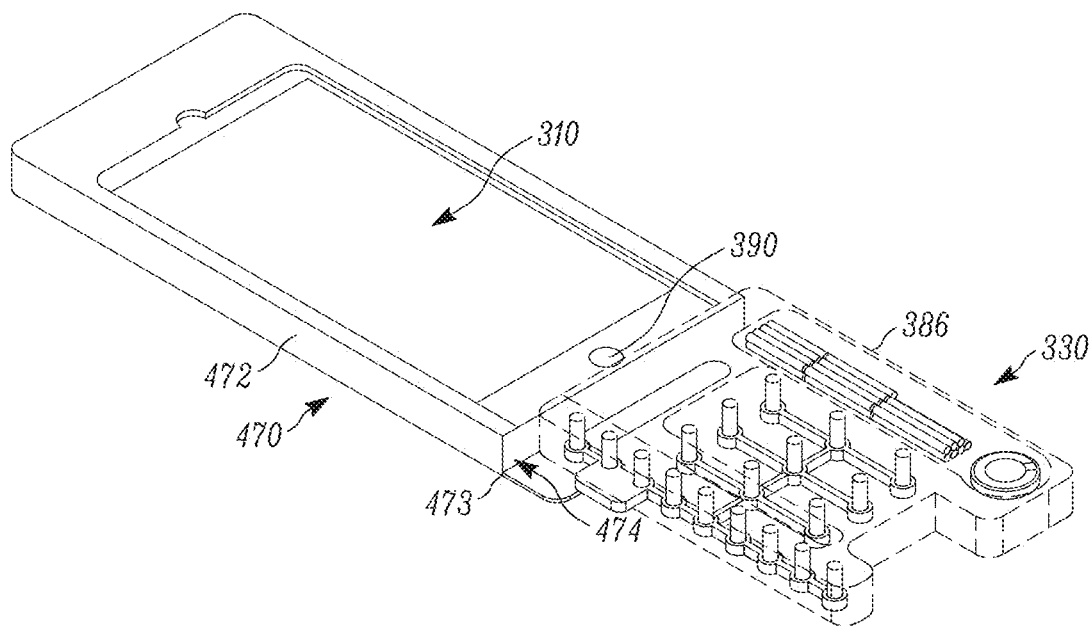
Figure 30C:
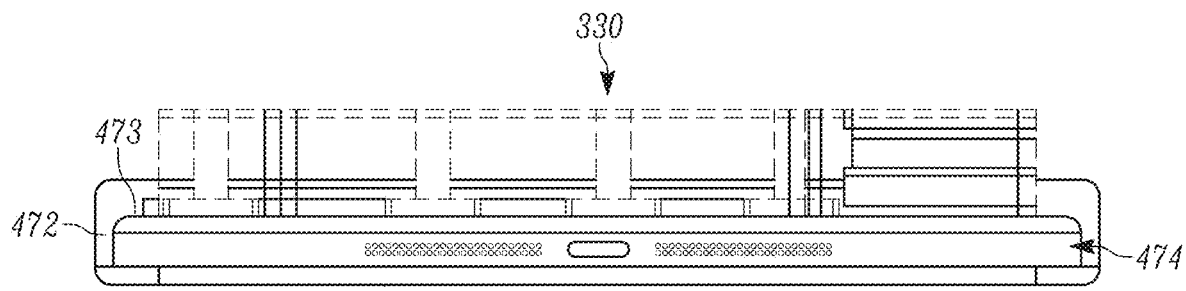
Figure 30D:
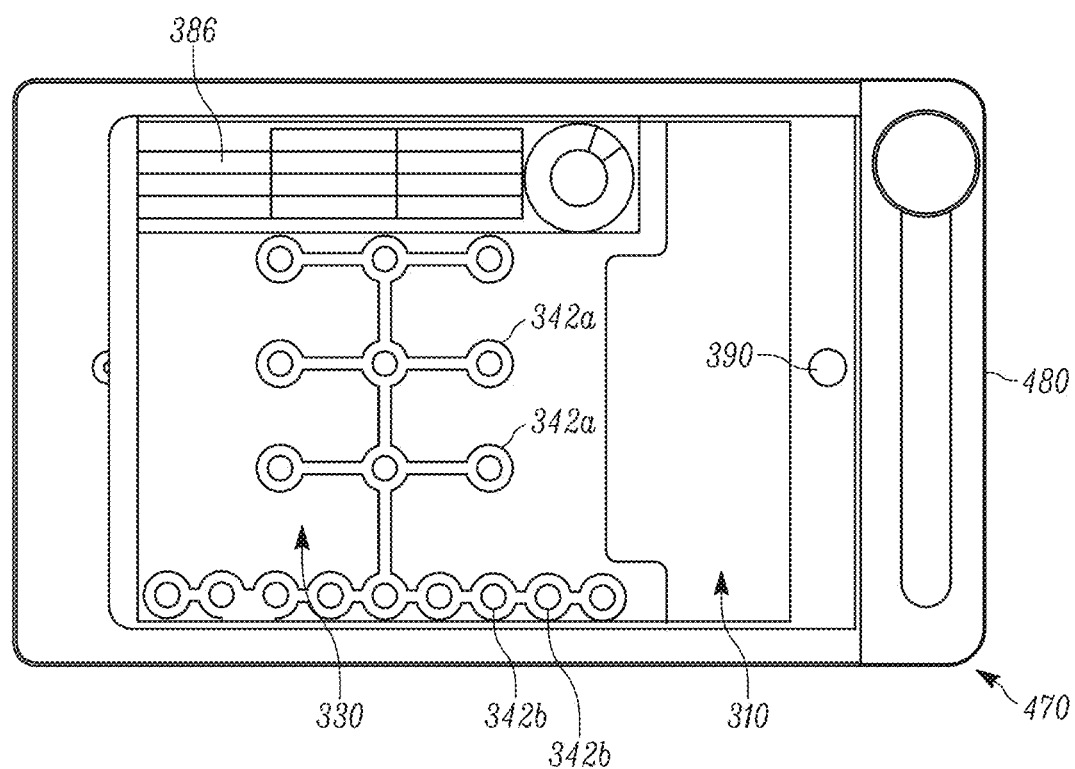

FIGS. 28A and 28B demonstrate assembly views of the apparatus 300 showing attachment between lower and upper housing portions 381 and 382. In FIG. 28A, the computing device 310 is positioned within the lower housing portion 381, such as within a receptacle dimensioned and configured to receive the computing device therein. In FIG. 28A, the platform is rotatably attached to the lower housing portion 381 via the hinge, as mentioned above. In FIG. 28B, the upper housing portion 382 is placed over the lower portion 381, such as to sandwich the computing device therein. The lower and upper housing portions can be connected together via snap fit, adhesive, ultrasonic welding or the like to provide the assembled apparatus 300, such as shown in FIG. 29.

In use, the apparatus 300 is removed from a storage area and carried to/placed on a table or surface. A soft protective cover (if applicable) is removed. The test fixture 330 is pivoted about the hinge 337 in the direction R away from the touch screen 312 to access the entire touch screen and initiate the desired test. When the test is ready, the test fixture 330 is pivoted about the hinge 337 in the direction R to a position overlying the touch screen 312. This places the apertures 340a and/or the apertures 340b in positions overlying predetermined portions of the touch-sensitive screen 312 (e.g., corresponding to the test position). For example, the computing device can be programmed to generate an interactive graphical user interface that includes interactive GUI elements aligned with one or more of the apertures 340a, such as during a given test, such as disclosed herein.

One or more of the pegs 400 can be removed from the aperture(s) 342b or the chamber 385 and inserted into one of the apertures 340a, allowing the pegs to extend entirely through the base 332 into proximity with the touch screen 312. The touch screen 312 detects and determines when any of the pegs 400 are in contact with the GUI.

The first end 372 of the upper housing portion 382 includes recessed chambers 384, 385 accessible by a door 386 that is pivotably connected to the front of the housing 370. The chambers 384 and 385 can include a series of parallel slots or other containing features, such as can be used for receiving and storing the pegs when not in use. The door 386 can securely lock (e.g., snap-fit) with the remainder of the housing 370 to ensure the door remains closed during storage, transport, and manipulation of the apparatus 300.

Figure 24:
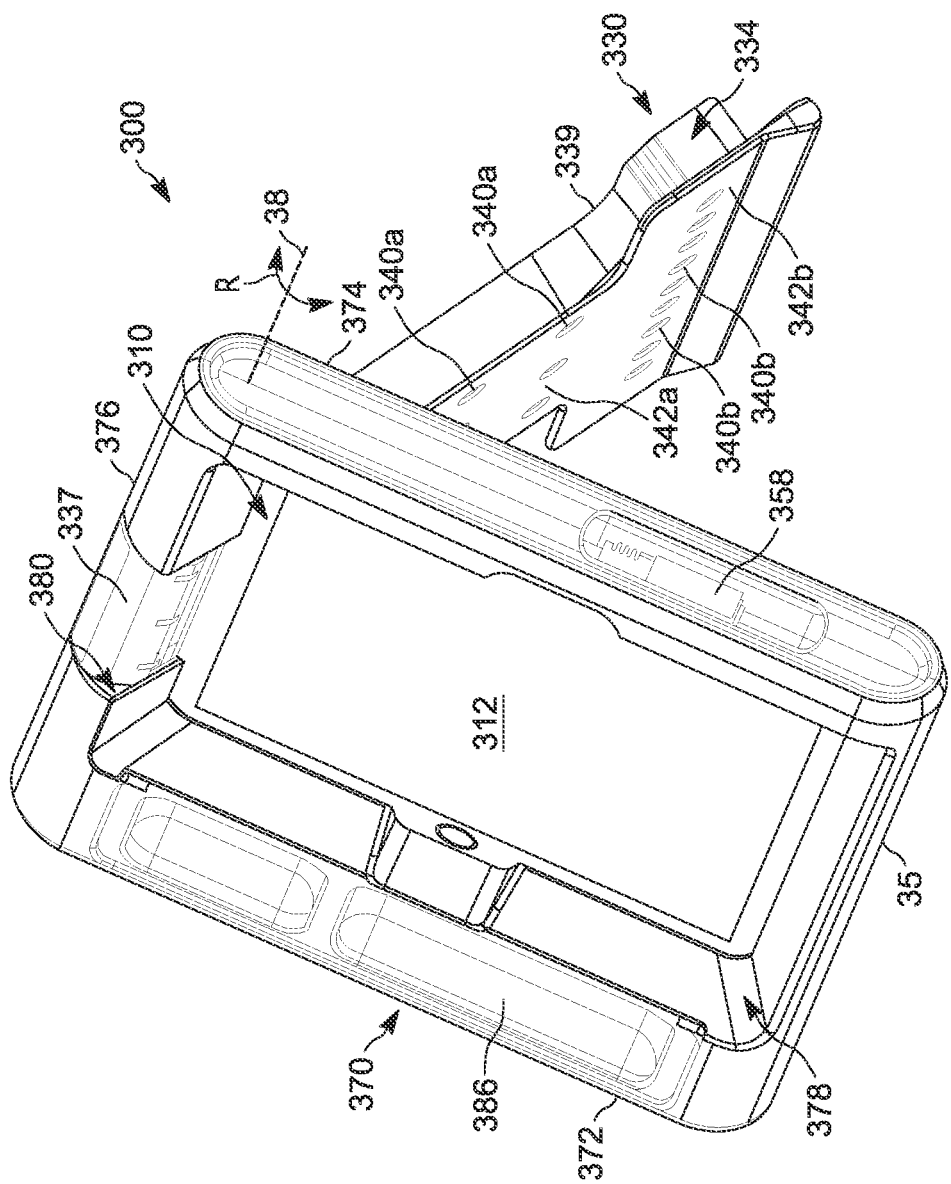
FIGS. 24-25 depict an example testing apparatus and housing that can be used to evaluate the patient's manual dexterity.

Due to the construction of the hinge 337, the test fixture 330 can also function as a leg or kickstand to support the housing and computing device 310 in a generally upright orientation without leaning against another object or the aid of a person. As shown in FIG. 24, the test fixture 330 can be rotated in the direction R out of the interior space 378 to a position extending behind the computing device 310. When the angle between the rotated test fixture 330 and housing 370 approaches, for example, 90°, the test fixture is released. The friction hinge 337 maintains the desired angle between the rotated test fixture 330 and housing 370 while the rubberized perimeter 334 on the base 332 grips the surface on which the apparatus 300 is placed, e.g., countertop, table top, etc.

In some embodiments, the hinge may comprise a ratchet or a locking device, such as a pin through the housing preventing rotation or a magnet, in addition to or in lieu of the friction fit. Consequently, the apparatus 300 has a desired viewing orientation for the user that is maintained by the friction hinge 337 and increased friction between the perimeter 334 and contact surface, thereby facilitating reading the touch screen 312. In some alternate embodiments the text fixture can swing fully around to and flush with the back side of the tablet (opposite the screen). This ability would allow a user to lay the device flat on its back on a surface.

As disclosed herein, the computing device 310 can be programmed to, such as part of neuromotor test program, e.g., a manual function test, for measuring individual peg 400 insertion and removal time in any of the apertures 342a, 342b, i.e., the 9 hole peg test (9HPT). In other examples, the same test program can include other test modules, such as for testing visual acuity by holding the computing device 310 at the correct angle for performing the test, and performing a timed 25 foot walk.

In one testing example, such as for the door 386 is opened to access the pegs 400, which are removed from the chamber 385 and place in the row of apertures 340b in the test fixture 330. The pegs 400 are then moved by hand from the row of apertures 340b to the grid of apertures 340a, with instructions provided on the touch screen 312. The user can access a help button (not shown) on the computing device 310 if needed during the test. To this end, portions of the touch screen 312 can be accessible by the user while the test fixture 330 overlies the touch screen. Moreover, the test fixture 330 can be transparent to enable viewing of the touch screen 312 through the downwardly pivoted test fixture.

Once the test is completed, the pegs 400 are placed back into the chamber 385 and the door 386 closed. The test fixture 330 is pivoted away from the touch screen 312 to complete any remaining tests. Upon completion of all tests, the test fixture 330 is again pivoted to a position overlying the touch screen 312. The protective cover is replaced and the apparatus 300 carried back to storage.

The housing 370 is advantageous in that it helps protect both the computing device 310 and the test fixture 330. The housing 370 is semi-permanent and covers/protects nearly the entire computing device 310, aside from the touch screen 312, which remains at least partially accessible. The housing 370 also maintains easy access to the power button 390 and provides a convenient means of storing the pegs 400 when not in use.

The periphery of the housing 370 is advantageously provided with notches, openings, etc. (not shown) to maintain access to all ports and buttons on the computing device 310 when stored therein, e.g., headphone jack, volume buttons, USB port, etc. For instance, the splitter 356 may be provided to enable the patient to listen to audio instructions while simultaneously performing the prescribed test(s). The splitter 356 can constitute an off-the-shelf splitter, a custom OEM external splitter or use connectors and wire assemblies built into the housing 370.

As a result, the housing 370 provides a protective cover for the computing device 310 that allows the computing device to be used efficiently with the manual dexterity test and any other assessment or questionnaire deliverable via the computing device. The patient can therefore readily listen to and/or visually see instructions provided by the computing device 310. The housing 370 can also be made ergonomic to facilitate grasping, manipulation, and feel for the patient.

FIGS. 30-33 illustrate alternative configurations for housings to be used with the test fixture 330 and computing device 310 described herein. In FIG. 30, the housing 470 is a sliding type in which the computing device 310 is laterally slid into the interior space 474 of the housing. The housing has a U-shaped sidewall 472 defining the interior space 474 and including a series of recessed portions 473 contoured to the shape of the computing device 310. The computing device 310 is slid laterally into the interior space 474, sliding along the recessed portions 473. The contour of the recessed portions 473 helps retain/lock the computing device 310 within the housing 470. The test fixture 330, which is shown with a generally rectangular configuration, can be secured to the computing device before or after the computing device is slid into the housing 470 or afterwards. The housing 470 can include a handle 480 at the open end of the sidewall 472 (or any other place along the sidewall) for grasping/manipulating the apparatus.

Figure 31A:
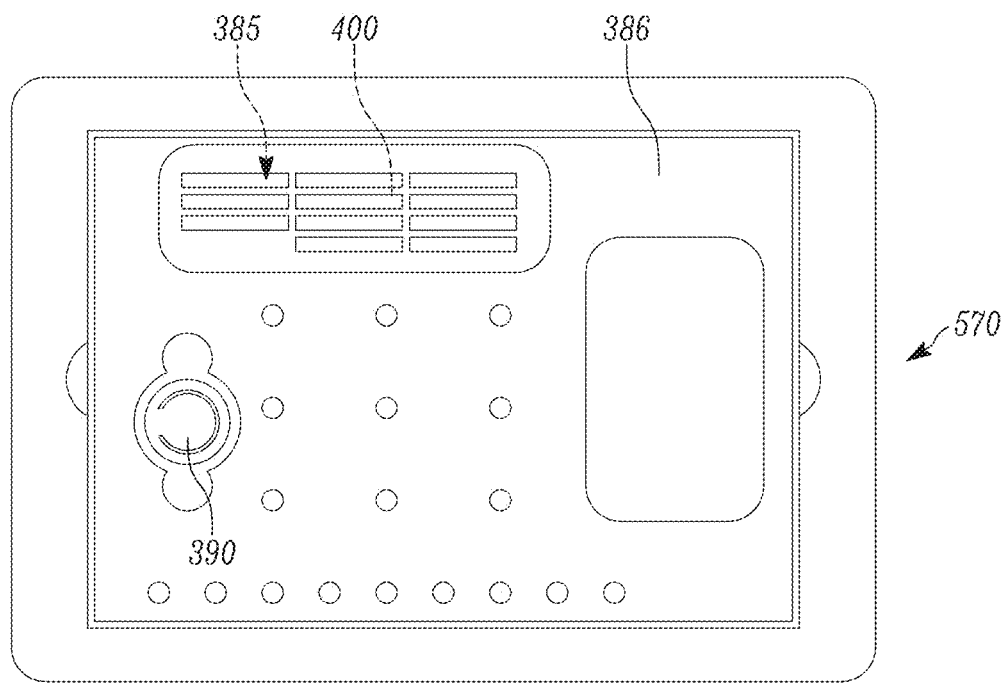
Figure 31B:
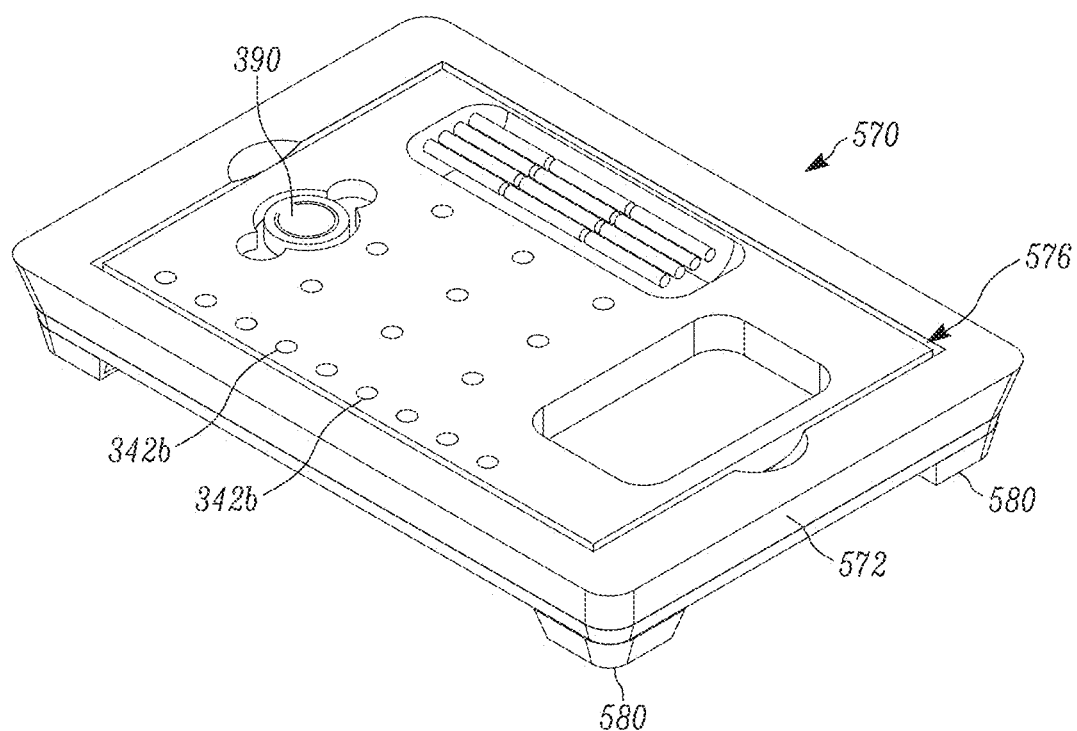
Figure 31C:
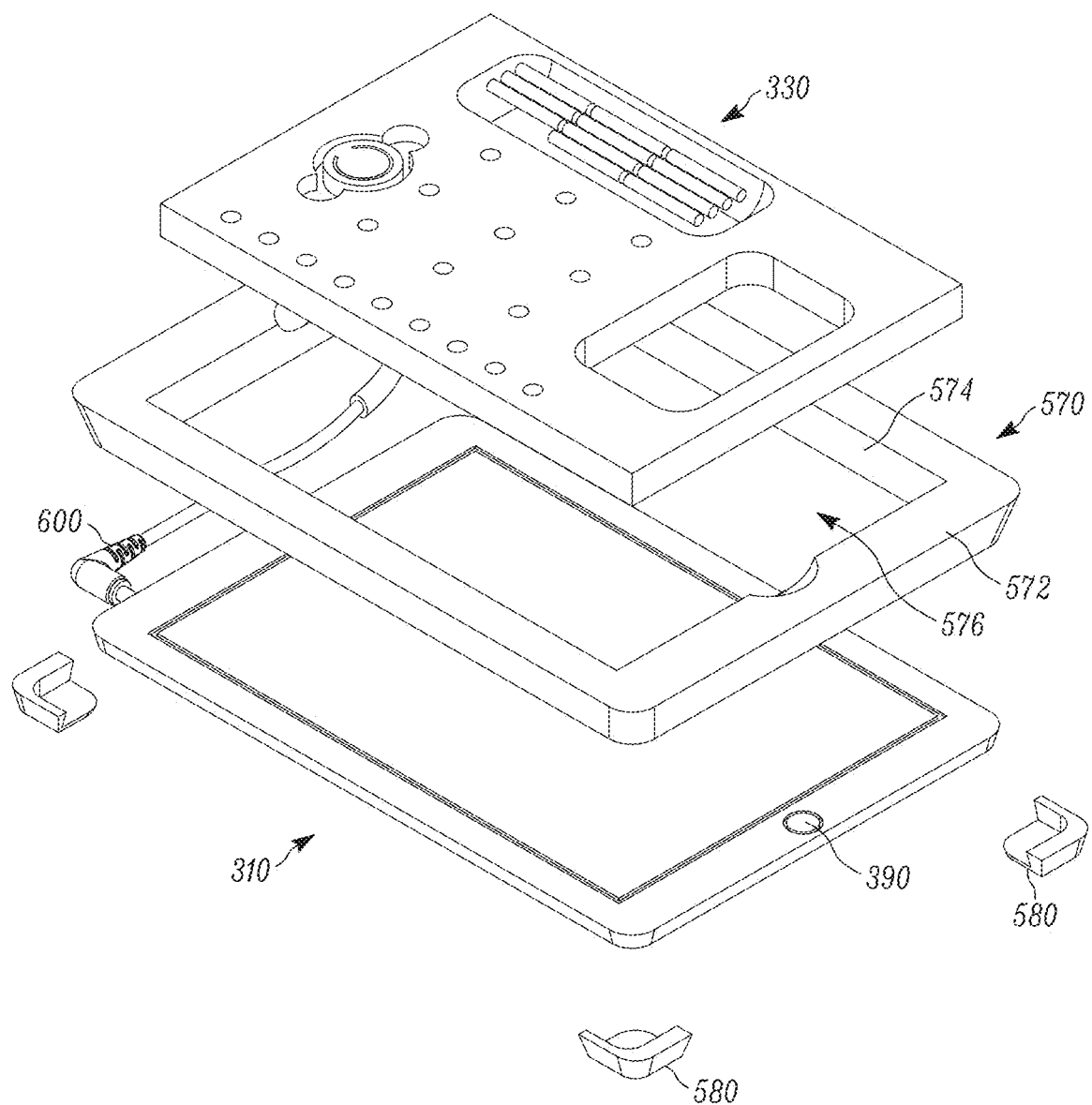
Figure 32A:
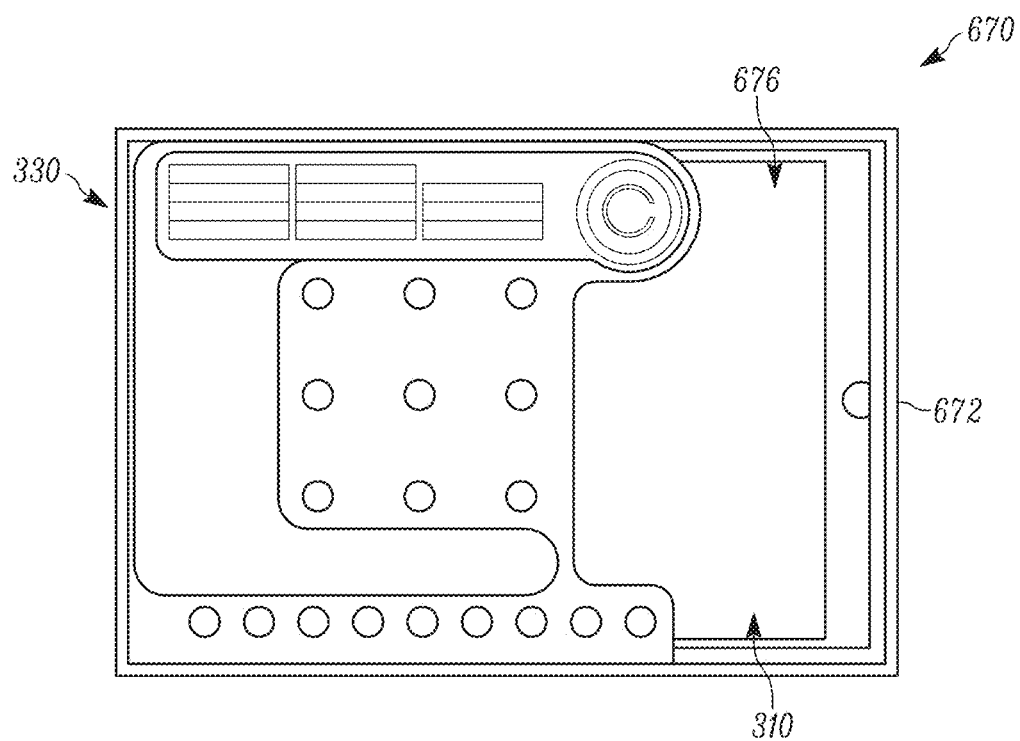
Figure 32B:
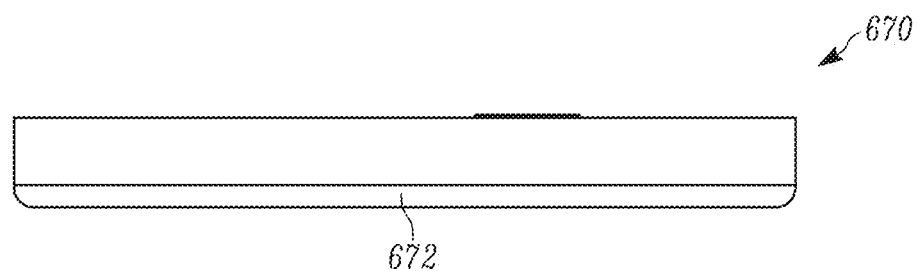
Figure 32C:
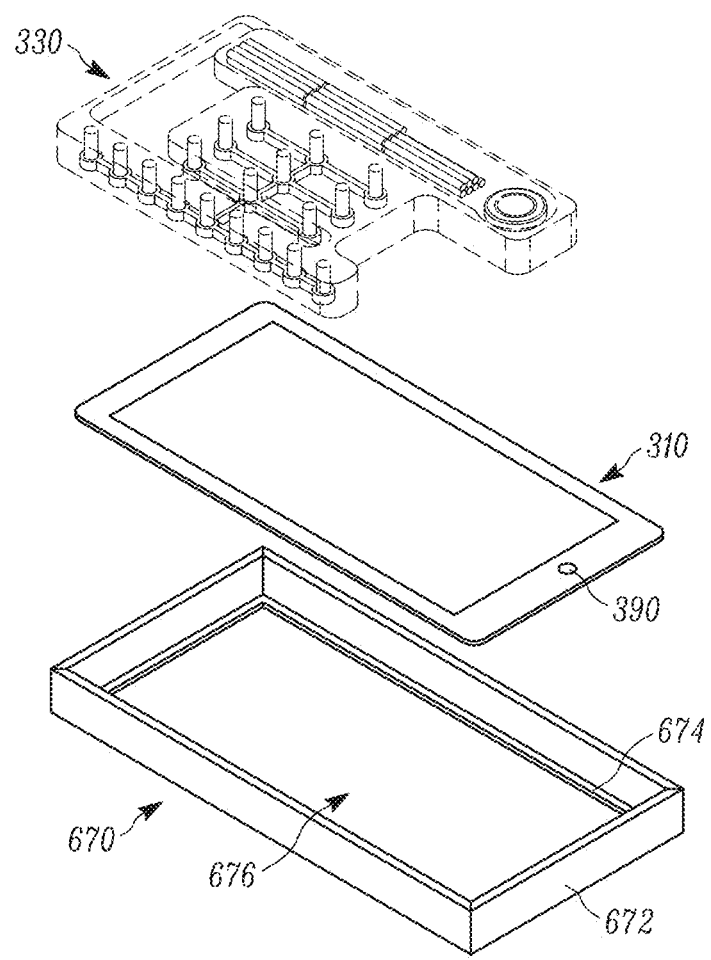
Figure 32D:
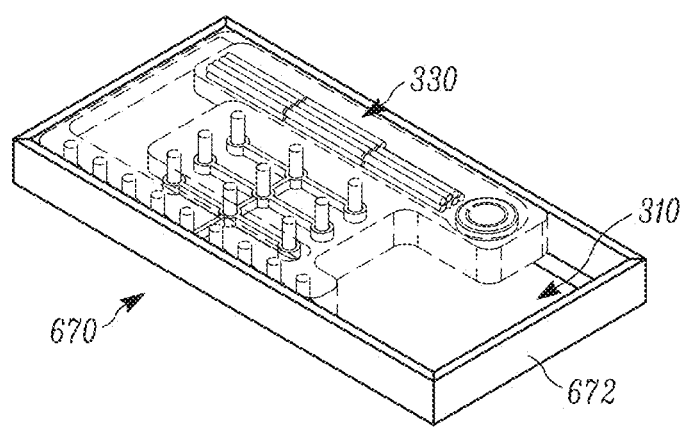
Figure 32E:
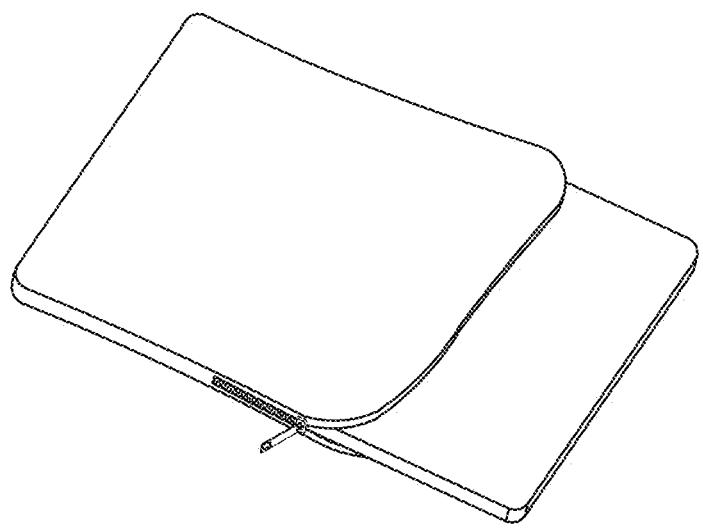
Figure 33A:
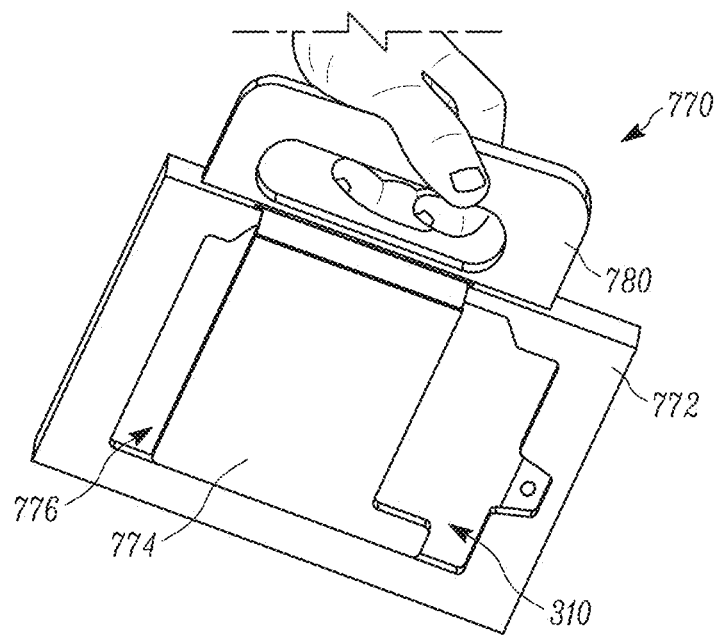
Figure 33B:
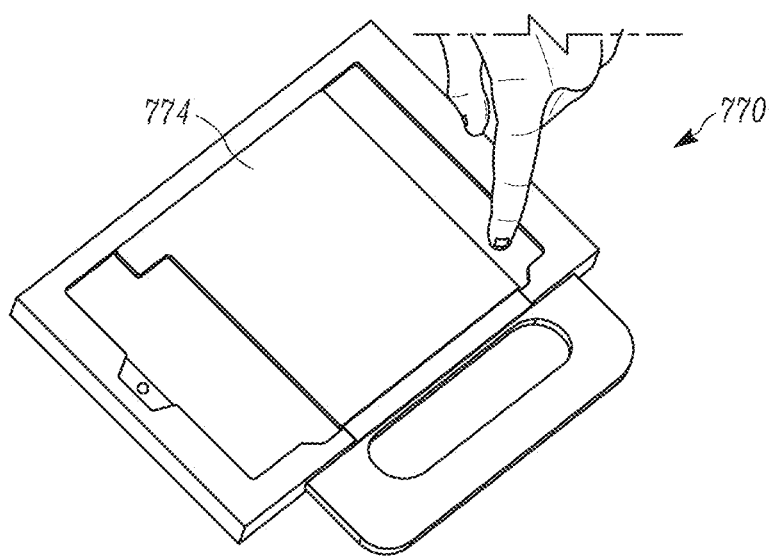
Figure 33C:
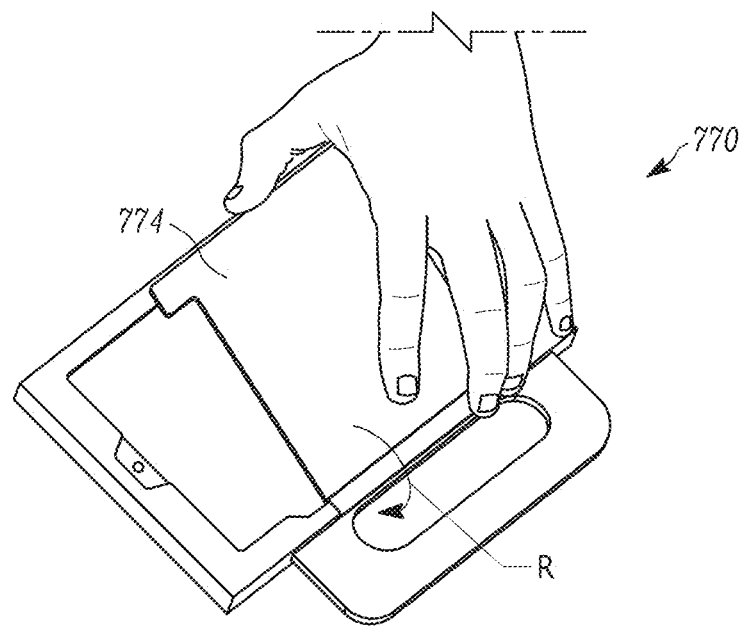
Figure 33D:
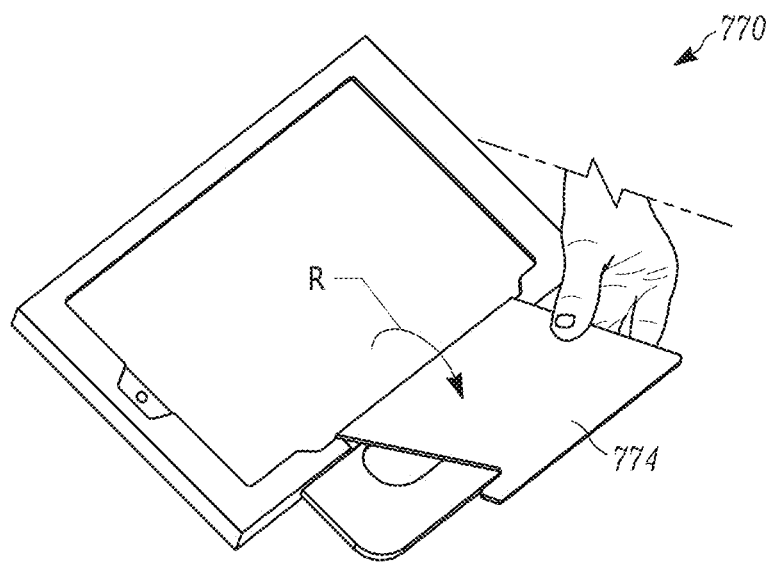
Figure 33E:
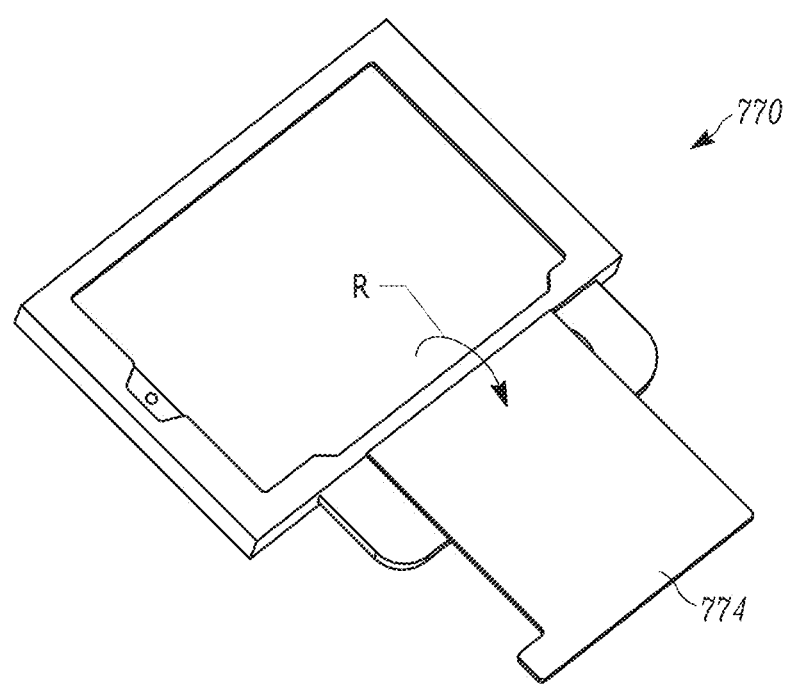

In FIG. 31, the housing 570 has a drop frame configuration having a rectangular sidewall 572 defining an interior space 576. A recess 574 extends into portions of the sidewall 572 to form a ledge that receives the computing device 310 and test fixture 330. One or more feet 580 can be secured to the bottom of the housing 570. A splitter 600 for headphones can be connected to the computing device 310.

Similarly, in FIG. 32, the housing 670 has a deep drop frame configuration having a rectangular sidewall 672 defining an interior space 676. A recess 674 extends into portions of the sidewall 672 to form a ledge that receives the computing device 310 and test fixture 330.

FIG. 33 illustrates a housing 770 for a computing device 310 constituting a lap top. The housing 770 includes a rectangular sidewall 772, a handle 780 extending from the sidewall, and an interior space 776 for receiving the computing device 310. A panel 774 secured to the frame 772 pivots in the direction R to more fully enclose the computing device 310 within the interior space 776—for protection—or to access the interior space.

Routine collection of clinical data from neurological assessments is impaired by the requirement for qualified staff to administer tests and record the data in a consistent and timely manner. Collection and aggregation of this data over time is important in assessing disease progression and response to treatment in MS patients, as reflected in the widespread use of the traditional forms of these neurological assessments in clinical trials. The apparatus disclosed herein allows the patient to self-administer neurological tests that are widely accepted by the neurological community, yet not routinely used in clinical practice due to time and resource constraints.

The immediate need for this design is therefore to allow a reduction in clinical staff required to administer functional tests, which is accomplished by having largely self-administered tests. The autonomous nature of the apparatus would also allow for use by patients that are ambulatory, e.g., in-home assessment by the patients themselves. This would allow for greater resolution in functional data when making clinical decisions. By reducing the workload on the clinical staff, a greater amount of data can be captured for each patient. The availability of this data to clinical staff will enhance the care of MS patients by providing routine, quantitative measures of function that are currently not captured. Further, acquisition of data by a computer based system allows for more reliable, standardized and objective data and easier storage, retrieval and analysis of the data, including analysis with respect to patient populations and longitudinal data.

In view of the foregoing, it will be appreciated that the data collected via the approach disclosed herein provides facilitates automated assessment of a plurality of tests. For example, the approach provides a patient-centered neurological performance system, it can be used in non-medical setting (autonomously by the patient at home or other remote location) as well as medical settings typically not equipped to provide certain types of healthcare, such as at rural hospitals. The data collected for each given patient for a test sessions can be used for patient evaluation as well as for management of the patient's condition. Additionally, since the cost of the test system is inexpensive compared to many existing systems, the systems and methods disclosed herein facilitate clinical research projects, including clinical trials.

The testing can be implemented, for example, via a tablet computer, and can employ a graphical user interface on a portable computing device to implement one or more neurological and neuropsychological performance test method. For instance, the test method(s) can be utilized to help characterize a patient's multiple sclerosis or other neurological disorder (e.g., Parkinson's or essential tremor). As disclosed herein, the method can be self-administered by the patient himself/herself (as opposed to traditional clinician supervised testing which needs to be done by a trained technician). Thus the approach disclosed herein facilitates distance-based monitoring such as through telemedicine. Additionally, since the testing can be self-administered, it enables a care provider (e.g. a physician) to monitor the patient's condition over time to determine the course of disease and the effect of intervention for each of a plurality of patients.

The care provider can access a database to retrieve test results for a plurality of different patients that conducted the test at different remote locations, via a tablet computer where a test was implemented or a remote computer (e.g., smart phone, desktop PC or the like). As a further example, the test results can be communicated to one or more providers. This can be done by simply reviewing the results on the computing device or the results can be sent to the provider(s) via a network connection, as disclosed herein. The test results for one or more subjects, for example, can be stored in a database in a server for further analysis and comparison. For instance, test data can be aggregated for a plurality of patients, such as for clinical research (e.g., in MS), including clinical trials and other forms of clinical research. Such test results for multiple tasks completed over a different time intervals (e.g., over a period of a day or a given week) can be evaluated to set one or stimulation parameters.

As will be appreciated by those skilled in the art, portions of the devices, systems and methods disclosed herein data processing system or computer program product. Accordingly, such features may take the form of an entirely hardware embodiment, an entirely software embodiment, or an embodiment combining software and hardware. Furthermore, portions of the invention may comprise a computer program product on a computer-usable storage medium having computer readable program code on the medium. Any suitable computer-readable medium may be utilized including, but not limited to, static and dynamic storage devices, hard disks, optical storage devices, and magnetic storage devices.

Figure 34:
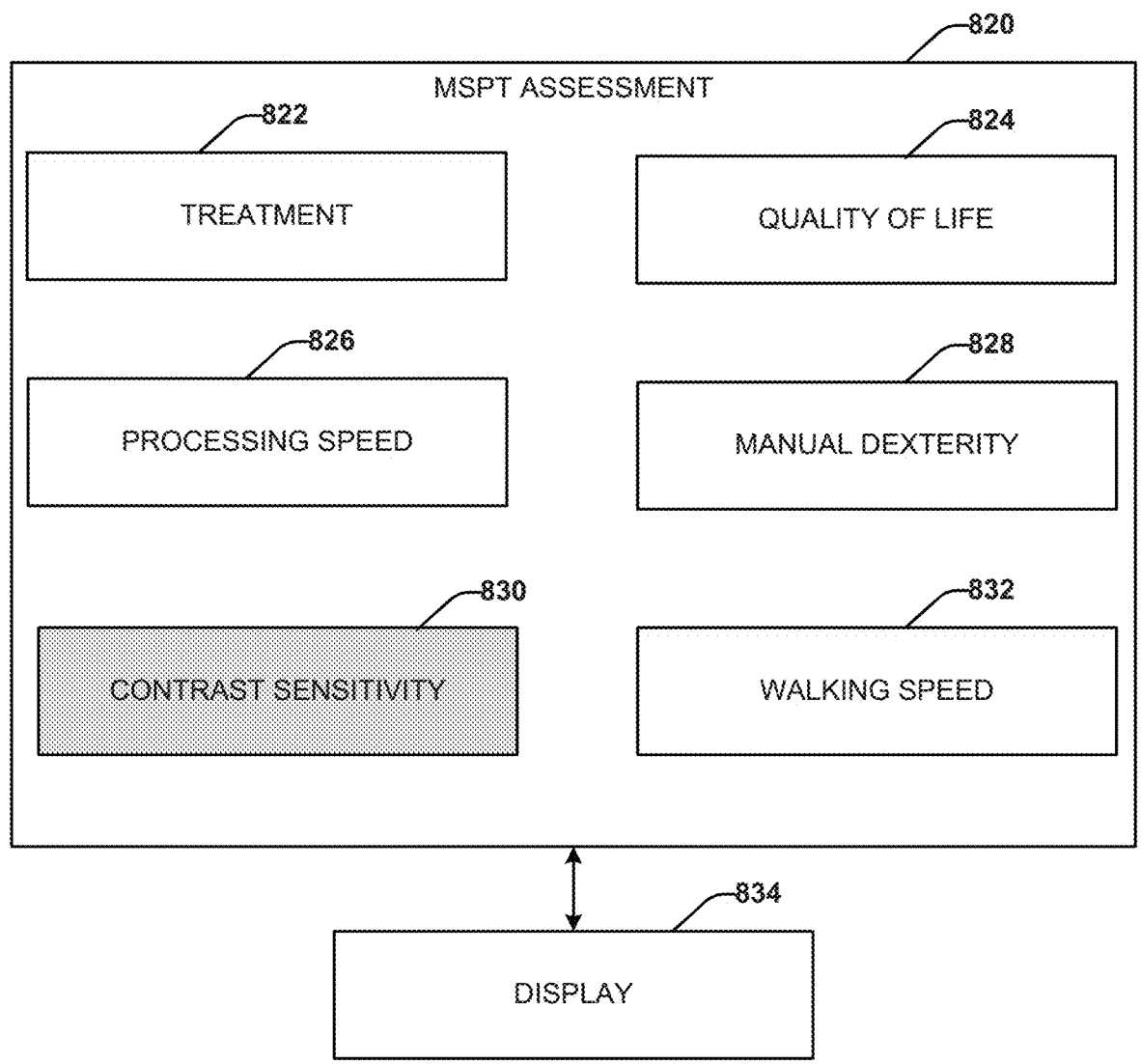
FIG. 34 depicts an example of different modules that can be part of a multiple sclerosis performance test (MSPT).

FIG. 34 shows an example of various testing modules of an example MSPT assessment system 820. For example, the modules can include a treatment module 822, a quality of life module 824, a processing speed module 826, a manual dexterity module 828, a contrast sensitivity module 830, and a walking speed module 832. The modules can be implemented according to the examples disclosed herein with respect to FIGS. 2-23. Results of the MSPT can be visualized on the display 834. Additionally, aspects of each of the modules 822-830 can be displayed on the display 834 in a user-interactive manner. For example, the display 834 can be an input device, an output device, and/or an input/output device that can allow a user input and/or a resulting visualization. In some examples, the display can be part of a computing device that includes one or more processing unit and memory, which can execute instructions corresponding to the modules 822-830 and store data in the memory to document results of user interactions and measurements via the respective modules.

As an example, the treatment module 822 is stored in memory as executable instructions to provide one or more questionnaires, such as a questionnaire related to upper extremity function, a questionnaire related to lower extremity function, a questionnaire related to sleep, a questionnaire related to fatigue, a questionnaire related to anxiety, a questionnaire related to depression, a questionnaire related to stigma, a questionnaire related to positive affect and well being, a questionnaire related to applied cognition, a questionnaire related to executive function, a questionnaire related to the ability to participate in social roles, a questionnaire related to satisfaction with social roles, and/or a questionnaire related to emotional and behavioral dyscontrol. A score can be provided per question as an integer value indicating the patient's response (e.g., 1 Never, 2 Almost never, 3 Sometimes, 4 Often, 5 Almost always).

The quality of life module 824 is stored in memory as executable instructions to ask patients (e.g., in a graphical fashion via a GUI) to rate their quality of life for various questions related to neurological function. The questions can be broken into sub-tests based on domains of function that can include, for example: upper extremity, lower extremity, sleep, fatigue, anxiety, depression, stigma, positive affect and well being, cognitive function, satisfaction with social roles, and emotional and behavioral dyscontrol. The subtests can be independent from each other and may be administered serially with the results not affecting subsequent tests. A score can be provided per question as an integer value indicating the patient's response (e.g., 1 Never, 2 Almost never, 3 Sometimes, 4 Often, 5 Almost always).

The processing speed module 826 is stored in memory as executable instructions to provide a symbol-digit matching test in which subjects can be given an answer key, displaying correct symbol-digit pairings. Then the subject can be presented with symbols and blank spaces beneath them and can be required to select the number that corresponds with each symbol based on the answer key. The test can be scored based on the total number of correctly matched symbol-digit pairs in two minutes. In some instances, the score can be additionally based on the response time per symbol and the number of incorrect responses.

The manual dexterity module 828 is stored in memory as executable instructions to enable user interaction with the testing apparatus by allowing patients to manipulate physical pegs into a grid overlay with their dominant hand and their non-dominant hand in sequence (e.g., 2 trials per hand, 60 seconds per trial). The module 828 can correspond to the manual function test module disclosed with respect to FIGS. 4-6. This test can be implemented using any of the example housings disclosed herein, such as demonstrated in FIGS. 24-33 with corresponding graphics appearing on the touch screen through the test fixture (e.g., constituting a grid overlay) of the testing apparatus with instructions that specify which hand to use during each trial. A score can be calculated based on the number of pegs correctly placed, a time to place the pegs, a number of pegs dropped, and the like. For example, time to place pegs can be calculated as the time between the touch screen interface detecting removal of a peg from its starting position and insertion of the given peg into the correct peg hole In some examples the manual dexterity test can be implemented (e.g., including with the housing and pegs of FIGS. 24-33) according to a workflow corresponding to instructions executed by the tablet computer of the testing apparatus.

The contrast sensitivity module 830 can apply a low contrast visual sensitivity test such as disclosed herein. In some examples, the contrast sensitivity module 830 can apply the low contrast letter acuity test, which can show the patient lines consisting of a plurality of different optotypes (e.g., about 5 optotypes) of a fixed contrast level and size. Additionally or alternatively, the The walking speed module 832 can have functionality to enable patients to measure the time it takes for them to walk a specified distance. A score can be based on the time taken to walk the specified distance. In this module 832, a patient performs tests to measure the time it takes for them to walk a specified distance. Prior to starting any trials, a patient may first answers questions provided by the tablet computing device, regarding their utilization of any walking aids or Ankle and Foot Orthoses (AFOs) usage. Once these questions are answered, the patient is presented with instructions instructing them how to successfully complete the module. Part of the instructions is testing the Low Energy Bluetooth (LE-BT) remote to ensure it is properly paired to the device. Other possible remote triggers include infrared, Near Field Communications, sound activation, light or laser activation, motion sensors, force sensors, accelerometers and so forth.

After the instructions, the test phase begins. The patient makes their way to a prescribed testing course. Once at the starting line, they press the remote once to begin the trial. Upon crossing the finish line, they press the remote again to stop the trial. The patient then returns to the device to confirm that the trial was complete successfully. In the event the trial was not successful, the patient has the ability to repeat the trial. Repeating a trial stores the previous trial data but marks it as invalid. The patient repeats this cycle for every trial that is administered.

An alternate administration method may involve an administrator or other person (e.g., friend or family member) tapping the iPad screen to start and stop a trial; this is to be used in place of or in conjunction with the LE-BT remote. The method of starting and stopping a trial will be recorded. In the event that a trial reaches maximum duration, the trial may be scored as having the maximum time and stored as successfully completed with a TIMEOUT=TRUE flag.

The apparatus and computing device enable one or more of such tests to be readily self-administered by the subject, as opposed to by a trained technician; however, a trained technician can also administer such tests, if desired. This is enabled because the application of each test module and associated score scoring is automated by executable instructions programmed to process acquired testing data and to score tests based on testing data acquired during each of the tests by the computer via which the tests are administered. In some examples, the data from these tests can be aggregated at the computing device and transmitted to a provider database via a network. This process or sending the test data can also be automated. The test data can be collected (e.g., in a database) for many patients for a variety of evaluative purposes, such as to facilitate patient monitoring, provide population statistics, and drug development.

As an example, the tests and associated instructions can be stored and executed on a server (e.g., database 38 of FIG. 1, such as on a web server) and accessed at another remote device (e.g., a computing device) for user interaction, such as via a web browser or other interface that is programmed to interact with the user interface that is generated. In some cases, the functionality can be distributed between the server and the remote device in which certain instructions are executed by the remote device and other instructions are executed by the server. In other examples, the instructions and data can be stored and executed locally in a computing device (e.g., a portable or mobile device), such as a tablet computer.

Figure 35:
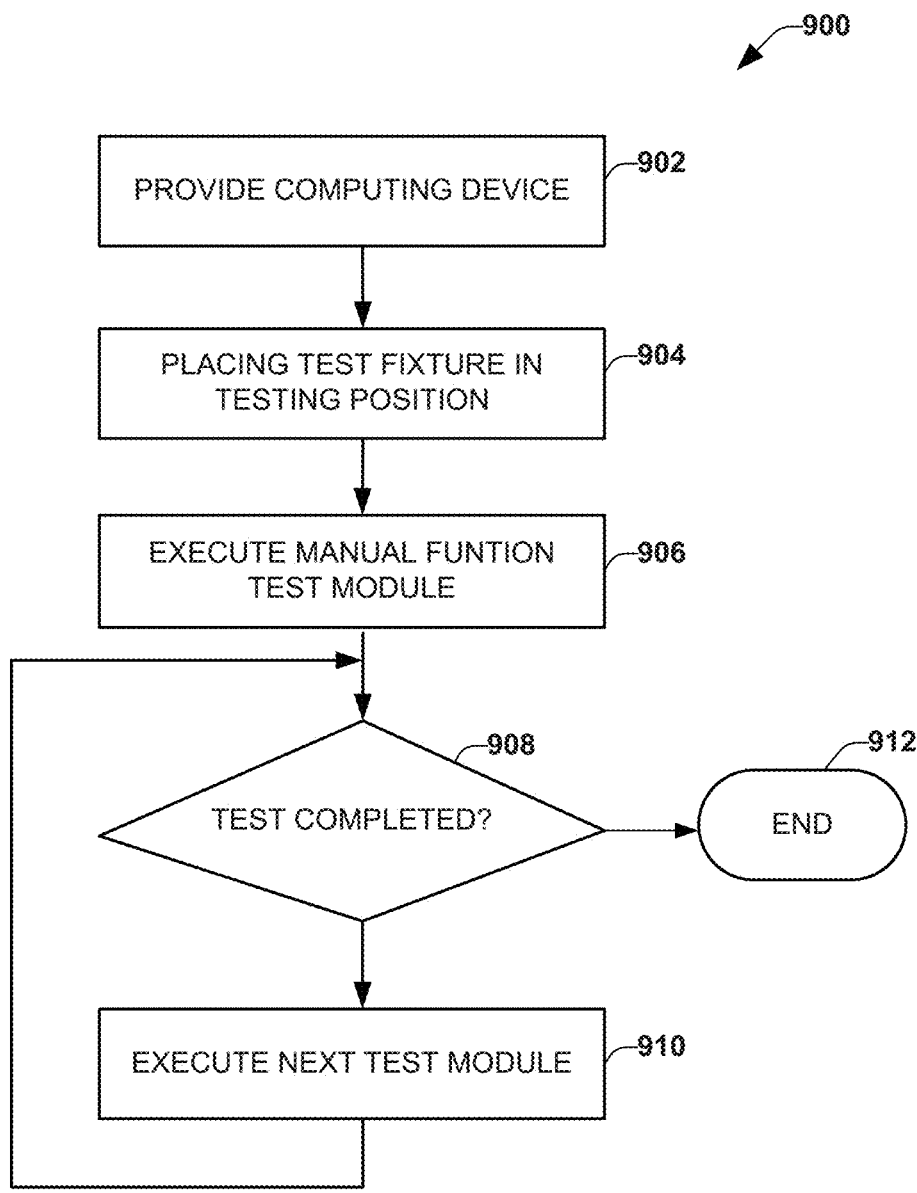
FIG. 35 depicts an example of a method related to performing testing for evaluation of cognitive and/or neuromotor function.

FIG. 35 is a flow diagram depicting an example of a method 900 for performing testing for evaluation of cognitive and/or neuromotor function, such as for the MSPT. The method 900 can be implemented using a mobile computing apparatus, such as disclosed herein. The method begins at 902 by providing a computing device having a touch screen interface. The computing device includes memory to store instructions corresponding to at least a manual function test module (e.g., 62, 80, 828). As disclosed herein, the computing device can be used to store instructions to perform other test modules, including one or more of a cognitive processing speed test module (e.g., 110, 130 and/or 826), a gait test module (e.g., 230, 240, 250, 832), a balance test module (e.g., 160, 170, 190), and a visual acuity or contrast sensitivity test module (e.g., 290, 830).

Figure 25:
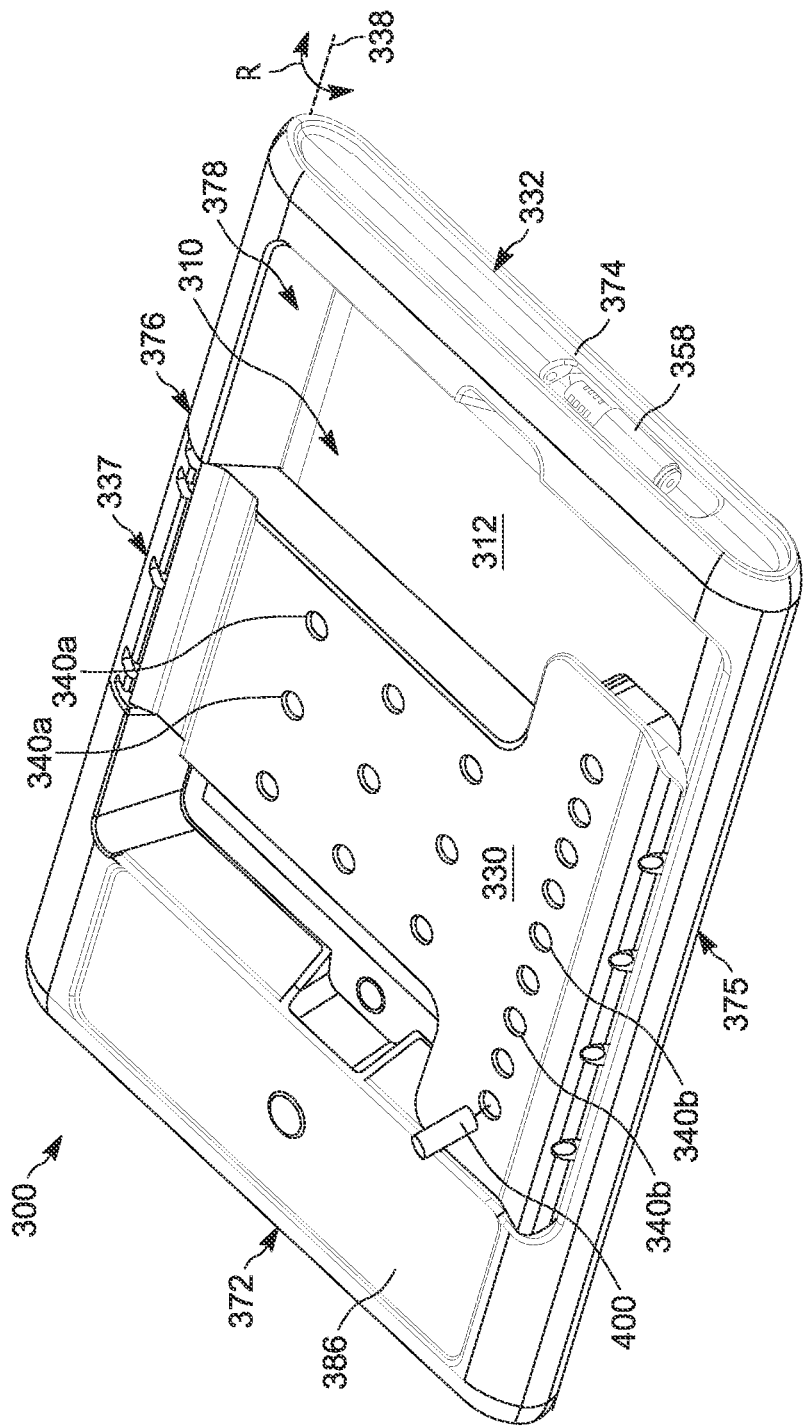

At 904, the method includes placing a test fixture (e.g., platform 330) in a test position in which the test fixture is in an overlying position with the touch screen (see, e.g., FIGS. 5 or 25). As disclosed herein, the test fixture is pivotably connected to a base, which is attached to the computing device (e.g., 310). The connection provides for rotational movement of the test fixture with respect to the touch screen interface of the computing device between the test position (see, e.g., FIGS. 25 and 29) and a support position (see, e.g., FIG. 24) in which the base is operative to support the base and the computing device. The test fixture includes a plurality of receptacles for receiving a plurality of contact members that, when placed in the receptacles while the test fixture is in the test position, enable interaction that is detectable by the touch screen in the absence of direct contact by the user.

At 906, the method includes executing the manual function test module and storing test data corresponding to user inputs in response to placing the contact members into the receptacles while the test fixture is in the test position during the execution thereof. The manual function test module calculates time values associated with the placing of the contact members and store the time values as part of the test data in memory.

At 908, a determination can be made whether the testing method is complete. If additional testing modules are to be performed, the method proceeds to 910. At 910, the method further includes executing the next test module and storing other test data in the memory based on user interactions with the computing device during the execution thereof. In connection with performing the additional testing, the user can move test fixture from the testing position for the manual function test to the support or another position to provide desired access to the touch screen (e.g., the apparatus can lay flat or be supported by the test fixture acting as a kickstand). From 912, the method returns to 908. At 908, if the determination is that the testing is complete, the method ends at 912.

Certain embodiments of the invention are described herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. An apparatus comprising:
   a first housing portion comprising a test fixture having a base dimensioned and configured to overlay at least a display screen portion of a computing device, an arrangement of receptacles being formed in the test fixture and configured to receive any respective contact members within the receptacles as to render each of the contact members independently detectable by the computing device while each respective contact member is received in the receptacles, the contact members being separate from the test fixture and receivable in any of the respective receptacles,
   a second housing portion connected to the first housing portion and configured to attach the first housing portion with respect to the display screen portion of the computing device; and
   a mechanical hinge to rotatably connect the first housing portion with the second housing portion to enable the base to be moved into and out of engagement with the display screen of the computing device, wherein the hinge forms part of an electrical path interconnecting the first housing portion with an electrical ground of the computing device.

2. The apparatus of claim 1, wherein the display screen portion of the computing device includes a touch screen configured to detect each of the contact members while received in the receptacles, while the test fixture overlays the touch screen and in the absence of contact by a user.

3. The apparatus of claim 1, wherein the second housing portion includes a contact surface to mechanically and electrically connect the test fixture with a body of the computing device.

4. The apparatus of claim 1, wherein the hinge is configured to provide for rotational movement of the base of the first housing portion between a test position in which the base is in an overlying position with the display screen portion of the computing device and a support position in which the base operates as a support member to support the base and the computing device.

5. The apparatus of claim 4, wherein the support member is a kickstand and the base corresponds to the test fixture and includes the receptacles, which provide viewing access therethrough to the display screen portion when the base is in the overlying position with the display screen portion.

6. An apparatus comprising:
   a first housing portion comprising a test fixture having a base dimensioned and configured to overlay at least a display screen portion of a computing device, an arrangement of receptacles being formed in the test fixture and configured to receive any one of a plurality of contact members within the receptacles as to render each of the contact members independently detectable by the computing device while each respective contact member is received in the receptacles, the contact members being separate from the test fixture and receivable in any of the respective receptacles;
   a second housing portion connected to the first housing portion and configured to attach the first housing portion with respect to the display screen portion of the computing device; and a mechanical hinge to rotatably connect the first housing portion with the second housing portion to enable the base to be moved into and out of engagement with the display screen of the computing device, wherein the base includes electrically conductive material coupled to an interior sidewall of each of the receptacles, the electrically conductive material of the base being electrically connected to an electrical ground of the computing device through an electrical path that includes the hinge and a conducting element that terminates in a plug that is insertable into an electrical connector of the computing device.

7. The apparatus of claim 1, wherein the second housing portion comprises a housing configured to attach to a perimeter portion of the computing device and to enable the base of the first housing portion to move into an overlaying contact test position with the display screen portion of the computing device.

8. The apparatus of claim 1, wherein the arrangement of receptacles comprises a two-dimensional array of receptacles distributed arranged as rows and columns across the test fixture, each of the receptacles in the array of receptacles being configured to receive one of the contact members therein as to render each of the contact members detectable by the computing device.

9. An apparatus comprising:
a first housing portion comprising a test fixture having a base dimensioned and configured to overlay at least a display screen portion of a computing device, an arrangement of receptacles being formed in the test fixture and configured to receive any one of a plurality of contact members within the receptacles as to render each of the contact members independently detectable by the computing device while each respective contact member is received in the receptacles, the contact members being separate from the test fixture and receivable in any of the respective receptacles,
a second housing portion configured to attach to a perimeter portion of the computing device;
a hinge configured to rotatably connect the first housing portion to the second housing portion, in which the hinge forms part of an electrical path interconnecting the first housing portion with an electrical ground of the computing device, wherein the arrangement of receptacles comprises:
a first two-dimensional array of receptacles distributed arranged as rows and columns across the test fixture, each of the receptacles in the first array of receptacles being configured to receive one of the contact members therein as to render each of the contact members detectable by the computing device, and
a second array of receptacles spaced apart from the first array of receptacles and located near an edge of the test fixture, the second array of receptacles further configured to receive selected contact members within the receptacles as to render the selected contact members detectable by the computing device while received in the receptacles.

10. The apparatus of claim 1, wherein the computing device includes a touch screen interface, the computing device including memory configured to store instructions corresponding to at least one test module to perform at least one of a neurological or cognitive function test via the computing device, the computing device to record results data in the memory in response to user interaction with the computing device during each test.

11. The apparatus of claim 1, wherein each of the receptacles has an inner sidewall surface that includes an electrically conductive material adapted to contact a respective contact member when in each receptacle.

12. The apparatus of claim 1, wherein the receptacles include apertures extending completely through the test fixture so the display screen portion is viewable through the receptacles while no contact member is received in the respective receptacles.

* * * * *